(12) United States Patent
Altas et al.

(10) Patent No.: US 9,229,630 B2
(45) Date of Patent: Jan. 5, 2016

(54) USER INTERFACE FOR A PORTABLE OXYGEN CONCENTRATOR

(75) Inventors: Charles R. Altas, Coto de Caza, CA (US); Scott C. Halperin, Orange, CA (US); Peter L. Bliss, Prior Lake, MN (US)

(73) Assignee: RESPIRONICS OXYTEC, INC, Murrysville, PA (US)

( * ) Notice: Subject to any disclaimer, the term of this patent is extended or adjusted under 35 U.S.C. 154(b) by 36 days.

(21) Appl. No.: 11/731,975

(22) Filed: Apr. 2, 2007

(65) Prior Publication Data

US 2009/0167698 A1 Jul. 2, 2009

Related U.S. Application Data

(60) Provisional application No. 60/788,916, filed on Apr. 3, 2006, provisional application No. 60/744,196, filed on Apr. 3, 2006, provisional application No. 60/744,197, filed on Apr. 3, 2006, provisional application No. 60/744,271, filed on Apr. 4, 2006, provisional application No. 60/744,272, filed on Apr. 4, 2006.

(51) Int. Cl.
*G06F 3/048* (2013.01)
*G06F 3/0488* (2013.01)

(52) U.S. Cl.
CPC .................................. *G06F 3/0488* (2013.01)

(58) Field of Classification Search
CPC ........................................................ G06F 3/0488
USPC .................................................. 345/173–184
See application file for complete search history.

(56) References Cited

U.S. PATENT DOCUMENTS

| | | | |
|---|---|---|---|
| 4,826,510 A * | 5/1989 | McCombs ...................... 96/127 |
| 4,859,217 A | 8/1989 | Chao |
| 4,898,578 A * | 2/1990 | Rubalcaba, Jr. ................ 604/66 |
| 5,071,453 A | 12/1991 | Hradek et al. |
| 5,354,361 A | 10/1994 | Coffield |
| 5,531,807 A * | 7/1996 | McCombs ...................... 95/26 |
| 5,858,062 A | 1/1999 | McCulloh et al. |
| 5,881,725 A | 3/1999 | Hoffman et al. |
| 5,893,275 A | 4/1999 | Henry |
| 5,979,440 A | 11/1999 | Honkonen et al. |
| 5,988,165 A | 11/1999 | Richey, II et al. |
| 6,212,904 B1 | 4/2001 | Arkharov et al. |
| 6,302,107 B1 | 10/2001 | Richey, II et al. |
| 6,314,957 B1 | 11/2001 | Boissin et al. |
| 6,446,630 B1 | 9/2002 | Todd, Jr. |
| 6,484,721 B1 | 11/2002 | Bliss |
| 6,486,874 B1 * | 11/2002 | Muthuswamy et al. ...... 345/173 |
| 6,520,176 B1 | 2/2003 | Dubois et al. |
| 6,568,391 B1 | 5/2003 | Tatarek et al. |
| 6,651,653 B1 | 11/2003 | Honkonen et al. |
| 6,681,764 B1 * | 1/2004 | Honkonen et al. ....... 128/201.21 |

(Continued)

FOREIGN PATENT DOCUMENTS

EP 0 247 365 A2 4/1987

*Primary Examiner* — Kumar Patel
*Assistant Examiner* — Vinh Lam
(74) *Attorney, Agent, or Firm* — Michael W. Haas

(57) ABSTRACT

A user interface for a portable oxygen concentration system. The user interface includes a touch screen and a controller coupled to the touch screen. The controller is configured to detect when a first portion of the touch screen is contacted by a user, and thereafter operate the touch screen for displaying an icon on a second portion of the touch screen.

18 Claims, 40 Drawing Sheets

(56) References Cited

U.S. PATENT DOCUMENTS

| | | |
|---|---|---|
| 6,698,423 B1 | 3/2004 | Honkonen et al. |
| 6,752,152 B2 | 6/2004 | Gale et al. |
| 6,764,534 B2 | 7/2004 | McCombs et al. |
| 6,889,726 B2 | 5/2005 | Richey, II et al. |
| 6,904,913 B2 | 6/2005 | Aylsworth et al. |
| 6,923,180 B2 | 8/2005 | Richey, II et al. |
| 6,949,133 B2* | 9/2005 | McCombs et al. ............... 96/111 |
| 2002/0002326 A1* | 1/2002 | Causey et al. ................. 600/300 |
| 2003/0150455 A1 | 8/2003 | Bliss et al. |
| 2006/0189877 A1* | 8/2006 | Kalgren et al. ............... 600/523 |
| 2006/0229557 A1* | 10/2006 | Fathallah et al. ............. 604/131 |
| 2006/0238517 A1* | 10/2006 | King et al. ..................... 345/173 |
| 2006/0256091 A1* | 11/2006 | Hino .............................. 345/173 |
| 2006/0258929 A1* | 11/2006 | Goode et al. .................. 600/345 |
| 2006/0284852 A1* | 12/2006 | Hofmeister et al. .......... 345/173 |
| 2007/0075978 A1* | 4/2007 | Chung .......................... 345/173 |
| 2007/0157094 A1* | 7/2007 | Lemay et al. ................. 715/717 |
| 2007/0229457 A1* | 10/2007 | Sakurai ......................... 345/157 |
| 2007/0236468 A1* | 10/2007 | Tuli ............................... 345/173 |
| 2008/0307353 A1* | 12/2008 | Molducci et al. ............. 715/802 |

\* cited by examiner

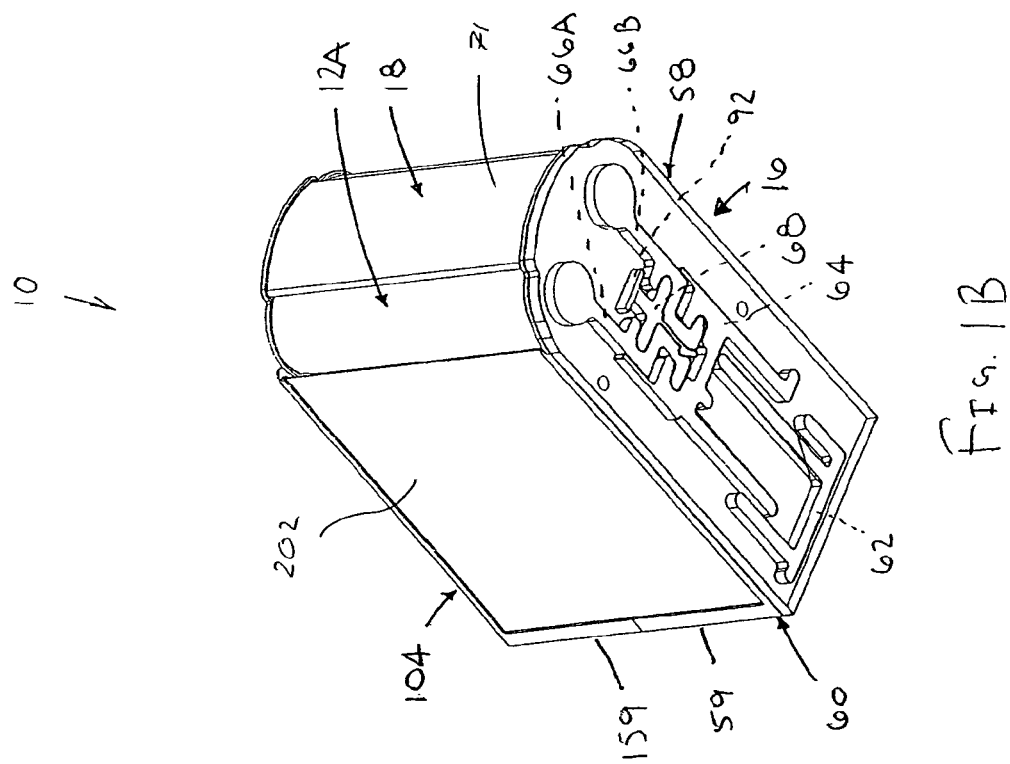

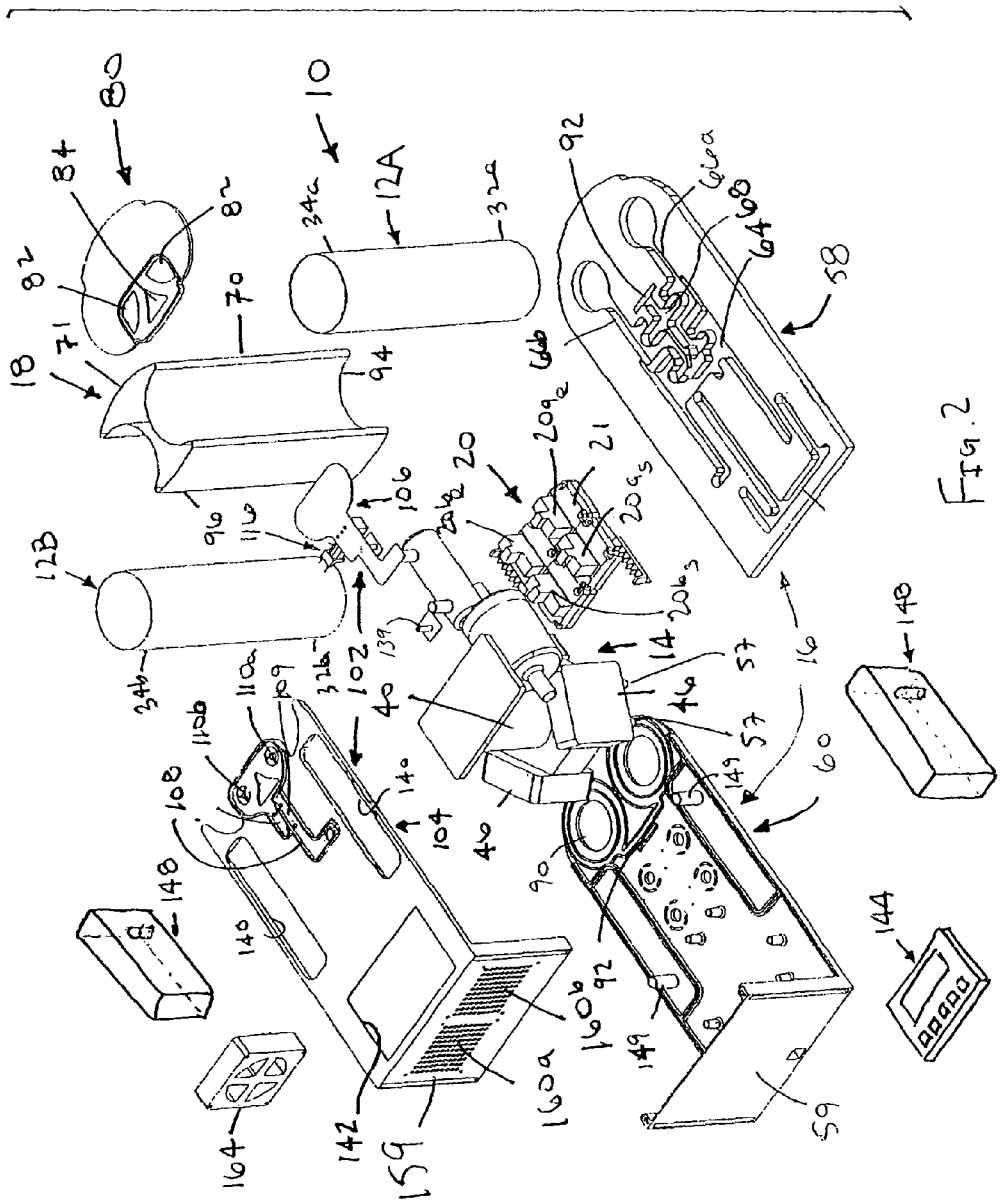

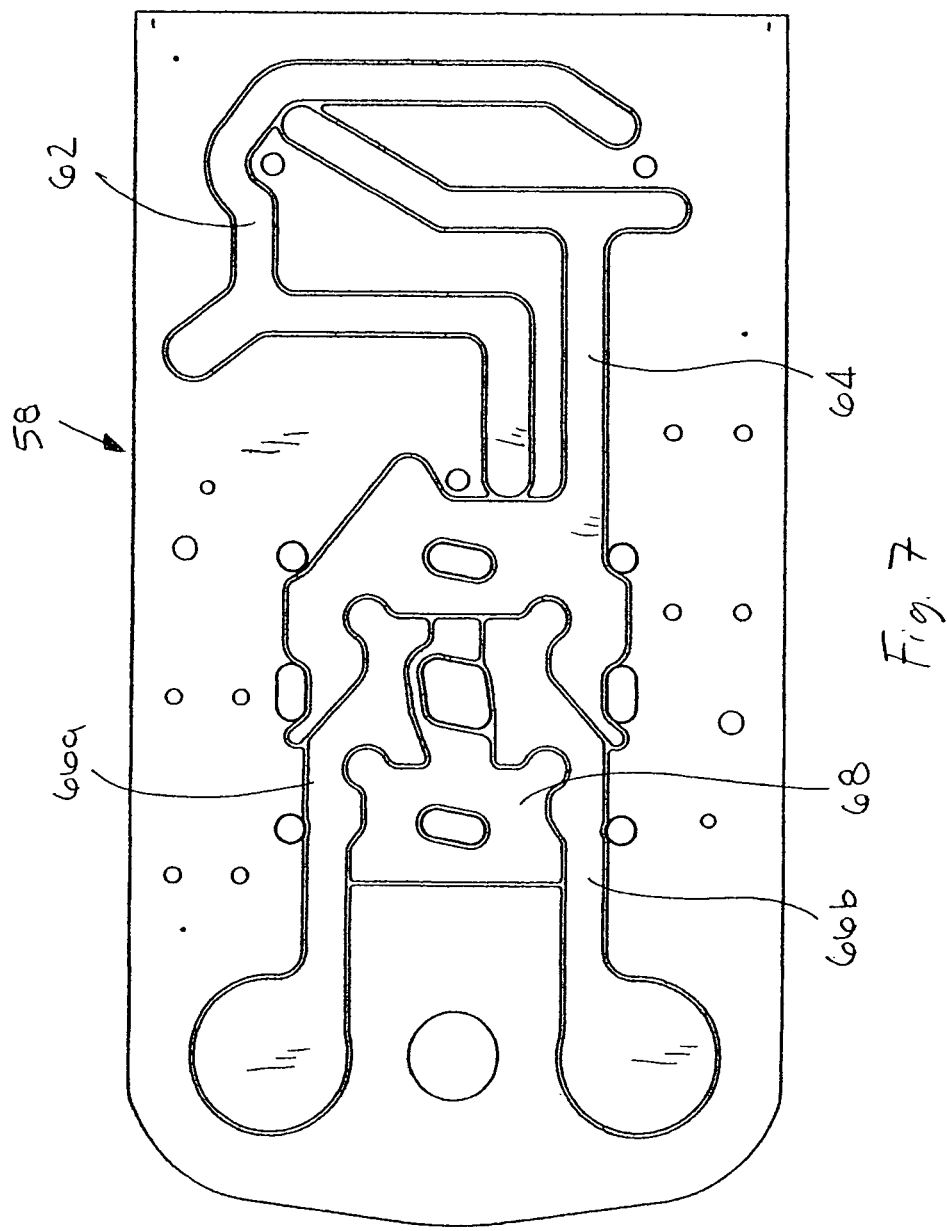

Setting 4.5

| Time PM | Servomex | Barometer | Adj O2% | V | A | Valve Gain | Pulse mL | Total mv | MV O2 | Watts | All W/lpm | Comp Only W/lpm |
|---|---|---|---|---|---|---|---|---|---|---|---|---|
| 8:41 | 84.4 | 1011 | 83.9 | 18.1 | 2.44 | 1025 | 68 | 1360 | 1083 | 44.2 | 40.3 | 35.1 |
| 8:28 | 86.7 | 1010 | 86.3 | 18.1 | 2.43 | 975 | 64 | 1280 | 1058 | 44.0 | 41.2 | 35.9 |
| 8:09 | 87.9 | 1010 | 87.5 | 18.1 | 2.43 | 925 | 61 | 1220 | 1026 | 44.0 | 42.5 | 37.0 |
| 7:51 | 89.9 | 1010 | 89.5 | 18.1 | 2.35 | 875 | 57.5 | 1150 | 996 | 42.5 | 43.8 | 38.1 |
| 7:26 | 90.9 | 1008 | 90.6 | 18.1 | 2.37 | 825 | 54 | 1080 | 952 | 42.9 | 45.8 | 39.9 |
| 6:51 | 92.1 | 1008 | 91.8 | 18.1 | 2.35 | 775 | 51 | 1020 | 914 | 42.5 | 47.7 | 41.6 |
| 4:40 | 92.7 | 1006 | 92.6 | 18.1 | 2.51 | 725 | 47.5 | 950 | 861 | 45.4 | 50.6 | 44.1 |
| 9:15 | 94.1 | 1011 | 93.5 | 18.1 | 2.39 | 650 | 43 | 860 | 790 | 43.3 | 55.2 | 48.1 |
| | | | | | | | | | Average Power | 43.6 | | |

Setting 3

| Time PM | Servomex | Barometer | Adj O2% | V | A | Valve Gain | Pulse mL | Total mv | MV O2 | Watts | All W/lpm | Comp Only W/lpm |
|---|---|---|---|---|---|---|---|---|---|---|---|---|
| 10:34 | 83.8 | 1012 | 83.2 | 18.1 | 1.63 | 1075 | 48 | 960 | 756 | 29.5 | 39.0 | 31.6 |
| 10:18 | 87 | 1012 | 86.4 | 18.1 | 1.65 | 975 | 44 | 880 | 728 | 29.9 | 40.5 | 32.8 |
| 10:01 | 89.7 | 1012 | 89.1 | 18.1 | 1.63 | 875 | 40 | 800 | 689 | 29.5 | 42.8 | 34.7 |
| 9:45 | 92.3 | 1012 | 91.7 | 18.1 | 1.63 | 775 | 35 | 700 | 626 | 29.5 | 47.1 | 38.2 |
| 9:30 | 94 | 1012 | 93.3 | 18.1 | 1.61 | 650 | 29 | 580 | 531 | 29.1 | 55.5 | 45.0 |
| | | | | | | | | | Average Power | 29.5 | | |

Setting 2

| Time PM | Servomex | Barometer | Adj O2% | V | A | Valve Gain | Pulse mL | Total mv | MV O2 | Watts | All W/lpm | Comp Only W/lpm |
|---|---|---|---|---|---|---|---|---|---|---|---|---|
| 10:29 | 83.4 | 1019 | 82.3 | 18.1 | 1.25 | 1100 | 33 | 660 | 521 | 22.6 | 42.9 | 32.1 |
| 10:12 | 86.9 | 1019 | 85.7 | 18.1 | 1.24 | 1000 | 30.5 | 610 | 509 | 22.4 | 43.9 | 32.9 |
| 9:55 | 89.55 | 1019 | 88.3 | 18.1 | 1.25 | 900 | 27.3 | 546 | 474 | 22.6 | 47.2 | 35.4 |
| 9:12 | 91.3 | 1018 | 90.1 | 18.1 | 1.22 | 800 | 24 | 480 | 427 | 22.1 | 52.3 | 39.2 |
| 8:26 | 92.2 | 1017 | 91.1 | 18.1 | 1.27 | 725 | 22 | 440 | 397 | 23.0 | 56.4 | 42.2 |
| 6:20 | 92.9 | 1020 | 91.5 | 18.1 | 1.2 | 650 | 19.7 | 394 | 359 | 21.7 | 62.3 | 46.7 |
| 6:53 | 93.3 | 1020 | 91.9 | 18.1 | | 575 | 17.6 | 352 | 322 | | 69.4 | 52.0 |
| | | | | | | | | | Average Power | 22.4 | | |

FIG. 16

| ICON | NAME |
|---|---|
| NB | NO BREATH ALARM |
| O2 | OXYGEN CONCENTRATION ALARM |
| HR | HIGH BREATH RATE ALARM |
| TF | TECHNICAL FAULT/ GENERAL MALFUNCTION ALARM |
| (audible alarm icon) | AUDIBLE ALARM ICON |
| (alarm silence icon) | ALARM SILENCE ICON |
| (battery icon, Flashing) | BATTERY LOW ALARM |
| (battery X icon, Flashing) | BATTERY DEPLETED ALARM |
| MX | BREATH RATE ALARM |
| (triangle icon) | TECHNICAL FAULT ALARM |
| (power connection icon) | POWER CONNECTION SYMBOL |
| (attention triangle icon) | ATTENTION ALARM |
| (pulse icon) | PULSE SYMBOL |

FIG. 33

|  | AirSep Lifestyle | Inogen | SeQual | AirSep Freestyle | Present Invention |
|---|---|---|---|---|---|
| Runtime - setting of 2 @ 20 breaths per minute | 50 minutes | 3 hours | 2 hours (approx) | 2.5 hours (6 hours w/ battery belt) | 8 hours |
| Maximum flow @ 100% O₂ equivalence | 0.6 lpm est. (based on testing) | 0.65 lpm (based on 0.75 lpm adjusted for 90% O₂) | 2.65 lpm (based on 3.0 lpm adjusted for 90% O₂) | 0.36 (estimated based on max setting of 3 vs. 5 on the Lifestyle) | 0.90 lpm |
| Weight | 9.8 lbs | 9.7 lbs | 17.4 lbs | 4.4 lbs (6.2 lbs w/ battery belt) | 9.8 - 10 lbs |
| Sound | less than 55 dB | 35.2 dB | 48 dB | less than 55 dB | 57 dB or less |
| Overall size | 5.5 ix 7.25 x 16.31 inches (650 in³) | 11.62 x 6.00 x 12.39 inches (863 in³) | 19.3 x 12.3 x 7.1 inches (1,685 in³) | 8.6 x 6.1 x 3.6 inches (188 in³) | 12 x 6 x 8.5 inches (612 in³) |
| Life of the Compressor | unknown | unknown | unknown | unknown | 6000 hours |

FIG. 34

| Settings | Minute Vol | O2 Concentration | | Bolus | Sound dBA | Power | Battery run time | |
|---|---|---|---|---|---|---|---|---|
|  | ml O₂ / min | % Min | % Max | ml / breath | Max dB(A) | Watts | Maximum (hours) | Nominal (hours) |
| 1 pulse | 200 | 86.0 | 93.0 | 11.8 | 48 | 16.8 | 13.80 | 10.7 |
| 2 pulse | 400 | 86.0 | 93.0 | 23.6 | 50 | 22.5 | 10.20 | 8.0 |
| 3 pulse | 600 | 86.0 | 93.0 | 35.4 | 52 | 30.0 | 7.80 | 6.0 |
| 4 pulse | 800 | 86.0 | 93.0 | 47.2 | 57 | 38.3 | 6.00 | 4.7 |
| 5 pulse | 900 | 86.0 | 93.0 | 59 | 57 | 45.0 | 5.10 | 4.0 |
| 6 pulse | 900 | 86.0 | 93.0 | 70.8 | 57 | 45.0 | 5.10 | 4.0 |

FIG. 35

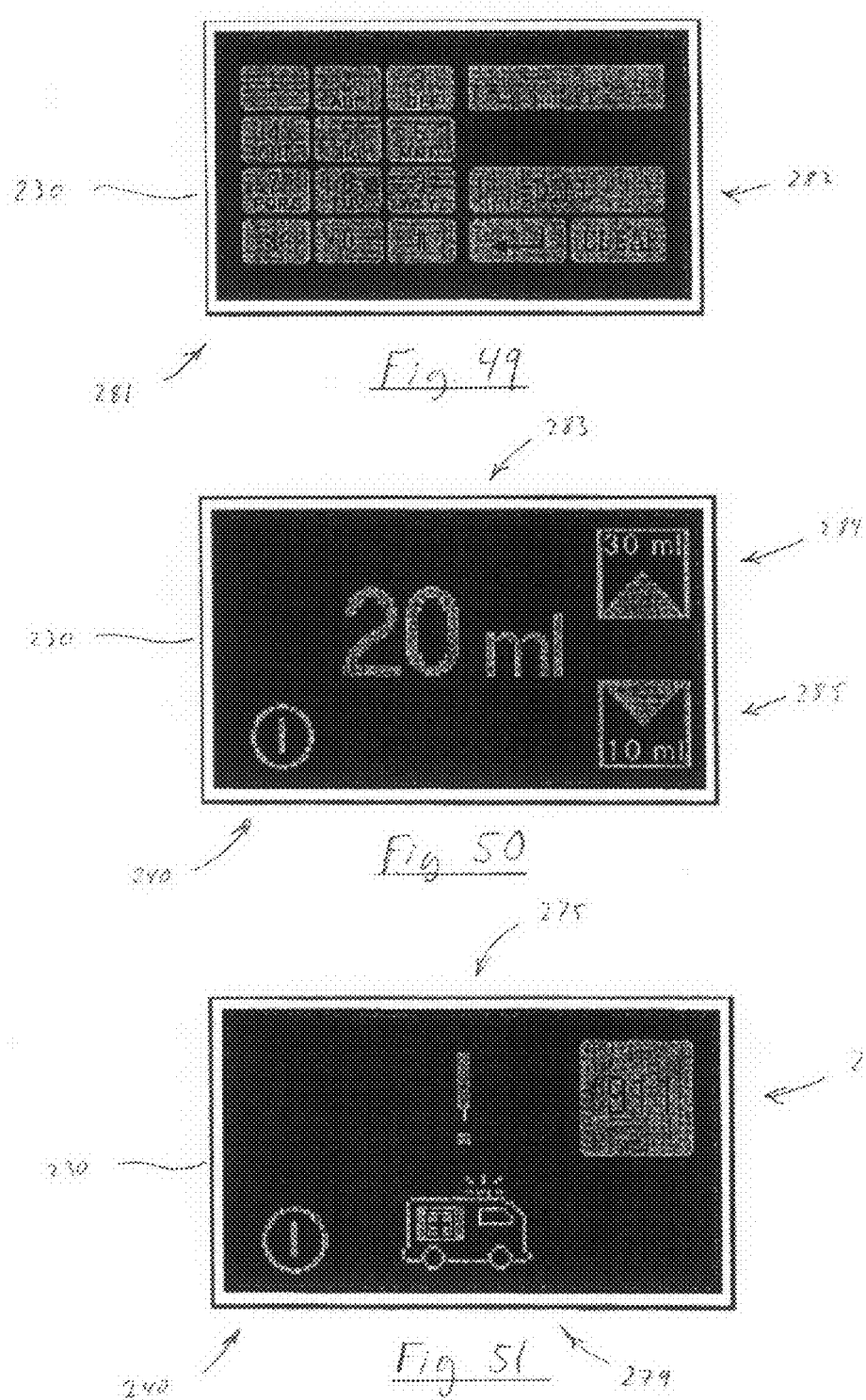

USER INTERFACE FOR A PORTABLE OXYGEN CONCENTRATOR

CROSS-REFERENCE TO RELATED APPLICATIONS

This application claims priority under 35 U.S.C. §119(e) from provisional U.S. patent application Nos. 60/788,916, filed Apr. 3, 2006; 60/744,196, filed Apr. 3, 2006; 60/744,197 filed Apr. 3, 2006; 60/744,271, filed Apr. 4, 2006; and 60/744,272, filed Apr. 4, 2006, the contents of each of which are incorporated herein by reference.

FIELD OF THE INVENTION

The present invention relates generally a user interface for a portable device, e.g., a portable oxygen concentrator, and, more particularly to a touch screen for a portable oxygen concentrator or other portable devices, and to a method for using such a user interface.

DESCRIPTION OF THE RELATED ART

Lung diseased patients often need supplemental oxygen to improve their comfort and/or quality of life. Stationary sources of oxygen are available, e.g., oxygen lines in hospitals or other facilities, that may provide oxygen to patients. To allow some mobility, cylinders of pure and/or concentrated oxygen can be provided that a patient may carry or otherwise take with them, e.g., on pull-along carts. Such cylinders, however, have limited volume and are large and heavy, limiting the patient's mobility.

Portable devices have been suggested that concentrate oxygen from ambient air to provide supplemental oxygen. For example, pressure swing adsorption ("PSA") apparatus are known that separate nitrogen from ambient air, delivering a stream of concentrated oxygen that may be stored in a tank or delivered directly to patients. For example, U.S. Pat. Nos. 5,531,807; 6,520,176; and 6,764,534 disclose portable PSA oxygen concentrators. Accordingly, apparatus and methods for providing oxygen would be useful.

SUMMARY OF THE INVENTION

Accordingly, it is an object of the present invention to provide a user interface for portable oxygen concentration system that includes a touch screen and a controller coupled to the touch screen. The controller is configured to detect when a first portion of the touch screen is contacted by a user, and thereafter operate the touch screen for displaying an icon on a second portion of the touch screen.

It is a further object of the present invention to provide an oxygen concentrator that includes such a user interface.

It is a still further object to provide a method for operating an electronic device that includes contacting a first portion of a touch screen, whereupon an icon is displayed on a second portion of the touch screen. The method further includes contacting the second portion of the touch screen to change an operation state of the device. In an exemplary embodiment, the electronic device is an oxygen concentrator.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 1A and 1B are top and bottom perspective views, respectively, of a first embodiment of a portable oxygen concentrator apparatus according to the principles of the present invention;

FIG. 7 is a top view of a manifold base that defines part of an air manifold in the apparatus of FIGS. 1A and 1B;

FIG. 16 is a table of various performance criteria of the portable oxygen concentrator of the present invention at different flow rate settings;

FIG. 20 is chart illustrating the relationship between the minute volume and the Target Pressure;

FIG. 33 is a table of the various alarm icons capable of being displayed on the user interface;

FIG. 34 is a chart comparing the portable oxygen concentrator of the present invention to existing devices;

FIG. 35 is a chart showing various parameters of the apparatus of the present invention at different flow settings;

FIGS. 46-53 illustrate additional images that may be displayed on the touch screen user interface used in the apparatus of the present invention.

DETAILED DESCRIPTION OF THE EXEMPLARY EMBODIMENTS

Figure 1A:
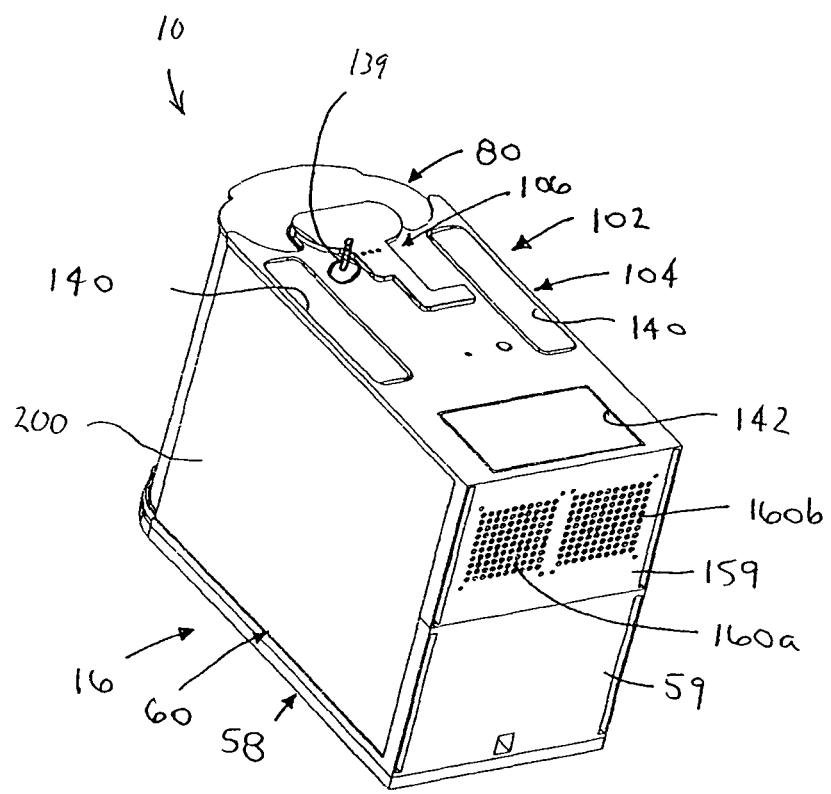

FIGS. 1A-3 illustrate a portable oxygen concentrator apparatus 10 according to the principles of the present invention. Generally, apparatus 10 includes a plurality of sieve beds or tanks 12A, 12B, a compressor 14, a lower or air manifold 16 defining a plurality of passages 62-68 therein, a storage tank or reservoir 18, a set of air control valves 20 for creating one or more flow paths through the passages 62-68 within the air manifold 16, and an upper or oxygen delivery manifold 102. A controller 22 is coupled to the air control valves 20 to selectively open and close the air control valves to control airflow through the air manifold 16, and, consequently, through the sieve beds 12. Controller 22 is also coupled to an input/output device 23 that is used, for example, to set the operating parameters, such as the oxygen flow rate, of the apparatus.

It should be noted that the air control valves are collectively referred to using reference number 20, and are individually designated as valves $20a_e$, $20a_s$, $20b_e$, $20b_s$. Likewise, the sieve beds are collectively referred to using reference numeral 12, and are individually designated as sieve beds 12A and 12B. It should also be noted that controller 22 is shown in communication with the various elements of apparatus 10 via dashed lines, and that only one dashed line is shown between controller 22 and valve $20b_s$ for ease of illustration. In the actual device, controller 22 is in communication with each air control valve.

Optionally, apparatus 10 may include one or more additional components, e.g., one or more check valves, filters, sensors, electrical power sources (not shown), and/or other components, at least some of which may be coupled to controller 22 (and/or one or more additional controllers, also not shown), as described further below. It will be appreciated that the terms "airflow", "air", or "gas" are used generically herein, even though the particular fluid involved may be ambient air, pressurized nitrogen, concentrated oxygen, and the like.

A. Sieve Beds

Figure 4:
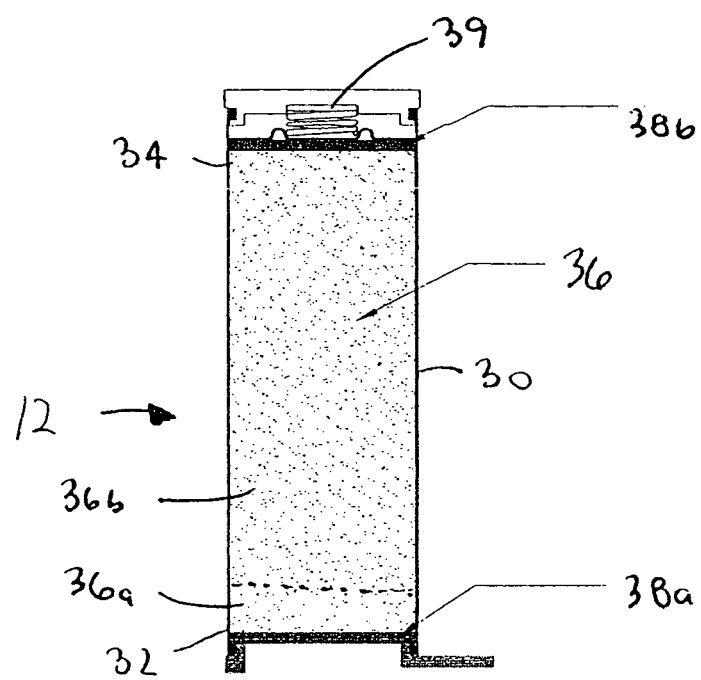
FIG. 4 is a cross-section of an exemplary sieve bed suitable for use in the apparatus of FIGS. 1A and 1B.

Turning now to FIG. 4, each sieve bed 12A or 12B includes an outer casing 30, e.g., in the shape of an elongate hollow cylinder, including a first or air inlet/outlet end 32 and a second or oxygen inlet/outlet end 34. Casing 30 may be formed from substantially rigid material, e.g., plastic, such as acrylonitrile butadiene styene ("ABS"), polycarbonate, and the like, metal, such as aluminum, or composite materials. In exemplary embodiments, casing 30 may have a diameter between about two and ten centimeters (2-10 cm), and a length between about eight and thirty centimeters (8-30 cm). Although casing 30 is shown having a round cylindrical shape, it will be appreciated that the casing may have other desired shapes, e.g., that may depend upon spatial, performance, and/or structural criteria. For example, casing 30 may have an elliptical, square, rectangular, or other regular or irregular polygonal shaped cross-section (not shown).

Casing 30 is at least partially filled with a filtration media or sieve material 36 to provide a sieve bed 12A, 12B capable of adsorbing nitrogen from air delivered into the sieve bed under pressure. To hold sieve material 36 within casing 30, the sieve bed includes discs or plates 38a and 38b adjacent each of the first and second ends 32, 34 of the casing, respectively. Plates 38a and 38b are spaced apart from one another to define a desired volume between the plates 3 within casing 30. For example, the desired volume may be between about one hundred fifty and six hundred cubic centimeters (150-600 $cm^3$), which may be filled with sieve material 36. In an exemplary embodiment, the volume of sieve material 36 within each sieve bed 12A, 12B is about forty four cubic inches (44 $in^3$), as explained further below.

Plates 38 may include one or more openings or pores (not shown) therethrough to allow airflow through the plates. For example, the plates may be formed from sintered plastic, thereby providing pores within the plastic material that are smaller than the grain size of sieve material 36, thereby allowing airflow though the plates. Alternatively, plates 38 may be formed from plastic, metal, or composite materials having multiple holes or pores formed therethrough. For example, the holes may be created when the plates are formed, e.g., by molding the plates and holes simultaneously. In another alternative, plates 38 may be formed as solid panels, e.g., cut from stock, molded, etc., and the holes may be created through the panels, e.g., by drilling, laser cutting, and the like.

Generally, sieve beds 12 are filled such that there are no substantial voids in sieve material 36, e.g., such that the sieve material is substantially packed between plates 38. The resulting sieve bed, which includes the components shown in FIG. 4 only, weighs between about 0.25-1.50 pounds each.

In the embodiment shown, lower plate 38a is substantially stationary, e.g., fixed to first end 32 of casing 30, e.g., by one or more cooperating connectors or fasteners (not shown), adhesives, sonic welding, and the like. Upper plate 38b is disposed adjacent second end 34, yet movable within casing 30. For example, the present invention contemplated biasing upper plate 38b toward lower plate 38a, e.g., by a spring or other biasing mechanism 39, which compresses sieve material 36 between plates 38. If sieve material 36 settles or somehow escapes from sieve bed 12A, 12B, upper plate 38b automatically moves downwardly towards lower plate 38a to maintain the sieve material under a desired compression. This compression prevents sieve material 36 from moving into other areas of apparatus 10 when it has become powderized from operation and/or may counteract flow-induced forces that may otherwise cause the sieve material to fluidize.

The porosity of plates 38 may be substantially uniform across the cross-section of a sieve bed 12, e.g., to ensure that flow into and/or out of the sieve bed is substantially evenly distributed across the area of first and second ends 32, 34. Alternatively, the porosity of plates 38 may be varied in a desired pattern or only a portion of the plates may be porous. In yet another alternative, plates 38 may have a solid wall and may include one or more openings therethrough, e.g., in a desired pattern.

Sieve material 36 may include one or more known materials capable of adsorbing nitrogen from pressurized ambient air, thereby allowing oxygen to be bled off or otherwise evacuated from sieve beds 12. Exemplary sieve materials suitable for use herein include synthetic zeolite, LiX, and the like, such as UOP Oxysiv 5, 5A, Oxysiv MDX, Arkema N5, N51, or Zeochem ZI0-06. It may be desirable to provide multiple layers of sieve material 36 within each sieve bed 12A, 12B, e.g., providing sieve material with different properties in layers between first end 32 and second end 34.

For example, because sieve material generally absorbs water, which may cause some sieve material to deteriorate, sieve material may be provided at first end 32 that is capable of absorbing water without substantially impacting its durability and/or ability to adsorb nitrogen. In an exemplary embodiment, a first layer 36a is provided adjacent first end 32 having a depth, which is a dimension that is parallel to the length of the sieve beds, that is between about ten and thirty percent of the overall height of sieve material, such as Oxysiv material. A second layer 36b is provided that includes a high performance adsorption material, such as Oxysiv MDX. Second layer 36b may substantially fill the remainder of the sieve bed. Of course, one or more additional layers of sieve material may be provided (not shown) having desired properties. Thus, during use, when ambient air enters first end 32 of sieve bed 12A, 12B, first layer 36a substantially absorbs moisture in the air, such that second layer 36b is exposed to relatively dry air, thereby substantially reducing the risk of damaging the sieve material of second layer 36b. It has been determined for Oxysiv MDX that between about 0.5-1.5 pounds, and preferably about one pound, of the sieve material per liter per minute (lpm) outlet production provides efficient adsorption.

Although two sieve beds 12A and 12B are shown in the figures, it will be appreciated that one or more sieve beds may be provided, e.g., depending upon the desired weight, performance efficiency, and the like. Additional information on sieve beds and/or sieve materials that may be included in apparatus 10 may be found in U.S. Pat. No. 4,859,217, the entire disclosure of which is expressly incorporated by reference herein.

B. Gas Storage Reservoir and Sieve Assembly

Returning to FIGS. 1A, 1B, and 2, reservoir 18 is an elongate tubular casing 70 having a lower or first end 94, which may be substantially enclosed or open, and an upper or second end 96, which may also be substantially enclosed or open (e.g., if capped by a manifold or other component, as described elsewhere herein). As shown, casing 70 has an irregular hourglass shape allowing reservoir 18 to be nested between and/or adjacent to sieve beds 12A and 12B. This minimizes the space occupied by reservoir 18 to help reduce the overall size of apparatus 10. In the illustrated exemplary embodiment, casing 70 has a curved outer wall 71 that extends between sieve beds 12A, 12B to provide or define a finished outer surface for the apparatus 10, as best seen in FIGS. 1A and 1B. Casing 70 is formed from any suitable material. Examples of such materials include plastic, such as ABS, polycarbonate, and the like, metal, such as aluminum, or composite materials, similar to the other components of apparatus 10 described herein.

As shown in FIGS. 2 and 10A-10C, the present invention contemplates providing a cap 80 to at least partially close upper end 96 of casing 70. Cap 80 may be substantially permanently or removably attached to second ends 34 of sieve beds 12A, 12B and/or upper end 96 of reservoir 18, e.g., using one or more connectors, fasteners, adhesives, sonic welding, and the like. Cap 80 includes one or more openings 82, 84 therein for allowing oxygen to flow into and out of sieve beds 12A, 12B and/or reservoir 18, as explained further below.

Figure 10A:
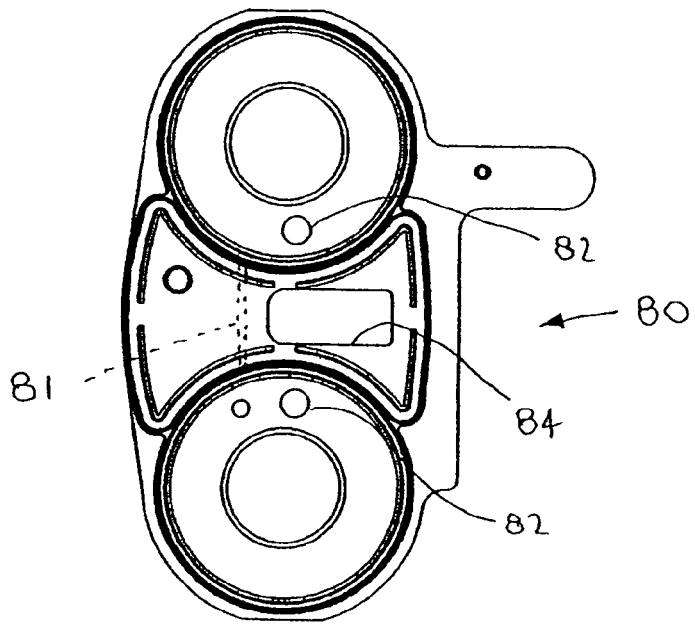
FIGS. 10A-10C are bottom, side, and top views, respectively, of a sieve bed cap that defines part of the apparatus of FIGS. 1A and 1B.
Figure 10B:
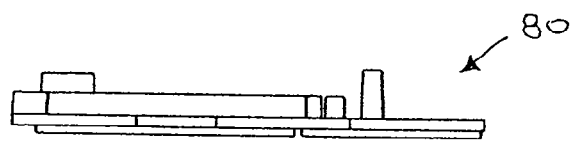
Figure 10C:
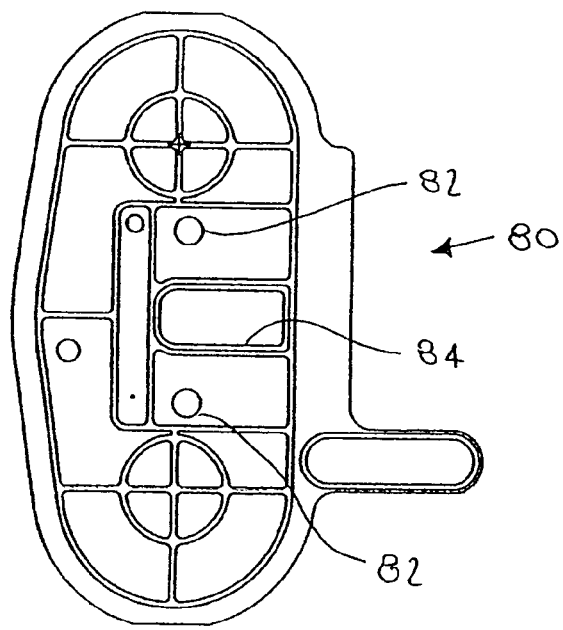

Turning to FIG. 10A, cap 80 includes a purge orifice 81 (shown in phantom) to provide a passage communicating directly between seconds ends 34 of sieve beds 12A and 12B. Purge orifice 81 remains continuously open, thereby providing a passage for oxygen to pass from one sieve bed to the other, e.g., while the one sieve bed is charging and the other is purging, as described further below. In an exemplary embodiment, purge orifice 81 has a precisely determined cross-sectional size, e.g., between about 0.015-0.35 inch, or about 0.020 inch diameter, that is determined based upon one or more flow or other performance criteria of the sieve beds 12A, 12B, as explained further below. For example, purge orifice 81 is sized such that between about two and a half and ten liters per minute (1.5-10 lpm) of oxygen, e.g., about five liters per minute (5 lpm), flows through purge orifice 81 in either direction at a pressure differential of about five pounds per square inch (5 psi) across the purge orifice.

The present invention also contemplates providing a purge valve (not shown) in purge orifice 81 to control the flow of gas between the sieve beds. Such a purge valve has the effect of varying the purge orifice flow as the beds are alternately charged and purged.

Alternatively, the purge orifice may extend between sieve beds 12A and 12B via reservoir 18. For example, the purge orifice may include a first passage (not shown) extending along cap 80 that communicates between sieve bed 12A and reservoir 18, and a second passage (also not shown) extending along cap 80 that communicates between sieve bed 12B and reservoir 18.

Optionally, if lower end 94 of casing 70 is open, a cap (not shown) may also be provided for substantially closing the lower end of the casing. Such a cap, if provided, may be substantially permanently or removably attached to the lower end of the casing. Alternatively, the present invention contemplates enclosing lower end 94 of casing 70 by a portion of air manifold 16, e.g., when reservoir 18 is mounted onto or adjacent air manifold 16, as describe further below.

In a further alternative, apparatus 10 may include multiple reservoirs (not shown) that may be provided at one or more locations with the apparatus, e.g., placed in different locations where space if available, yet minimizing the overall size of the apparatus. The present invention contemplates that the reservoirs are connected to one another via one or more flexible tubes (not shown) and/or via oxygen delivery manifold 102 to allow oxygen to be delivered to and withdrawn from the reservoirs. Optionally, in this alternative, one or more valves may be provided for controlling flow of oxygen into and out of the reservoirs.

In addition or alternatively, apparatus 10 may include one or more flexible reservoirs, e.g., bags or other containers that may expand or contract as oxygen is delivered into or out of them. The reservoirs may have predetermined shapes as they expand or more expand elastically to fill available space within apparatus 10. Optionally, one or more rigid reservoirs may be provided that communicate with one or more flexible reservoirs (not shown), e.g., to conserve space within the apparatus. In further alternatives, one or more reservoirs may be provided as portions of one or both of air manifold 16 and oxygen delivery manifold 102, rather than as a separate component.

C. Gas Compressor

Figure 5A:
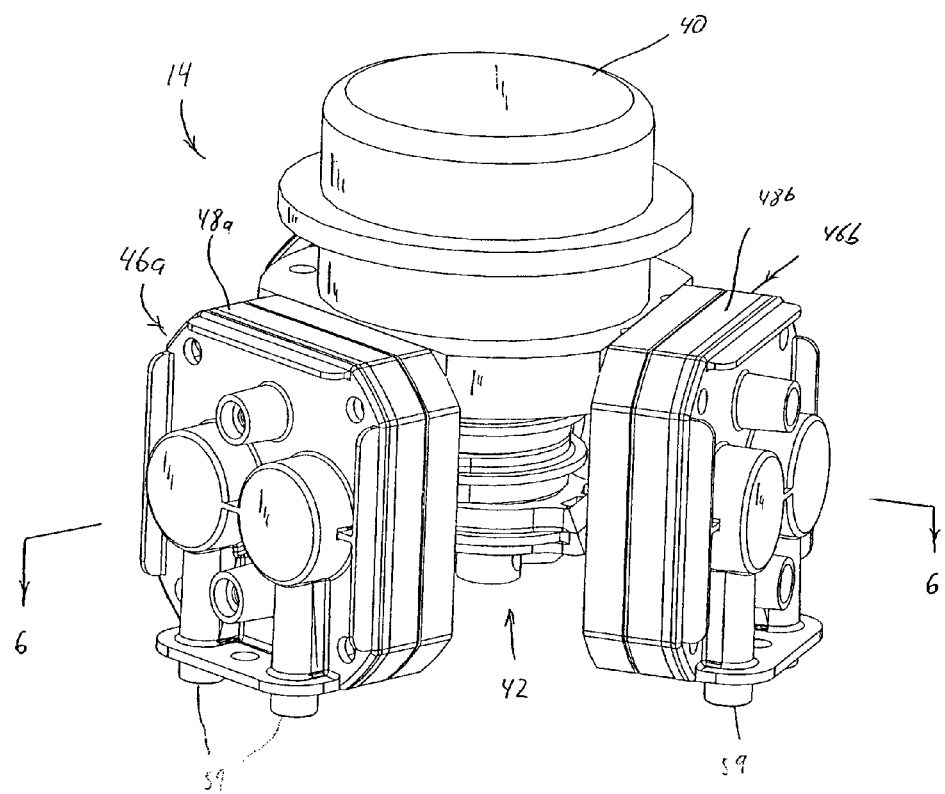
FIGS. 5A, 5B, and 5C are perspective, top, and exploded views, respectively, of a compressor suitable for use in the apparatus of FIGS. 1A and 1B.
Figure 5B:
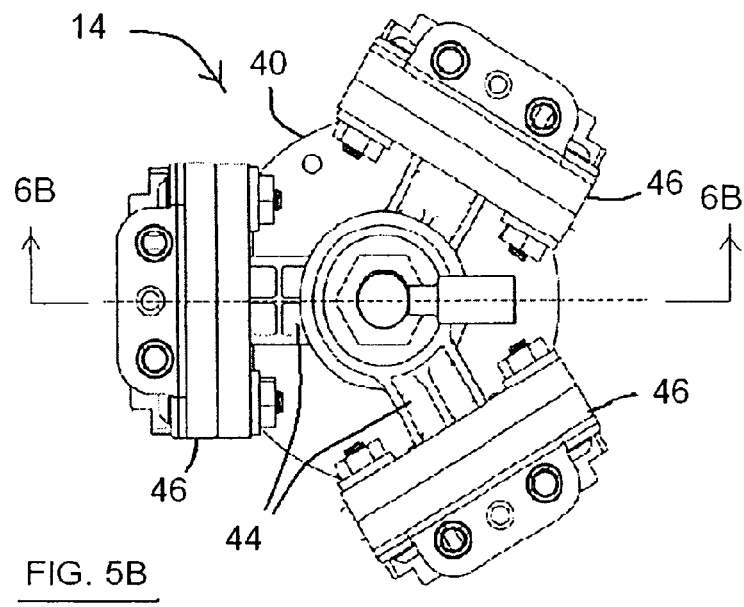
Figure 43:
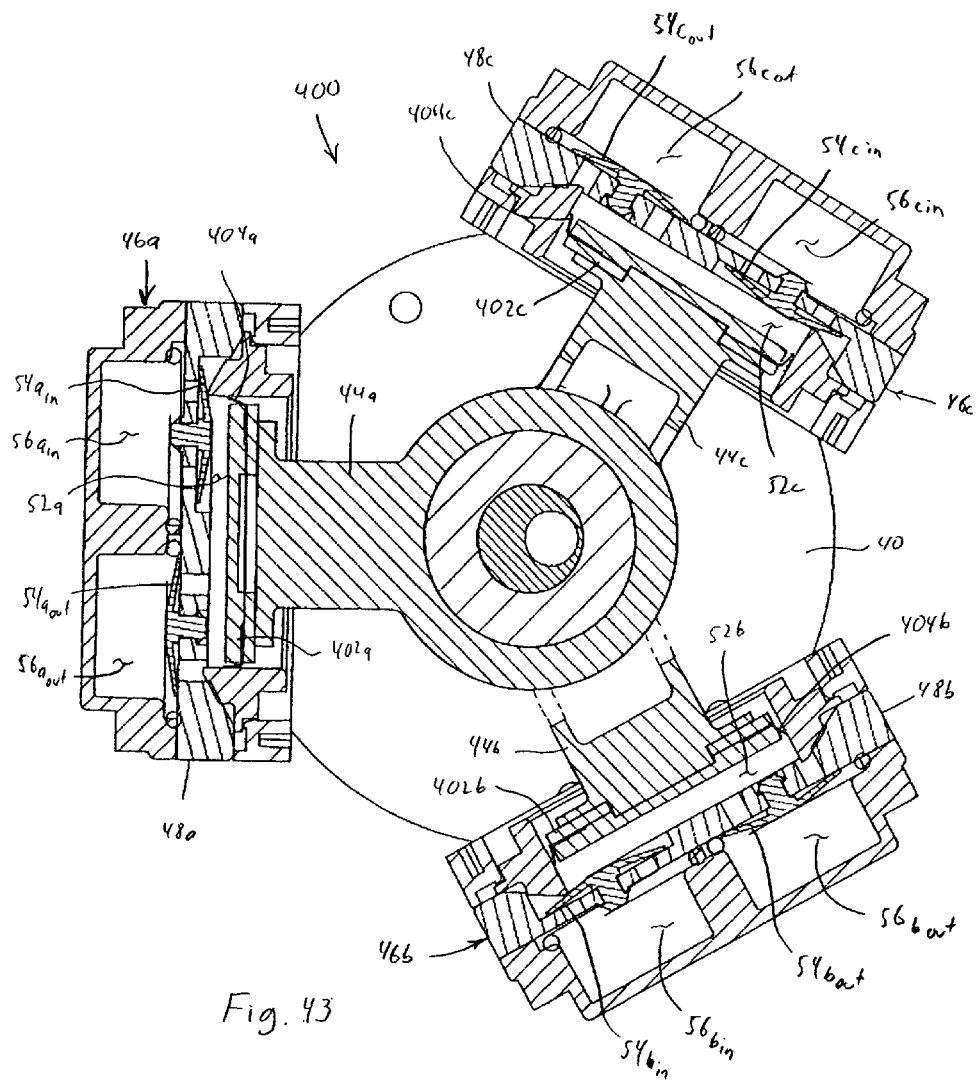
FIG. 43 is a top, cross-sectional view of a wobble-piston compressor suitable for use in the apparatus of the present invention.

Returning to FIGS. 1A, 1B, and 2, with additional reference to FIGS. 5A, 5B, and 6, an exemplary embodiment of compressor 14 suitable for use in the present invention will now be described. It is to be understood that compressor 14 can any device capable of drawing ambient air into apparatus 10 and compressing the air to one or more desired pressures for delivery to the sieve beds. Suitable compressors include, but are not limited to, articulated piston (wrist pin connecting rod to piston), diaphragm, wobble piston (piston fixed to connecting rod), scroll, linear, and rotary vane compressors. An example of a wobble piston compressor 400 suitable for use in the present invention is shown in FIG. 43.

In the embodiment shown in FIGS. 5A-6B, compressor 14 is a multiple headed device that includes a motor 40, a cam assembly 42 coupled to the motor, drive shafts or rods 44 coupled to the cam assembly, and a plurality of diaphragm assemblies or heads 46 coupled to the drive shafts. Motor 40 may be a brushless DC motor, such as the Pittman 4413, which has a relatively low weight and long operational life. Rods 44 are individually referred to using reference numerals 44a, 44b, and 44c and are collectively referred to using reference numeral 44. Similarly, heads 46 are individually referred to using reference numerals 46a, 46b, and 46c and are collectively referred to using reference numeral 46.

Motor 40 includes an output shaft 41 defining a central axis 43. Motor 40 may include a base plate, frame, or other support 45 extending from housing 47. As explained further below, support 45 may be used to secure diaphragm assemblies 46 directly to motor 40, which may reduce vibration of the diaphragm assemblies. This construction may also facilitate installation of the compressor 14 into a concentrator or other device, e.g., by allowing motor 40 and heads 46 to be preassembled and then installed as a single component.

Figure 6B:
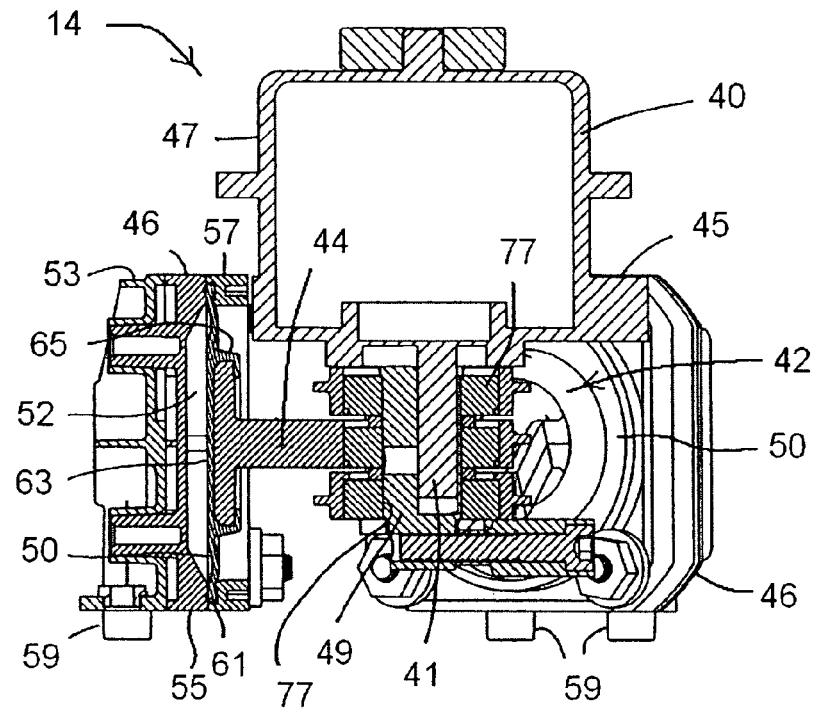
FIG. 6B is a side sectional view of the compressor taken along line 6B-6B of FIG. 5B.
Figure 5C:
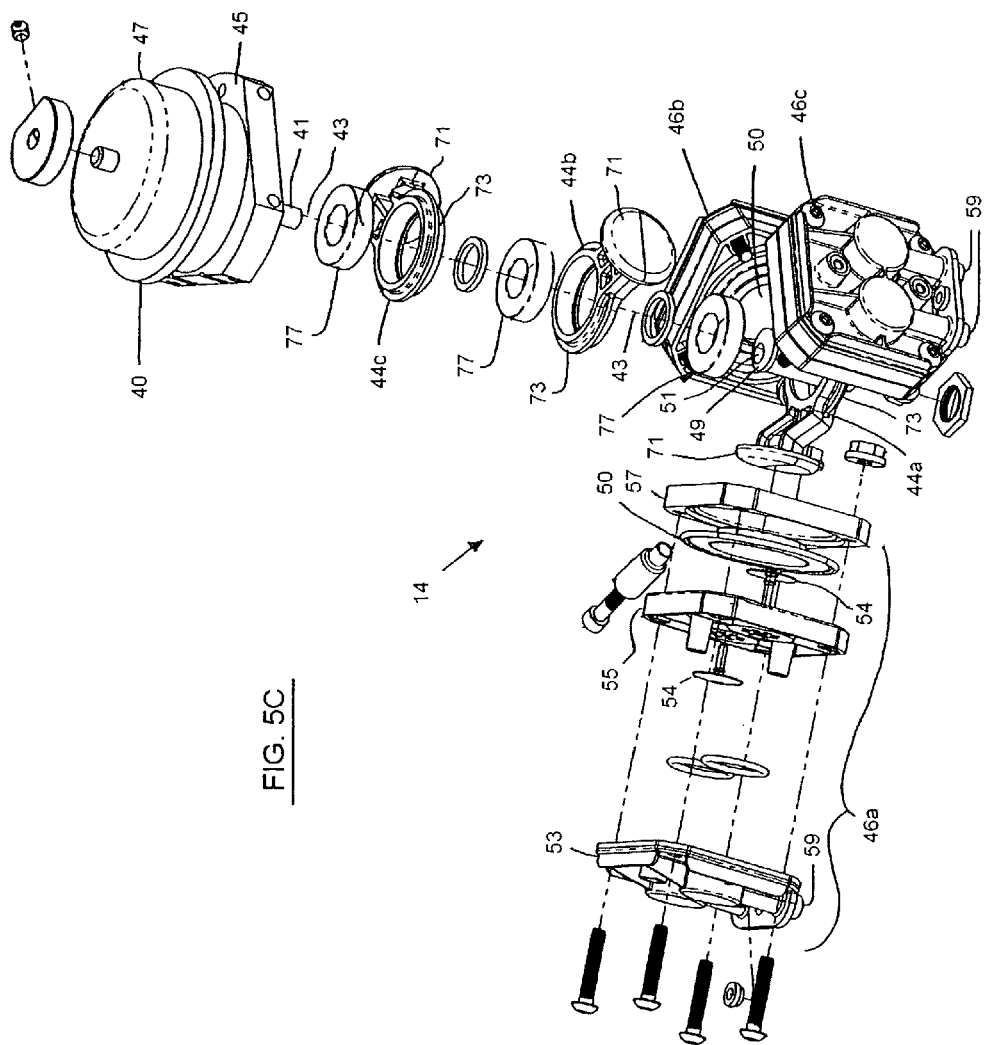

As best seen in FIG. 5C, output shaft 41 is coupled to cam assembly 42 such that rotation of the output shaft 41 causes a crankshaft 49 to rotate about central axis 43. As shown in FIGS. 5B and 6B, crankshaft 49 may be an elongate cylindrical barrel including a bore 51 in one end for receiving output shaft 41 therein. Crankshaft 49 may be secured to output shaft 41, e.g., by a mating lock and key arrangement, an interference fit, a set screw (not shown), and the like. Bore 51 may be offset from the central axis 43, such that crankshaft 49 rotates eccentrically about the central axis when output shaft 41 is rotated by motor 40. It will be appreciated that other arrangements may be provided for securing crankshaft 49 to output shaft 41.

As best seen in FIGS. 5A-6B, each diaphragm assembly 46 includes a housing 48, a diaphragm 50 secured to the housing to define a chamber 52, and a set of check valves 54 for allowing air to be drawn into and forced out of the chamber. Housing 48 may include one or more substantially rigid parts providing a support structure for diaphragm 50 and at least partially defining chamber 52. Housing 48 may be formed from plastic, such as ABS or polycarbonate, metal, or composite materials, e.g., made by molding, casting, machining, and the like.

Each of the diaphragm assembly 46 generally includes a cover 53 including inlet and outlet ports 59, a head 55 including inlet and outlet valves 254, and a retainer 57 for mounting diaphragm 50 to head 55. Diaphragm 50, head 55, and retainer 57 generally define a chamber 52 into which ambient air may be drawn and from which compressed air may be delivered on a cyclical basis, as explained elsewhere herein. With additional reference to FIGS. 44A and 44B, an outer lip or other perimeter 61 of diaphragm 50 may be secured between head 55 and retainer 57, while allowing a central portion 63 to move.

Diaphragm 50 is substantially permanently or removably attached to housing 48, e.g., using an interference fit, one or more connectors, fasteners adhesives, and the like (not shown), that may provide a substantially airtight seal between the diaphragm and the housing. Diaphragm 50 may be formed from flexible or semi-rigid material that may repeatedly deflected a desired distance during operation of the compressor 14, e.g., Ethylene Propylene Diene Monomer ("EPDM") or "BUNA" rubber (synthetic rubber made by polymerizing butadiene), and the like, VITON, or liquid silicone rubber ("LSR") materials having sufficient flexibility, resiliency, and/or other appropriate properties. Diaphragm 50 may include supports 65 for coupling diaphragm 50 to an associated rod 44.

In exemplary embodiments, housing 48 and diaphragm 50 may have square or rectangular cross-sections (extending into the page of FIG. 6), e.g., between about one and three inches (1-3 in) on a side. Housing 48 may have a depth between about 0.25-1.5 inches, thereby providing chamber 52 defining a volume. In an exemplary embodiment, diaphragm assemblies 46 have a square cross-section with each of the height and width being about two inches (50 mm). It will be appreciated, however, that housing 48 and diaphragm 50 may have other cross-sectional shapes, e.g., circular, elliptical, and the like.

Figures 44A, 44B:
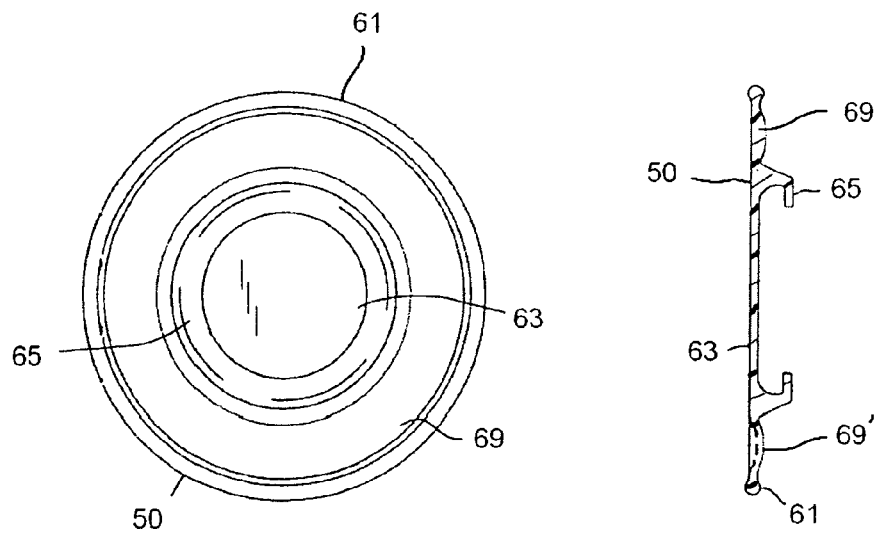
FIGS. 44A and 44B are front and side views, respectively, of a diaphragm used in the compressor of FIGS. 5A-6C.

As best seen in FIGS. 44A and 44B, diaphragm 50 may include a thicker peripheral portion 69 between outer lip 61 and central portion 63, which may enhance rigidity, and consequently efficiency, of the diaphragm assemblies. For example, the increased rigidity may limit motion of peripheral portion 69 when central portion 63 of diaphragm 50 is directed inwardly and outwardly by rod 44, as explained elsewhere herein. Alternatively, as shown in phantom at the lower portion of FIG. 44B and indicated by reference numeral 69', peripheral portion 69' may include a thickness similar or even less than central portion 63. As shown, peripheral portion 69' may also be curved or otherwise contoured, for example, to control the deflection of the diaphragm.

Diaphragm 50 is coupled to drive shaft 44 such that diaphragm 50 may move inwardly and outwardly relative to chamber 54 as the drive shaft reciprocates along its longitudinal axis away from and towards cam assembly 42. Thus, the volume of chamber 54 may be increased and decreased as diaphragm 50 moves away from and towards the chamber to draw air into and force air out of the chamber, respectively.

Figure 6A:
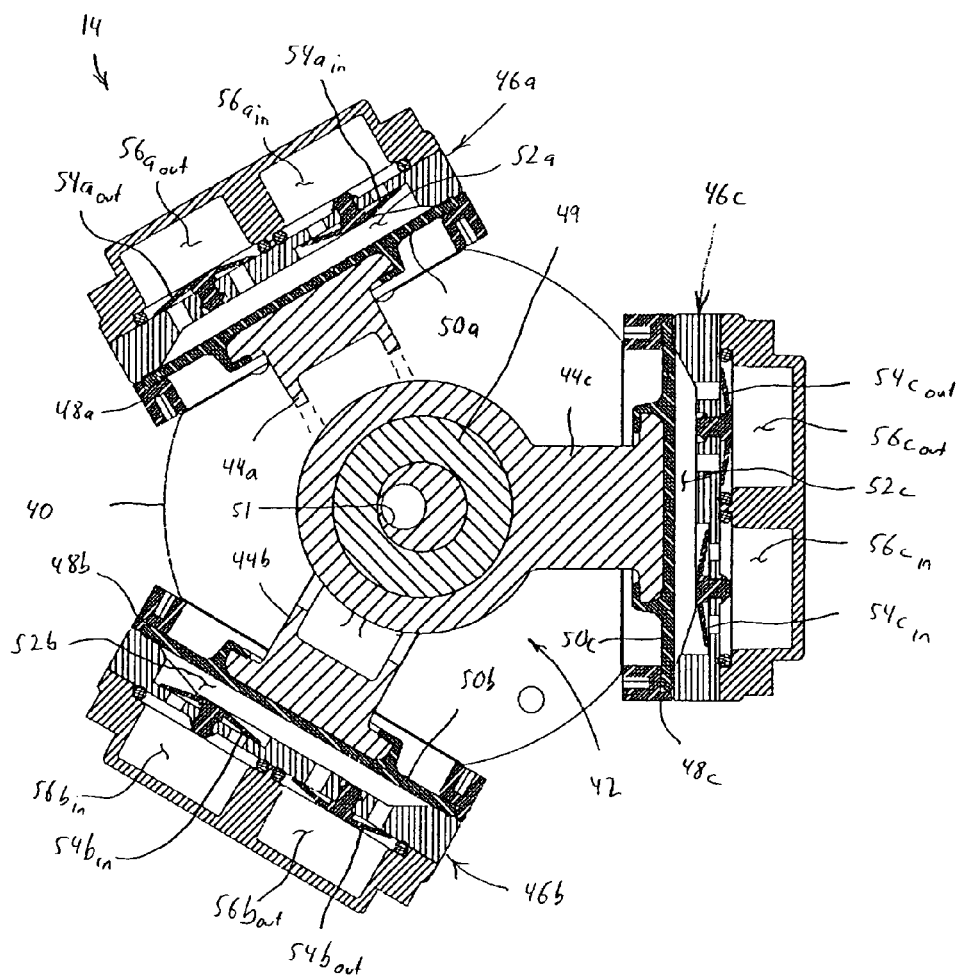
FIG. 6A is a top cross-sectional view of the compressor taken along line 6A-6A of FIG. 5A.

Optionally, as shown in FIG. 6A, housing 48 may include one more partitions defining passages, e.g., an inlet passage $56_{in}$ and an outlet passage $56_{out}$. As explained further below, inlet and outlet passages $56_{in}$, $56_{out}$ communicate with respective passages 62, 64 in air manifold 16, e.g., via ports 57 (not shown in FIG. 6A, see, e.g., FIG. 2) on the bottom of housing 48. An inlet check valve 54 in is provided in line with inlet passage $56_{in}$, e.g., in the partition between chamber 52 and inlet passage $56_{in}$. Inlet check valve $54_{in}$ opens when exposed to a negative pressure within chamber 52, i.e., as diaphragm 50 is directed away from chamber 52, and closes when exposed to a positive pressure within the chamber, i.e., as diaphragm 50 is directed towards chamber 52. Similarly, an outlet check valve $54_{out}$ is provided in line with outlet passage $56_{out}$ that opens when exposed to a positive pressure within chamber 52 and closes when exposed to a negative pressure within the chamber. Check valves 54 may simply be spring biased valves that open in one direction depending upon the pressure differential across the valve, such as conventional umbrella-type valves.

As shown in FIGS. 5C-6B, rods 44 may between respective diaphragms 50 and the crankshaft 49. Rods 44 include first ends including hubs 71 and second ends including rings 73. Hubs 71 may be received in or otherwise secured to supports 65 of diaphragms 50, and rings 73 may be disposed around crankshaft 49. A bearing 77 may be provided between each ring and the crankshaft 242. Thus, crankshaft 49 may rotate freely within the bearings, causing the rings, and consequently, rods 44 may be axially displaced towards and away from central axis 43. This action causes diaphragms 50 to move away from and into chambers 52 to compress air drawn into the chambers.

More specifically, during operation, motor 40 may be continuously or selectively activated to rotate a cam 43 of cam assembly 42 and thereby cause drive shafts 44 to reciprocate axially away from and towards cam assembly 42. For example, cam assembly 42 may be configured such that drive shaft 44 has a total axial displacement of between about three and thirteen millimeters (3-13 mm). This reciprocation causes diaphragms 50 to move in and out relative to housings 46, thereby drawing ambient air into chambers 52 via inlet passages $56_{in}$ and forcing compressed air out of the chambers via outlet passages $56_{out}$. The displacement of the center of diaphragm 50 may correspond one-to-one with the displacement of drive shaft 44. Drive shafts 44 may change the volume of chamber 52, e.g., by between about eighty and ninety five percent (80-95%) above and below its relaxed volume (when diaphragm 50 is substantially relaxed or not subjected to any forces).

In an exemplary embodiment, the reciprocal movement of drive shafts 44 is staggered or offset in time for each of diaphragm assemblies 46a-46c in a predetermined pattern, e.g., based upon the configuration of cam 43 or cam assembly 42. Thus, compressed air is generated sequentially by each head 46. This is believed to minimize the amount of vibration or noise generated by compressor 14, e.g., such that vibration or movement of one of the diaphragm assemblies at least partially offsets the others.

In addition, because the diaphragm assemblies may be angularly offset from one another, e.g., by one hundred twenty degrees (120°) when disposed symmetrically about cam assembly 42, this may also offset or minimize vibrations created during operation of compressor 14. By comparison, in an alternative embodiment, two diaphragm assemblies (not shown) may be provided on opposite sides of the cam assembly in a linear configuration defining an axis, although this configuration may increase vibrations along the axis. As the number of heads is increased, the dynamic peak-to-peak pressure oscillations are reduced, which provides a benefit in reduced sound and reduced vibrations due to reduced pressure pulsations.

Alternatively, more than three (3) heads may be provided, although this may increase the cost and/or complexity of operation of apparatus 10. In order to minimize vibration, it may be desirable to provide an odd number of diaphragm assemblies (e.g., three, five, seven, etc.), e.g., in a symmetrical spoke configuration that does not create a linear axis between any of the diaphragm assemblies, which may at least partially offset vibrations between the various heads.

As best seen in FIGS. 5C and 6B, rods 44 may be stacked axially on the crankshaft 49, while diaphragm assemblies 46 are coplanar within one another. In order to accommodate this arrangement, at least some of the rods may include an offset between the rings and the hubs. For example, a central rod may extend substantially perpendicularly to central axis 43 within a plane, a lower rod may include an offset such that the lower rod is coupled to crankshaft 49 below the plane, and an upper rod may include an offset such that the upper rod is coupled to the crankshaft 49 above the plane. In this configuration, each of the hubs may then be disposed within the plane, allowing the hubs to be connected to respective diaphragms 50.

One of the advantages of this arrangement is that it may minimize a footprint of the diaphragm assemblies, and consequently of the entire compressor. For example, the heads 46 may be mounted directly to support 45 on motor 40. Support 45 may extend outwardly from the motor to provide a lip or other structure to which an upper edge of the heads 46 may be mounted, e.g., using fasteners, such as bolts screws, rivets, and the like, adhesives or other bonding, detents or other mating connectors, and the like. With heads 46 mounted directly to motor 40, the heads may be located relatively close to central axis 43.

Wobble piston compressor 400 shown in FIG. 43 is similar in many respects to the diaphragm compressor shown in FIGS. 5A-6B except that diaphragm 50 is replaced with a piston 402. Each piston includes a piston cup seal 404 to maintain a gas-tight seal between chamber 52 and the opposite side of piston 402.

Figure 45:
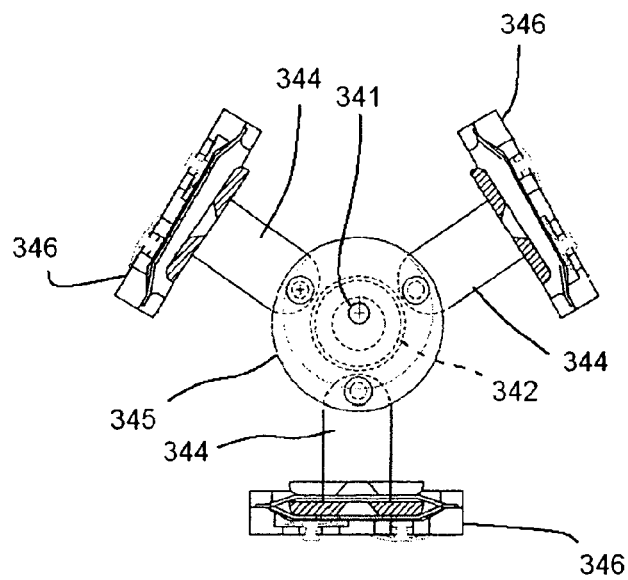
FIG. 45 is a top cross-sectional view of an alternative embodiment for a compressor suitable for use in the present invention.

An alternative configuration of a compressor suitable for use in the portable oxygen concentrator of the present invention is shown in FIG. 45. In this alternative, a motor (not shown) includes an output shaft defining a central axis 341, similar to motor 40. A crankshaft 342 is eccentrically coupled to the output shaft, and a rotor 345 is disposed around the crankshaft (e.g., within one or more bearings, not shown, between rotor 345 and crankshaft 342). A plurality of heads 346, such as any of those disclosed herein, may be disposed around central axis 341, and rods 344 may extend from heads 346 to rotor 345. Thus, as crankshaft 342 rotates about central axis 341, rotor 345 may wobble around the central axis, thereby causing rods 344 to move towards and away from central axis 341 to compress air within heads 346, similar to the previous embodiments.

The configuration shown in FIG. 45, however, may have a larger footprint than the configuration of FIGS. 5A-6B, because of the space required for rotor 345. Thus, this configuration may require more space on a mounting surface, such as an air manifold of an oxygen concentrator. However, this configuration may allow the motor to be supported lower between the heads, which may reduce a height of the compressor, which may be beneficial in some applications.

In the embodiment shown in FIGS. 5A-6B, as well as that in FIG. 45, the reciprocal movement of the rods may be staggered or offset in time for each of the heads. With three heads distributed substantially evenly about the central axis, the heads may be out of phase by about one hundred twenty degrees (120°). Thus, compressed air may be generated sequentially by each of the heads. In addition, because the heads are angularly offset from one another, this configuration may offset or minimize vibrations created during operation of the compressor, as described elsewhere herein.

D. Air and Oxygen Manifolds

Turning to FIGS. 1B, 2, and 7-8B, lower or air manifold 16 generally includes one or more substantially planar structures defining a plurality of passages 62-68 therein. Generally, air manifold 16 is sealed such that passages 62-68 are substantially airtight other than at openings 72-79, 86-90. Openings 72-79, 86-90 may allow other components, e.g., compressor 14, sieve beds 18, and control valves 20, to communicate with passages 62-68 for moving air through air manifold 16 in a desired manner, as explained further below. Optionally, air manifold 16 may include one or more holes, pockets, and the like for receiving mounts, connectors, and/or fasteners (not shown), e.g., for attaching components of apparatus 10 to air manifold 16, e.g., sieve beds 12A, 12B, compressor 14, reservoir 18, and/or air control valves 20.

In an exemplary embodiment, air manifold 16 is substantially rigid, e.g., thereby providing or enhancing a structural integrity of apparatus 10. In one embodiment, air manifold 16 defines one or more outer structural surfaces for apparatus 10, e.g., a lower or bottom surface of the apparatus, thereby eliminating the need for an additional lower exterior skin. Air manifold 16 may be formed from any engineering grade material, e.g., plastic, such as ABS, polycarbonate, and the like; metal, such as aluminum, and the like; or composite materials. Air manifold 16 may be formed by injection molding, casting, machining, and the like.

In an exemplary embodiment, air manifold 16 is formed from relatively lightweight plastic material, e.g., such that the air manifold weighs not more than about 0.25-4.0 pounds. Alternatively, all or one or more portions of air manifold 16 may be formed from resilient semi-rigid or flexible material, e.g., to increase the durability and/or shock resistance of apparatus 10.

In the embodiment shown, air manifold 16 includes (a) a manifold base 58 including a plurality of channels therein that at least partially define passages 62-68, and (b) a manifold cap 60 that mates with manifold base 58 to substantially enclose the channels to further define the passages. It will be appreciated that air manifold 16 may be formed from one or more components, instead of the manifold base and the manifold cap, that mate together or otherwise cooperate to define passages 62-68 described herein.

As best seen in FIG. 7, manifold base 58 includes channels that at least partially define one or more compressor inlet passages 62, compressor outlet passages 64, sieve bed passages 66a, 66b, and exhaust passages 68. Portions of manifold base 58 unnecessary to define passages 62-68 and/or mounting surfaces may be omitted, e.g., to reduce the overall weight of the manifold without substantially impacting its structural integrity. Alternatively, manifold base 58 may have a substantially continuous lower wall, e.g., which may be substantially smooth and/or may include legs or other components (not shown) upon which apparatus 10 may be set.

Figure 2O:
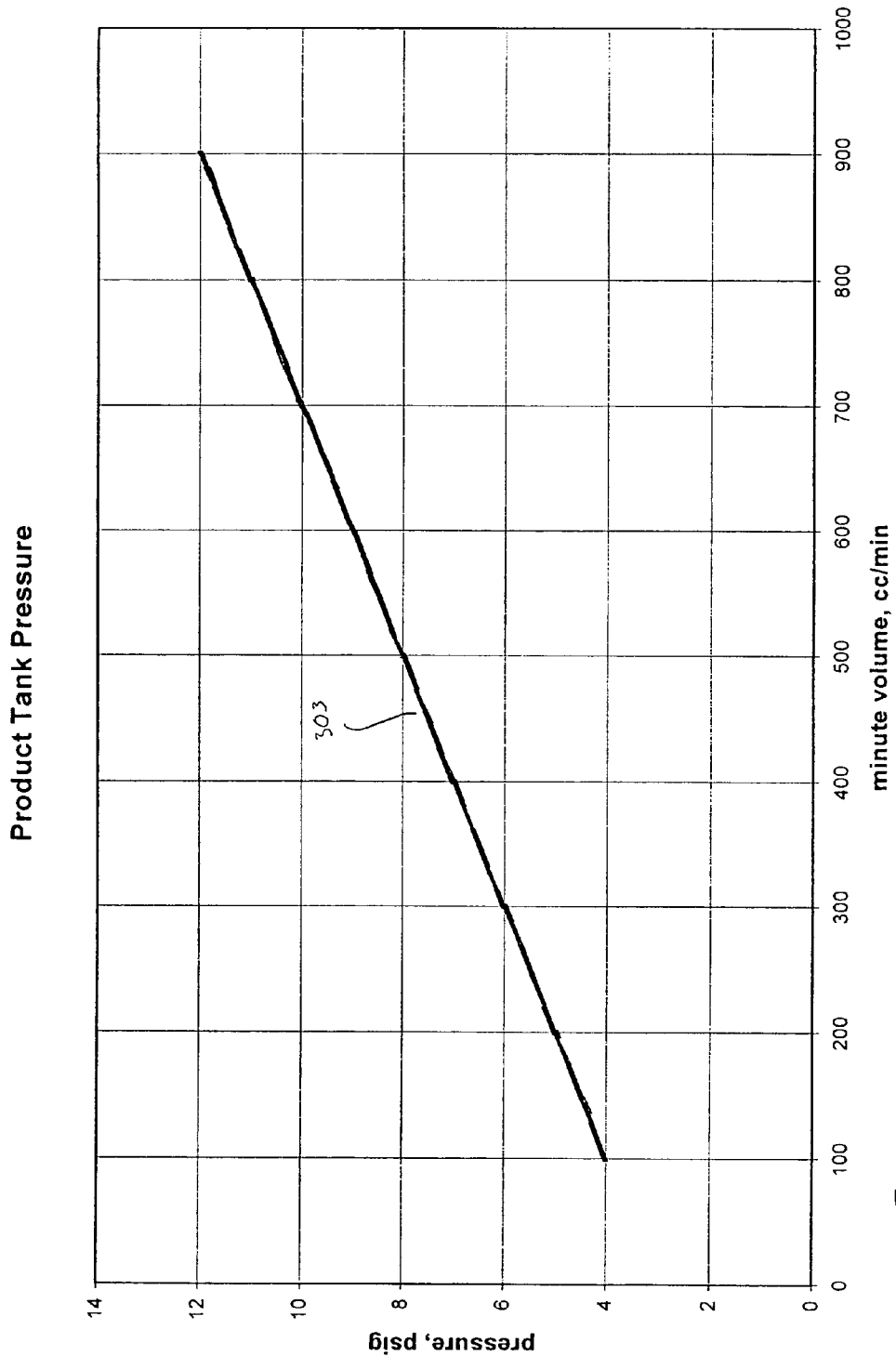
FIG. 2 is an exploded perspective view of the apparatus of FIGS. 1A and 1B.

In addition or alternatively, manifold base 58 may include at least a portion of a side wall 59, e.g., which may define another outer structural surface of apparatus 10. In a further alternative, as shown in FIG. 2, side wall 159 may be part of manifold cap 60, rather than manifold base 58. In yet another alternative, air manifold 16 may be relatively flat (rather than "L" shaped), and the side wall (59, 159) may be a separate component (not shown) that may be connected or otherwise attached to air manifold 16 or oxygen manifold 102.

Figure 8A:
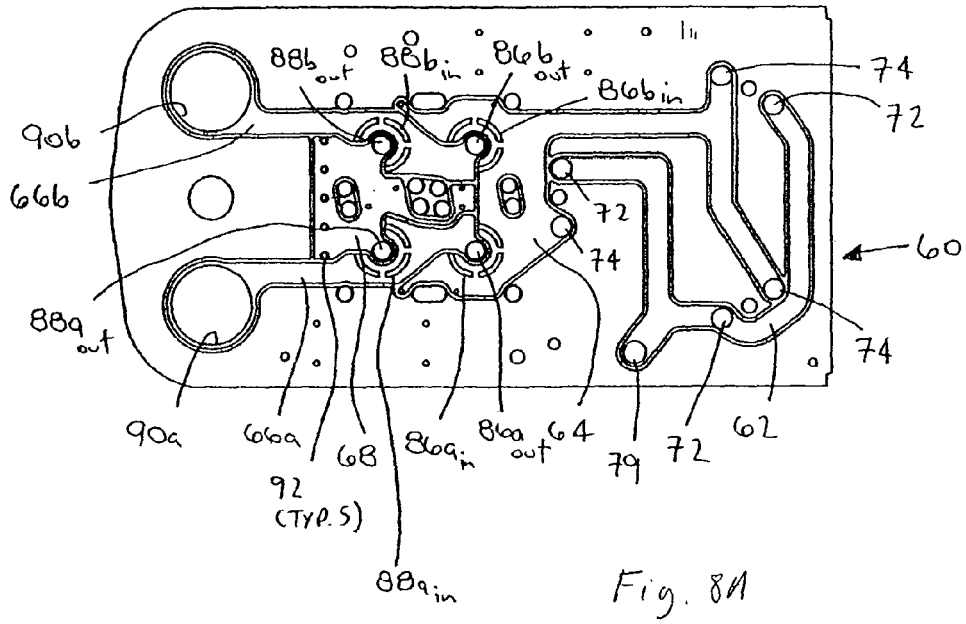
FIGS. 8A and 8B are bottom and top views, respectively, of a manifold cap that attaches to the manifold base of FIG. 7.
Figure 8B:
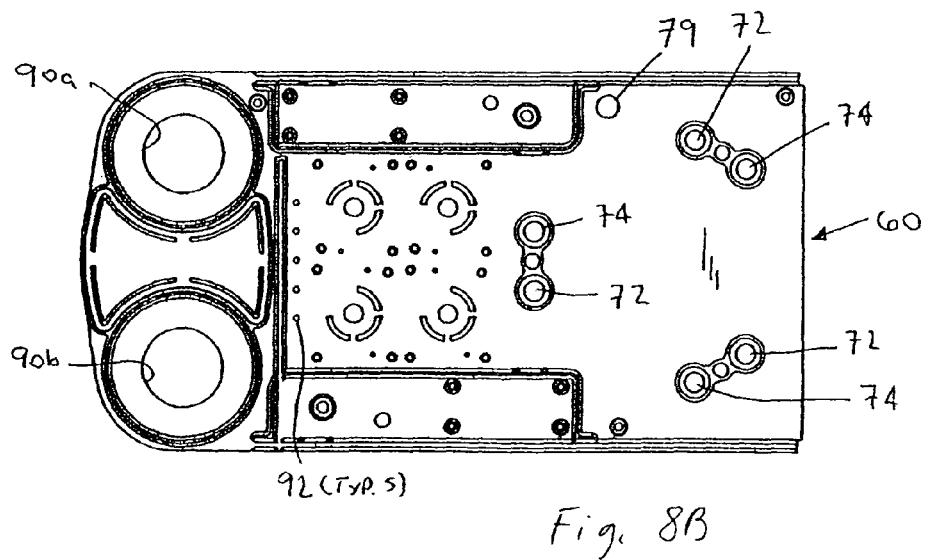

Turning to FIGS. 8A and 8B, manifold cap 60 includes one or more channels that mate with the channels in manifold base 58 to further define passages 62-68, e.g., compressor inlet passages 62, compressor outlet passages 64, sieve bed passages 66, and exhaust passages 68. Alternatively, the channels in manifold cap 60 may be slightly larger or smaller than the channels in manifold base 58 such that the channel walls overlap, which may enhance the connection between manifold cap 60 and manifold base 58. In another alternative, manifold cap 60 has a substantially smooth lower surface that mates against the channel walls and/or other components of manifold base 58 to further define passages 62-68.

Manifold cap 60 may be attached to manifold base 58 using one or more connectors, e.g., cooperating detents, such as tabs and corresponding grooves, or fasteners, such as screws, rivets, bolts, and the like. In addition or alternatively, manifold cap 60 may be attached to manifold base 58 using adhesives, sonic welding, and the like, e.g., along one or more contact surfaces between the manifold base and the manifold cap.

Figure 3:
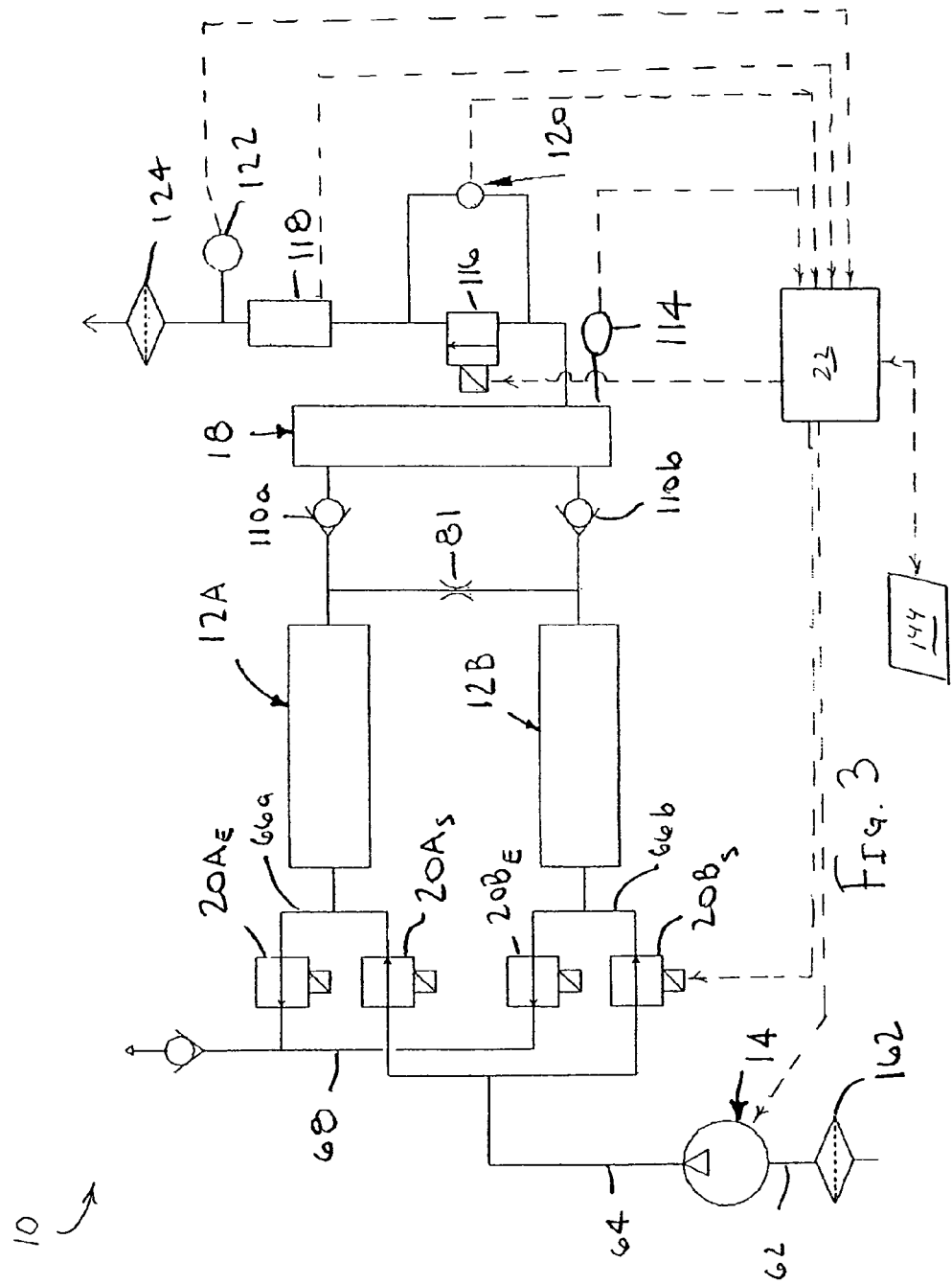
FIG. 3 is a schematic diagram of the apparatus of FIGS. 1A and 1B.

With continued reference to FIGS. 8A and 8B, manifold cap 60 includes a plurality of openings 72-79, 86-90 that communicate with passages 62-68. For example, manifold cap 60 includes an air inlet port 79 that communicates with compressor inlet passage 62. Inlet port 79 is coupled to a tube or other hollow structure (not shown) extending to an inlet opening 160a, 160b (not shown in FIG. 8A or 8B, see FIG. 2) in an outer surface of apparatus 10, e.g., to allow ambient air to be drawn into the apparatus. Optionally, as shown in FIG. 3, an inlet air filter 162 may be provided in line before inlet port 79 to remove dust or other particles from the ambient air drawn into inlet opening 160a, 160b before it enters compressor 14.

Manifold cap 60 includes multiple pairs of openings 72, 74 for communicating with compressor 14. In the embodiment shown, manifold cap 60 includes three pairs of openings 72, 74 corresponding to ports 57 (not shown, see FIG. 2) on the three diaphragm assemblies 46 of compressor 14. Each pair of openings 72, 74 is spaced apart a predetermined distance similar to the spacing of ports 57 on diaphragm assemblies 46. One or both of openings 72, 74 and ports 57 may include nipples or other extensions to facilitate a substantially airtight connection between diaphragm assemblies 46 and manifold cap 60. Ports 57 are connected to openings 72, 74, e.g., by one or more of interference fit, mating threads, cooperating detents, adhesives, and the like.

When compressor 14 is mounted to or adjacent air manifold 16, inlet passages $56_{in}$ of diaphragm assemblies 46 communicate with openings 72, and consequently with compressor inlet passage 62. During use, when each diaphragm assembly 46, in turn, draws in outside air via inlet passages $56_{in}$, air may be drawn through respective openings 72, compressor inlet passage 62, and inlet port 79. Similarly, outlet passages $56_{out}$ of diaphragm assemblies 46 communicate with openings 74, and consequently with compressor outlet passage 64. During use, when each of diaphragm assemblies 46 delivers compressed air out outlet passages $56_{out}$, the compressed air enters the respective openings 74 into compressor outlet passages 64 in air manifold 16.

With continued reference to FIGS. 8A and 8B, manifold cap 60 also includes a plurality of air control valve openings 86, 88 adjacent one another that overly compressor outlet passage 64, sieve bed passages 66, and/or exhaust passage 68. Thus, when manifold cap 60 is attached to manifold base 58, air control valve openings 86, 88 communicate with respective passages 64-68. In particular, supply valve inlet openings $86_{in}$ communicate with compressor outlet passage 64, while exhaust valve inlet openings $88_{in}$ communicate with respective sieve bed passages 68. Supply valve outlet openings $86_{out}$ communicate with respective sieve bed passages 66, while exhaust valve outlet openings $88_{out}$ communicate with exhaust passage 68.

Manifold cap 60 includes sieve bed openings 90a and 90b that communicate with enlarged portions of sieve bed passages 66. Thus, sieve bed openings 90a, 90b communicate with first ends 32 of respective sieve beds 12 when the sieve beds are mounted to or adjacent air manifold 16. Further, as best seen in FIG. 8B, manifold cap 60 also includes one or more exhaust openings 92 that communicates with exhaust passage 68.

Optionally, a tube, nozzle, or other device (not shown) may be coupled to exhaust opening(s) 92 to direct exhaust air (generally concentrated nitrogen) from sieve beds 12, as explained further below. In one embodiment, the exhaust gas is directed toward controller 22 or other electronics within apparatus 10, e.g., for cooling the electronics. Using air with increased nitrogen content as a cooling fluid for the internal electronics provides a safety feature for apparatus 10, namely reducing the risk of fire if the electronics ever overheat or short. Since some of the oxygen has been removed from the exhaust air, the exhaust air is less likely to support a fire. Further, with the exhaust air being directed into the interior of apparatus 10, if reservoir 18 or sieve beds 12 were ever to develop a leak communicating with the interior of apparatus 10, the resulting gas mixture would have no more oxygen (as a percentage of volume) than ambient air.

As described further below, air control valves 20 may be mounted to manifold cap 60 over valve openings 86, 88. The air control valves are selectively opened and closed to provide flow paths, e.g., from compressor outlet passage 64 to sieve bed passages 66 and/or from sieve bed passages 66 to exhaust passage 68. For example, with additional reference to FIG. 3, when supply air control valve $20a_s$, is open, a flow path is defined from compressor 14 through openings 72, compressor passage 62, supply inlet openings $86_{in}$, air control valve $20a_s$, supply outlet opening $86_{out}$ and sieve bed passage 66a, into sieve bed 12A. When exhaust air control valve $20b_E$ is open, a flow path is defined from the sieve bed 12B, though sieve bed passage 66b, exhaust inlet openings $88_{in}$, air control valve $20b_E$, exhaust outlet openings $88_{out}$ exhaust passage 68, and out exhaust opening(s) 92.

Air manifold 16 replaces the need for a plurality of tubes and valves that would otherwise be necessary to deliver air to and from sieve beds 12. Because these individual tubes and valves are eliminated and replaced with a simple manifold including not more than four air control valves 20, air manifold 16 reduces the overall size, weight, and/or cost of apparatus 10, which may be useful, particularly in order to make apparatus 10 convenient, easy to use, and/or inexpensive.

Alternatively, the same objective may be achieved if two 3-way valves, or one 4-way valve was employed in a like manner.

Figure 11:
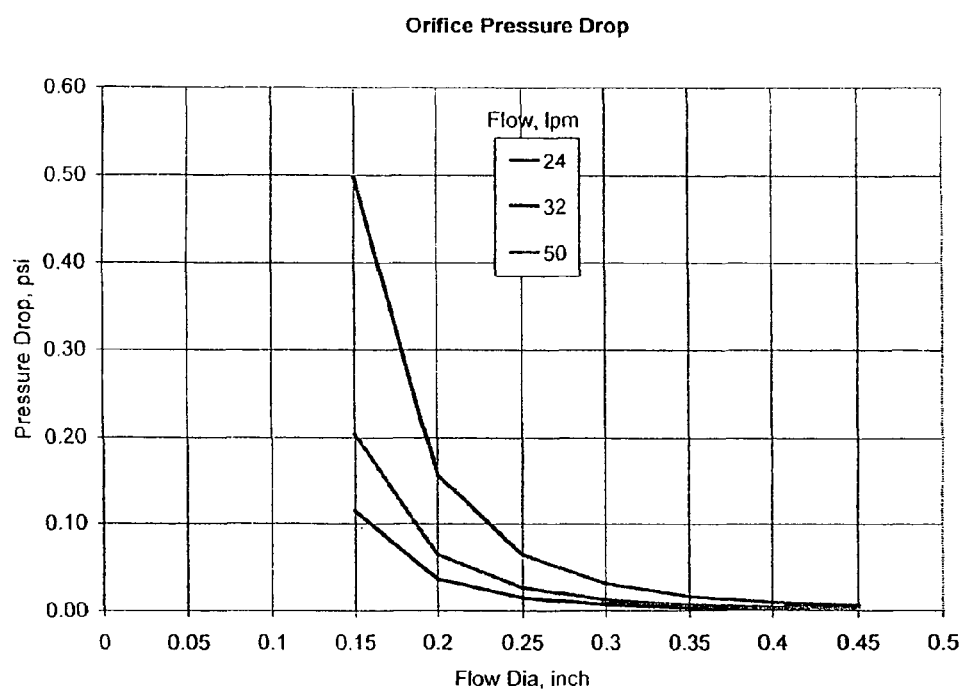
FIG. 11 is a graph showing the pressure drop of air flowing though a passage as a size of the passage increases based upon exemplary average flow rates.

In addition, air manifold 16 may facilitate modifications, e.g., to reduce pressure losses and/or dampen noise. For example, to minimize energy needs for apparatus 10, the size and/or shape of passages 62-68 may be designed to reduce losses as compressed air pass through these passages. It has been found that if the pressure loss increases by one pound per square inch (1 psi), it may increase power consumption of the apparatus 10 by as much as ten percent (10%) or more. FIG. 11 shows pressure losses that may be encountered during three exemplary average flow rates, i.e., twenty four (24), thirty (30) and fifty (50) liters per minute (lpm). As the average flow diameter of passages 62-68 is increased, the pressure drop is reduced significantly. Thus, it may be desirable for passages 62-68 to have a size of at least about 0.25 inch diameter or other equivalent cross-section.

In addition, air manifold 16 may facilitate providing baffles or other sound dampening devices or materials within the flow paths of the air moving through apparatus 10. For example, one or more baffles, venturis, flow modifiers, and the like (not shown) may be molded directly into the channels of manifold base 58 to absorb sound waves or reduce noise generated by airflow. Alternatively, such components may be inserted or mounted within the channels before manifold cap 60 is attached to manifold base 58. In yet another alternative, air manifold 16 may allow flow control valves to be mounted directly in one or more of passages 62-68.

Returning to FIGS. 1A-3, air control valves 20 may be mounted or otherwise attached to air manifold 16, e.g., to manifold cap 60. In the embodiment shown, four "two way" air control valves 20 are mounted to manifold cap 60, e.g., using one or more connectors, fasteners, adhesives, and the like. As explained further below, four air control valves 20 allow each sieve bed 12A, 12B to be pressurized and/or exhausted independently of the other, optionally with the ability to overlap the pressurization cycles.

An exemplary two-way valve that may be used for each of valves 20 is the SMC DXT valve, available from SMC Corporation of America, of Indianapolis, Ind. This valve is a relatively small plastic pilot operated diaphragm valve. Because of the large diaphragm area, it has a very low minimum operating pressure, which may be particularly useful given the operating pressures of the apparatus 10 during use. The valve may be provided as "normally open." When pressure is applied to the top side of the diaphragm through the pilot valve, the diaphragm may be forced down onto a seat, shutting off the flow. Either a normally open or normally closed pilot solenoid valve may be used. Since the diaphragm valve itself is normally open, using a normally open solenoid valve may create normally closed overall operation, requiring application of electrical energy to open the valve.

Alternatively, air control valves 20 may be replaced with two "three-way" valves, which may require some minor changes to the openings and/or passages in air manifold 16. Such valves, however, may be more expensive, complicated to operate, and/or may require greater pressure to pilot than the pressures encountered during use of apparatus 10. In further alternatives, one or more other multiple position valves may be provided, instead of the four two way valves.

Returning to FIG. 2, the four air control valves illustrated therein may be provided on a single valve manifold 21, e.g., an aluminum manifold, and the ports may be threaded inlet and outlet ports provided separately or as part of valve manifold. After assembling air control valves 20 to valve manifold 21, the valve manifold is mounted to air manifold 16 over openings 86, 88. Alternatively, the individual air control valves may be mounted directly to air manifold 16, e.g., to avoid the need for valve manifold 21 or any other fittings and/or tubing, which may further reduce the overall size and/or weight of apparatus 10.

Figure 9A:
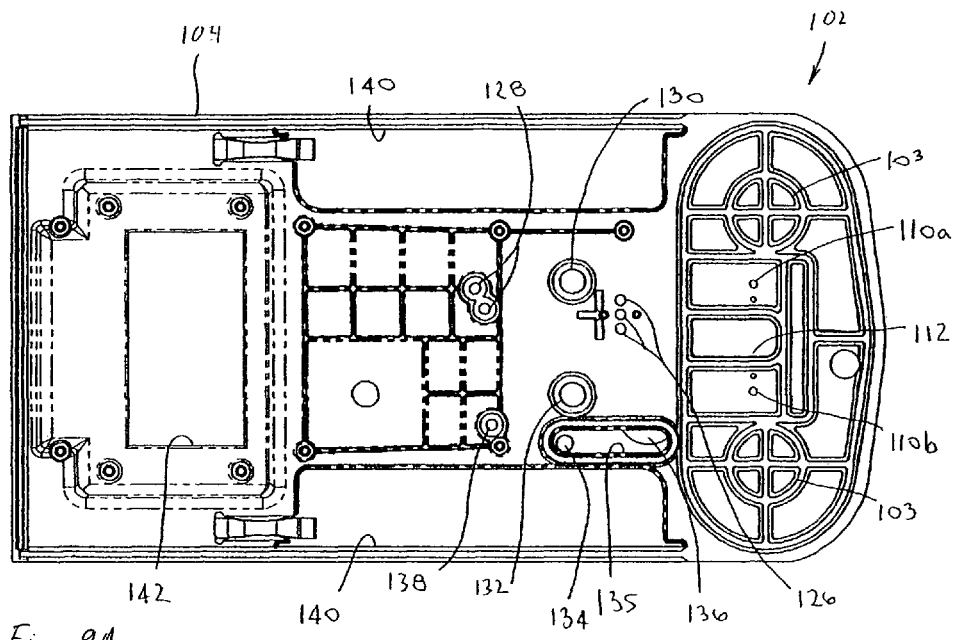
FIGS. 9A and 9B are perspective views of upper and lower sides of a manifold base that defines part of an oxygen delivery manifold in the apparatus of FIGS. 1A and 1B.
Figure 9B:
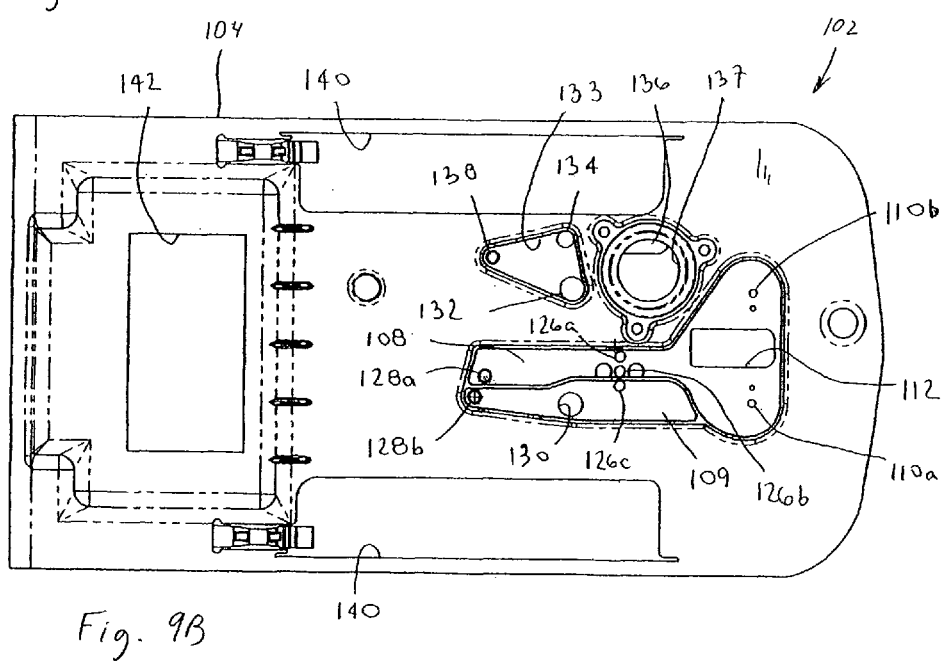

Returning to FIGS. 1A, 1B, and 2, with additional reference to FIGS. 9A-9B, upper or oxygen delivery manifold 102 is provided for delivering oxygen stored in reservoir 18 to a user of apparatus 10. Similar to air manifold 16, oxygen delivery manifold 102 provides sufficient structural integrity to provide an outer structural surface of apparatus 10, e.g., thereby eliminating the need for a separate outer or upper skin for the apparatus. Oxygen delivery manifold 102 may be manufactured and assembled using similar materials and/or methods to air manifold 16, described above.

Optionally, as shown in FIG. 9B, oxygen delivery manifold 102 includes one or more ribs or other reinforcing structures 103, e.g., on a lower surface of the oxygen delivery manifold. The reinforcing structures may be molded or otherwise formed directly in oxygen delivery manifold 102 in a desired pattern or attached to the oxygen delivery manifold, e.g., overlying the sieve beds 12. Such reinforcing structures may reinforce oxygen delivery manifold 102, e.g., from biasing mechanism 39 within the sieve beds 12A, 12B and/or against the pressure of the air within the sieve beds, which may apply an upward force against oxygen supply manifold 102.

In the embodiment shown in FIG. 2, oxygen delivery manifold 102 includes a manifold base 104 at least partially defining one or more oxygen delivery passages 108, 109, and a manifold cap 106 further defining oxygen delivery passages 108, 109. Oxygen delivery passages 108, 109 are disposed adjacent one another in the manifold base 104 and include a plurality of openings 126-138 for communicating with other components related to delivering oxygen to a user of apparatus 10, as explained further below. Manifold base 104 may also include one or more battery openings 140a and 140b and/or an interface window 142, which may be molded or otherwise formed therein. Interface window 142 allows access to user interface 144, which is necessary, for example, if the user interface is a touch screen display 230.

Optionally, as shown in FIG. 2, manifold base 104 of oxygen delivery manifold 102 may include at least a portion of side panel 159. Side panel 159 may abut, interlock, or otherwise mate with side panel 59 on air manifold 16. Side panels 59 and 159 provide an outer structural wall for apparatus 10 that is substantially rigid. Thus, side panels 59 and 159, manifolds 16 and 102, sieve beds 12A and 12B, and/or reservoir 18 combined provide the necessary structural frame to support apparatus 10 and its internal components. Alternatively, one or both of side panels 59, 159 may be provided as a separate panel (not shown) that is connected or otherwise attached to air manifold 16 and/or oxygen delivery manifold 102.

Returning to FIG. 2, side panel 159 may include one or more inlet openings 160a, 160b that communicate with an interior of apparatus 10. As shown, side panel 159 includes two inlet openings or screens 160a and 160b adjacent one another. Inlet openings 160a, 160b are provided in any desired array, e.g., in a rectangular, square, round, or other configuration. In an exemplary embodiment, each of inlet openings 160a and 160b have a height and/or width of between about one and two inches (25-50 mm). Inlet openings 160a and 160b include relatively small holes, e.g., between about 0.025-0.15 inch (0.6-4 mm) diameter, allowing air to pass easily through the inlet openings, yet preventing large objects from passing therethrough.

For example, first inlet opening 160a may provide an inlet for drawing air into compressor 14, e.g., via a tubing and the like (not shown) communicating with air inlet port 79 of air manifold 16, as described above. Second inlet opening 160b may provide a ventilation inlet for ambient air to be drawn into the interior of apparatus 10, e.g., to assist cooling the internal electronics and/or the sieve beds. An intake fan 164 may be mounted adjacent second inlet opening 160b, e.g., to draw ambient air into the interior of apparatus 10 at a constant or variable speed and/or volume.

Optionally, apparatus 10 may include one or more gaps, e.g., vertical spaces between sieve beds 12A, 12B and/or reservoir 18 (not shown) to allow air to escape from the interior of the apparatus. For example, it may be desirable to have air within the interior of apparatus 10 (particularly, the exhaust gas from the exhaust opening(s) 92) escape the apparatus on the opposite end from inlet openings 160a, 160b to avoid drawing nitrogen-rich air back into sieve beds 12A, 12B, which would reduce the efficiency, and possibly effectiveness, of the apparatus. Alternatively, one or more outlet openings (not shown) may be provided on the apparatus, e.g., in air manifold 16, oxygen delivery manifold 102, and/or one or more side panels (not shown) to allow air to escape from within the interior of apparatus 10 in a desired manner.

E. Oxygen Delivery Components

Returning to FIGS. 2 and 3, apparatus 10 includes one or more components related to delivering oxygen from reservoir 18 to a user. These components are attached or otherwise mounted to or adjacent oxygen delivery manifold 102, e.g., using methods similar to the methods for attaching other components of apparatus 10 described herein.

For example, a pair of check valves 110a, 110b may be provided in manifold base 104 that overlie openings 82 in cap 80. Check valves 110a and 110b may simply be pressure-activated valves, similar to check valves 54 described above. When oxygen delivery manifold 102 is mounted to or adjacent sieve beds 12A, 12B and reservoir 18, check valves 110a, 110b provide one-way flow paths from sieve beds 12A, 12B into oxygen delivery passage 108. Oxygen delivery passage 108 communicates directly and continuously with reservoir 18 via opening 112.

A pressure sensor 114 may be provided within reservoir 18 or communicating with oxygen delivery passage 108. Pressure sensor 114 may detect an absolute pressure within reservoir 18, and, consequently, within the oxygen delivery passage 108. In addition, because of the presence of check valves 110a and 110b, pressure sensor 114 provides a reading of the maximum pressure within sieve beds 12. Specifically, because check valves 110 and 110b allow one-way flow of oxygen from the sieve beds into reservoir 18 and oxygen delivery passage 108, whenever the pressure in either sieve bed exceeds the pressure in reservoir 18, the respective check valve 110a or 110b is open. Once the pressure within either sieve bed becomes equal to or less than the pressure in reservoir 18, the respective check valve closes.

The present invention also contemplates providing an oxygen delivery valve 116, oxygen sensor 118, one or more pressure sensors 120, 122, and one or more air filters 124 may be provided in line with oxygen delivery passages 108, 109, e.g., mounted to oxygen delivery manifold 102. For example, with additional reference to FIGS. 9A and 9B, manifold base 104 may include oxygen control valve openings 126, pressure sensor openings 128, 138, oxygen sensor openings 130, 132, and outlet openings 134, 136 for communicating with these components. Oxygen delivery valve 116 may be mounted to oxygen delivery manifold 102, e.g., below oxygen control valve openings 126, for controlling the flow of oxygen between oxygen delivery passages 108 and 109, and consequently from reservoir 18 out of apparatus 10 to a user. The oxygen delivery valve may be a solenoid valve coupled to controller 22 that may be selectively opened and closed. An exemplary valve that may be used for oxygen delivery valve 116 is the Hargraves Technology Model 45M, which has a relatively large orifice size, thereby maximizing the possible flow though the oxygen delivery valve. Alternatively, it may also be possible to use a Parker Pneutronics V Squared or Series 11 valve.

When oxygen delivery valve 116 is open, oxygen flows from oxygen delivery passage 108, through oxygen control valve openings 126a, 126b, oxygen delivery valve 116, oxygen control valve opening 126c, and into oxygen delivery passage 109. Oxygen delivery valve 116 may be opened for desired durations at desired frequencies, which may be varied by controller 22, thereby providing pulse delivery as explained further below. Alternatively, controller 22 may maintain the oxygen delivery valve 116 open to provide continuous delivery, rather than pulsed delivery. In this alternative, controller 22 may throttle oxygen delivery valve 116 to adjust the volumetric flow rate to the user.

In the illustrated embodiment, pressure sensor 120 is mounted to and/or below oxygen delivery manifold 102 such that ports of the pressure sensor are coupled to or otherwise communicate with pressure sensor openings 128. Thus, the ports of pressure sensor 120 measure a pressure difference between oxygen delivery passages 108, 109, and consequently across oxygen delivery valve 116. Optionally, pressure sensor 120 may be used to obtain reservoir pressure, and pressure sensor 114 may be eliminated. For example, when oxygen delivery valve 116 is closed, pressure upstream of the oxygen delivery valve correspond substantially to the pressure within reservoir 18.

Pressure sensor 120 may be coupled to controller 22, e.g., to provide signals that are processed by the controller to determine the pressure differential across the oxygen delivery valve. Controller 22 may use this pressure differential to determine a flow rate of the oxygen being delivered from apparatus 10 or other parameters of oxygen being delivered. Controller 22 may change the frequency and/or duration that oxygen delivery valve 116 is open based upon the resulting flow rates, e.g., based upon one or more feedback parameters, as described further below.

Oxygen sensor 118 may also be mounted to and/or below oxygen delivery manifold 102 such that ports on oxygen sensor 118 communicate with oxygen sensor openings 130, 132. Oxygen sensor 118 measures the purity of oxygen passing therethrough. An example of such as device is an ultrasonic sensor that measures the speed of sound of the gas passing through the oxygen sensor, such as those made by Douglas Scientific of Shawnee, Kans. Alternatively, oxygen sensor 118 may be a ceramic or sidestream sensor. Ultrasonic sensors may use less power than ceramic sensors, e.g., about fifty milliwatts (50 mW) versus one watt (1 W)), but may be more expensive.

Oxygen sensor 118 is coupled to controller 22 and generates electrical signals proportional to the purity. These signals are processed by controller 22 and used to change the operation of apparatus 10, as described further below. Because the accuracy of oxygen sensor 118 may be affected by airflow therethough, it may be desirable to sample the purity signals during no flow conditions, e.g., when oxygen delivery valve 116 is closed.

Pressure sensor 122 is mounted to and/or or below oxygen manifold 102 such that the port of pressure sensor 122 communicates with pressure sensor opening 138. Pressure sensor 122 may be a piezo resistive pressure sensor capable of measuring absolute pressure. Exemplary transducers that may be used include the Honeywell Microswitch 24PCO1SMT Transducer, the Sensym SXO1, Motorola MOX, or others made by All Sensors. Because pressure sensor 122 may be exposed to the full system pressure of apparatus 10, it may be desirable for the over-pressure rating of pressure sensor 122 to exceed the full system pressure, e.g., to be at least about fifteen pounds per square inch (15 psi).

Pressure sensor 122 is coupled to controller 22 so as to provide signals proportional to the detected pressure. Because pressure sensor 122 may not have a zero reference, the pressure signals from pressure sensor 122 may drift during operation of the apparatus. To minimize any drift or other error introduced by pressure sensor 122, a small valve (not shown) may be coupled to pressure sensor 122 to periodically vent or zero the pressure sensor, e.g., when oxygen delivery valve 116 is open and delivering oxygen.

Alternatively, a relative small orifice (e.g., about 0.010 inch diameter) may be provided in the line between oxygen delivery valve 116 (e.g., the normally open port), and pressure sensor 122. This orifice may be small enough not to adversely affect the pressure signals from pressure sensor 122, but large enough so that the pressure sensor is bled to zero, e.g., during a pulse as short as one hundred milliseconds (100 ms.). Additional information on using such an orifice may be found in published application No. 2003/0150455, the entire disclosure of which is expressly incorporated by reference herein. In another alternative, controller 22 implements a filtering algorithm to recognize the beginning of the user's breath.

Manifold base 104 may include a recess 133 that communicates with oxygen sensor opening 132 and pressure sensor opening 138. A cover or other member not shown) may be attached over or otherwise cover the recess 133, e.g., to provide a substantially airtight passage defined by the recess. Thus, pressure sensor 122 may measure an absolute pressure of the oxygen within recess 133. This pressure reading may be used to detect when a user is beginning to inhale, e.g., based upon a resulting pressure drop within recess 133, which may trigger delivering a pulse of oxygen to the user, as explained further below.

Air filter 124 may be mounted to or adjacent oxygen delivery manifold 102, and may include any conventional filter media for removing undesired particles from oxygen being delivered to the user. As best seen in FIG. 9A, the oxygen delivery manifold 102 may include a recess 137 shaped to receive air filter 124 therein. Air filter 124 may be secured within recess 137 by an interference fit, by one or more connectors, adhesives, and the like.

Recess 137 (shown in FIG. 9A) communicates with channel 135 (shown in FIG. 9B) via outlet opening 136. In the embodiment shown, channel 135 extends between outlet openings 134, 136 formed in and through manifold base 104. A cover or other member (not shown) may be attached or otherwise cover channel 135, e.g., to provide a substantially airtight passage defined by the channel. Thus, oxygen delivered from oxygen sensor 118 may leave recess 133 though outlet opening 134, pass along channel 135, and enter recess 137 through outlet opening 136. The oxygen may then pass through air filter 124 and be delivered to the user.

Optionally, a cannula barb 139 or other device is mounted to oxygen delivery manifold 102 over recess 137. Cannula barb 139 is attached to oxygen delivery manifold 102 using any conventional method, e.g., by mating threads, one or more detents or other connectors, adhesives, and the like (also not shown). The cannula barb may include a nipple or other connector to which a cannula, e.g., flexible hose, and the like (also not shown), may be attached for delivering the oxygen to a user, as is known in the art. The cannula barb may be separate from air filter 124, or the cannula barb and air filter 124 may be a single assembly that is attached together to oxygen delivery manifold 102 over recess 137.

It will be appreciated that other configurations and/or components may be provided for delivering oxygen to the user, rather than oxygen delivery manifold 102 and the components attached thereto described above. In addition, although the components, e.g., oxygen delivery valve 116, pressure sensors 120, 122, oxygen sensor 118, and air filter 124 are described in a particular sequence (relative to oxygen flowing through the oxygen delivery manifold 102), the sequence of these components may be changed, if desired.

Returning to FIG. 2, controller 22 may include one or more hardware components and/or software modules that control one or more aspects of the operation of the apparatus 10. Controller 22 may be coupled to one or more components of the apparatus 10, e.g., the compressor 14, air control valves 20, oxygen delivery valve 116, pressure sensors 114, 120, 122, and/or oxygen sensor 118. The components may be coupled by one or more wires or other electrical leads (not shown for simplicity) capable of receiving and/or transmitting signals between the controller 22 and the components.

Controller 22 may also be coupled to a user interface 144, which may include one or more displays and/or input devices. In embodiment shown in FIG. 2, user interface 144 is a touch screen display that is mounted within or below interface window 142 in oxygen delivery manifold 102. User interface 144 displays information regarding parameters related to the operation of apparatus 10 and/or allow the user to change the parameters, e.g., turn apparatus on and off, change dose setting or desired flow rate, etc., as explained fuller below. Although a single user interface 144 is shown, it will be appreciated that the user interface may include multiple displays and/or input devices, e.g., on/off switches, dials, buttons, and the like (not shown). User interface 144 may be coupled to controller 22 by one or more wires and/or other electrical leads (not shown for simplicity), similar to the other components.

For simplicity, controller 22 shown in FIG. 2 includes a single electrical circuit board that includes a plurality of electrical components thereon. These components may include one or more processors, memory, switches, fans, battery chargers, and the like (not shown) mounted to the circuit board. It will be appreciated that controller 22 may be provided as multiple subcontrollers that control different aspects of the operation of apparatus 10. For example, a first subcontroller may control operation of motor 40 of compressor 14 and air control valves 20, and a second subcontroller may control operation of oxygen delivery valve 116 and/or user interface 144.

Controller 22, e.g., a first subcontroller that controls operation of the compressor 14, may include a brushless DC motor controller, such as one of the Motorola/ON MC33035 family, the Texas Instruments DSP TMS 320LF240 and/or the MSP 430 F4491PZ. Such a controller may use utilize hall sensors (not shown) in the motor 40 to time commutation. Alternatively, a sensor-less controller may be used that allows commutation timing via back-EMF measurement, i.e., the position of the armature of the motor may be determined by the measurement of the back EMF of the coils of the motor. This alternative may be less expensive, because the sensors in the motor may be eliminated, and the wiring to the motor may be simplified. For example, Fairchild may have a dedicated integrated circuit appropriate for use in the controller 22. Alternatively, a Texas Instruments DSP TMS 320LF240 or the MSP 430 F4491PZ microprocessor may be used that includes integrated sensor-less control peripherals.

The first subcontroller (or other component of controller 22) may control a speed of the motor, and consequently, a pressure and/or flow rate of compressed air delivered by diaphragm assemblies 46. Controller 22 may also control the sequence of opening and closing the air control valves 20, e.g., to charge and purge sieve beds 12 in a desired manner, such as the exemplary methods described further below.

The second subcontroller (or other component of controller 22) may control oxygen delivery valve 116, e.g., to deliver oxygen from reservoir 18 to a user based upon pressure signals received from pressure sensor 122. The second subcontroller may also receive input instructions from the user and/or display information on user interface 144. In addition, the subcontrollers or other components of controller 22 may share information in a desired manner, as described below. Thus, controller 22 may include one or more components, whose functionality may be interchanged with other components, and the controller should not be limited to the specific examples described herein.

In addition, apparatus 10 may include one or more power sources, coupled to controller 22, compressor 14, air control valves 20, and/or oxygen delivery valve 116. For example, as shown in FIG. 2, a pair of batteries 148 are provided that mount or otherwise secure to air manifold 16, e.g., along the open sides between side walls 59, 159 and sieve beds 12. Air manifold 16 may include one or more mounts 149 that are received in batteries 148, e.g., to stabilize and/or otherwise secure the batteries vertically within apparatus 10. In addition or alternatively, other straps or supports (not shown) may also be used to secure the batteries 148 within the apparatus.

In exemplary embodiments, batteries 148 are rechargeable batteries, such as eleven (11) volt nominal 3 series Li-Ion batteries, 4 series Li-Ion batteries (such as those available from Inspired Energy, e.g., Par No. NL2024), and the like. For 3 series packs, standard one pound (lb) packs may have a current limitation of three (3) amperes, while one and a half pound (1.5 lb.) packs may have a maximum current of six (6) amperes. Additional information on Inspired Energy batteries that may be used may be found at ww.inspired-energy.com. Other sources of batteries may include Molien Energy (www-.molienergy.com), GP Batteries (www.gpbatteries.com), Micro-Power (www.micro-power.com), and Buchmann (www.buchmann.ca).

Controller 22 controls distribution of power from batteries 148 to other components within apparatus 10. For example, controller 22 may draw power from one of the batteries until its power is reduced to a predetermined level, whereupon the controller may automatically switch to the other of the batteries. Alternative, the present invention contemplates that controller 22 causes both batteries to discharge equally.

Optionally, apparatus 10 may include an adapter so that an external power source, e.g., a conventional AC power source, such as a wall outlet, or a portable AC or DC power source, such as an automotive lighter outlet, a solar panel device, and the like (not shown) can be used to provide power to the apparatus. Any transformer or other components (also not shown) necessary to convert such external electrical energy such that it may be used by apparatus 10 may be provided within the apparatus, in the cables connecting the apparatus to the external power source, or in the external device itself.

Optionally, controller 22 may direct some electrical energy from external sources back to batteries 148 to recharge them in a conventional manner. The controller may also display the status of the electrical energy of the apparatus, e.g., automatically or upon being prompted via user interface 144, such as the power level of batteries 148, whether apparatus 10 is connected to an external power source, and the like. Controller 22 may include one or more dedicated components for performing one or more of these functions. An exemplary battery management integrated circuit ("IC") that may be included in controller 22 is the Maxim MAX 1773 type, which is designed for dual battery systems (see, e.g., www.maxim-ic.com/quick_view2.cfm/qv_pk/2374 for more information). Another is the Linear LTC 1760, which is also designed for dual battery systems and combines similar selector functions with charging (see, e.g., www.linear.com/prod/datasheet.html?datasheet=989 for more information).

F. Assembly

Returning to FIGS. 1A-3, to assemble apparatus 10, the components of air manifold 16 and oxygen manifold 102 may be manufactured and assembled, as described above. For example, manifold bases 58, 104, manifold caps 60, 106, and/or other caps or covers (not shown) may be molded or otherwise manufactured, and manifold caps 60, 106, and/or other caps or covers (not shown) may be attached to manifold bases 58, 104, e.g., using one or more of cooperating detents, connectors, fasteners, interference fit, adhesives, and the like (not shown). Similarly, sieve beds 12, reservoir 18, and compressor 20 may be manufactured and/or assembled, e.g., as described above.

Air control valves 16, sieve beds 12, reservoir 18, and/or compressor 20 may be mounted to air manifold 16, e.g., to the manifold cap 60, also as described above. Similarly, oxygen delivery valve 116, pressure sensors 120, 122, oxygen sensor 118, air filter 124, and/or other components may be mounted to oxygen delivery manifold 102. Oxygen delivery manifold 102 may be attached to the sieve beds 12 and reservoir 18, e.g., after or before the sieve beds and reservoir are attached to air manifold 16. The order of assembly is not important and may be changed to facilitate desired manufacturing facilities and/or procedures.

Simultaneously or separately, side walls 59, 159 may be attached to one another, or, if side walls 59, 159 are one or more separate panels (not shown), they may be attached to and/or between air manifold 16 and oxygen delivery manifold 102. The resulting structure may provide a structural frame for apparatus 10 that may eliminate the need for additional supports or structural or cosmetic outer skins.

Controller 22, which is provided on a circuit board, is mounted within the structural frame and any wires or other leads are connected between the controller and the other components coupled thereto. In an exemplary embodiment, controller 22 (or at least one subcontroller) is mounted to air manifold 16, e.g., vertically adjacent exhaust opening(s) 92. Thus, the gas exiting the air manifold, e.g., concentrated nitrogen, may be directed across or otherwise towards the controller for cooling its components. Brackets or other supports (not shown) may be mounted to manifold cap 60 and the circuit board(s) and/or other components of controller 22 may be secured by the brackets or support in a conventional manner.

Batteries 148 are inserted into the apparatus 10 at any time, e.g., after access to the interior is no longer needed. The side regions between manifolds 16, 102 may remain substantially open (other than any area covered by batteries 148), e.g., to provide access during assembly and/or testing of the components of the apparatus. Optionally, a relatively thin and/or light-weight skin or other structure (not shown) may be provided in each of the open side regions to substantially enclose the interior of the apparatus 10, e.g., to limit access and/or protect the components therein, or reduce noise transmission and sound level.

G. Operation of the Apparatus

Returning to FIG. 3, the basic operation of apparatus 10 will now be described. Generally, the operation of the apparatus has two aspects, concentrating oxygen from ambient air by adsorption within the sieve beds, and delivering concentrated oxygen to a user from the reservoir, each of which is described below. Each aspect of the apparatus may operate independently of the other, or they may be interrelated, e.g., based upon one or more related parameters.

Apparatus may be operated using one or more optional methods, such as those described below, to increase efficiency or other performance characteristics of the apparatus. For example, based upon measurements of pressure and/or oxygen purity, the operating conditions of the apparatus may be adjusted to increase oxygen purity and/or concentration, output flow rate and/or pressure, reduce power consumption, and the like.

In exemplary embodiments, apparatus 10 has the capability to deliver up to about 0.9 or 1.2 liters per minute (lpm) equivalent of pure oxygen. As used herein, equivalent flow rates are used, which correspond substantially to the amount of pure (100%) oxygen gas delivered per unit of time. Because apparatus 10 concentrates oxygen by adsorption from ambient air, the apparatus does not generate pure oxygen for delivery to a user. Instead, the gas that escapes from sieve beds 12 that is stored in reservoir 18 has a maximum concentration of oxygen of about ninety five percent (95.4%), with the rest of the gas being argon and other trace gases (about 4.6%).

Figure 12:
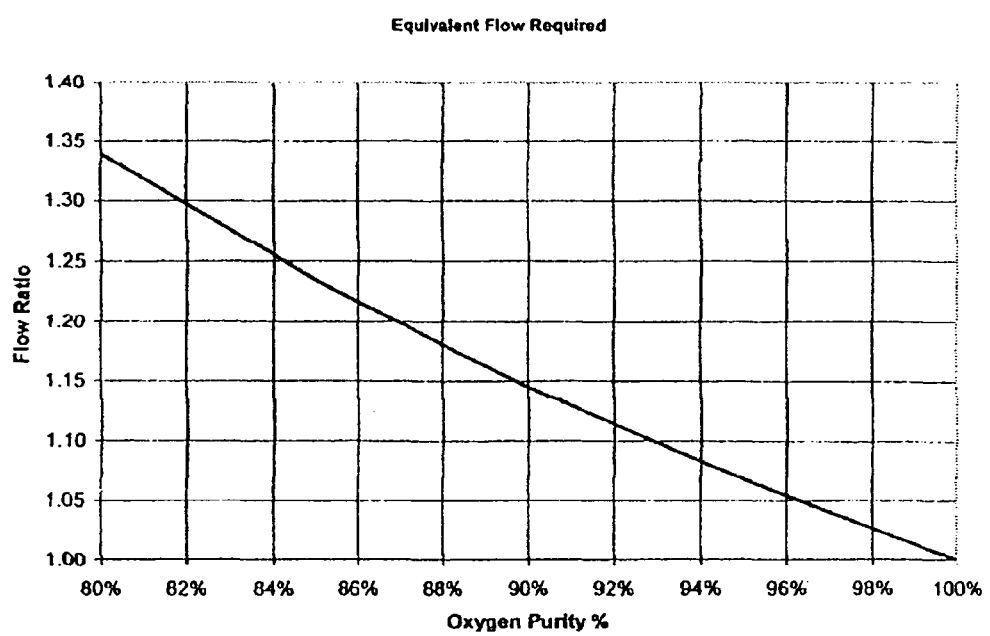
FIG. 12 is a graph illustrating the relationship between the flow ratio and oxygen purity.

At a given flow rate, the actual amount of concentrated oxygen delivered by apparatus 10 may be less than for pure oxygen. Thus, concentrated oxygen may have less therapeutic value than pure oxygen. To compensate for this deficit and provide equivalent volumes of oxygen, the flow rate of concentrated oxygen must be higher than for pure oxygen. The Ratio of delivered concentrated oxygen to equivalent pure oxygen is expressed in Equation (1) below:

$$\text{Ratio} = (100\% - 21\%)/(\text{actual purity} - 21\%), \quad (1)$$

and is as shown in FIG. 12. For example, 1.05 lpm of 88% concentrated oxygen may be substantially equivalent to 0.9 lpm of pure oxygen, and 1.4 lpm of 88% concentrated oxygen may be substantially equivalent to 1.2 lpm of pure oxygen.

Figure 13:
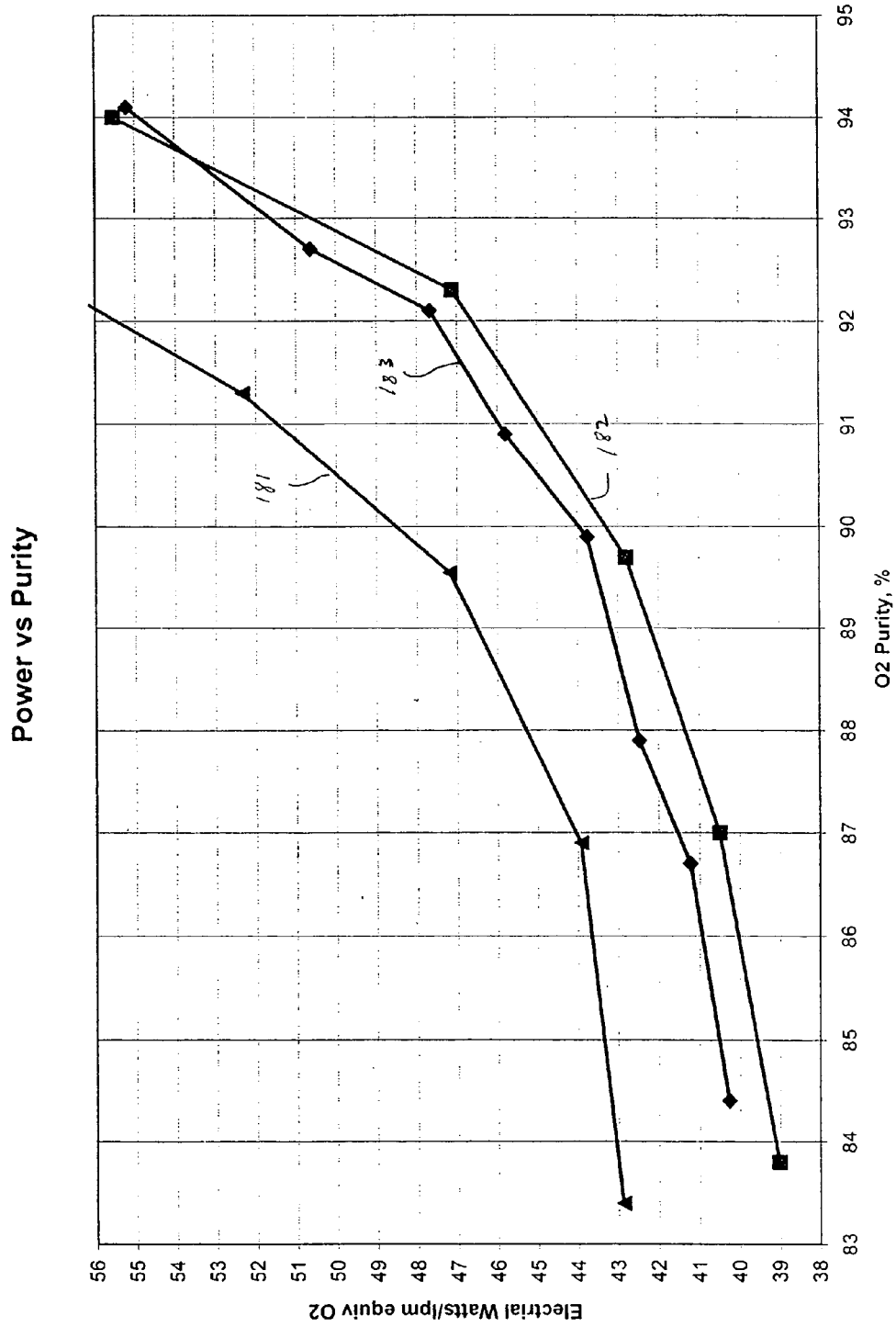
FIGS. 13 and 14 are graphs illustrating the power consumption versus purity.
Figure 14:
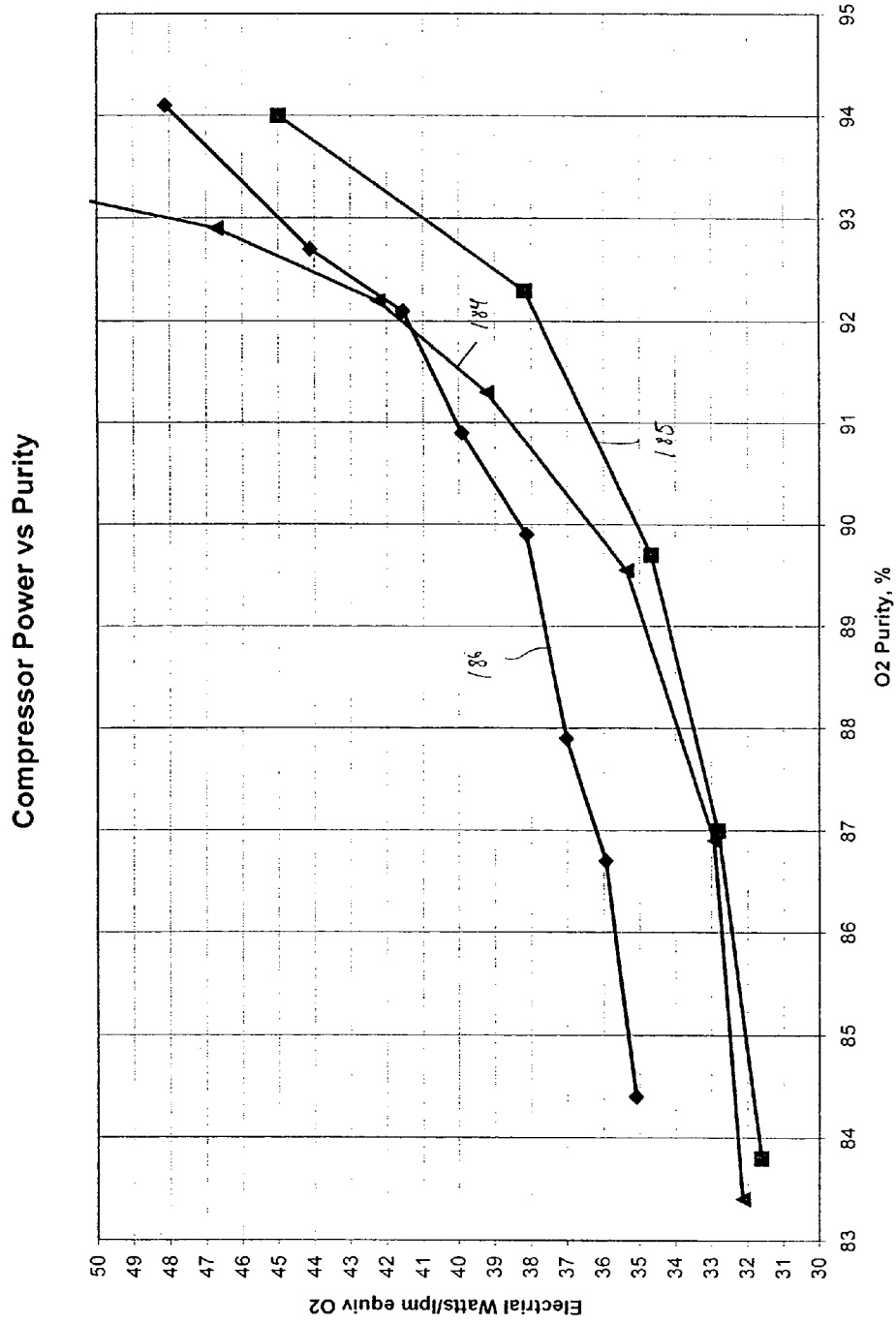

Testing has shown that compensating for purity by increasing the flow rate may reduce overall power consumption for apparatus 10. For example, FIGS. 13 and 14 illustrate the relationship between power consumption and the purity of the oxygen output by apparatus 10. More specifically, FIG. 13 shows the relationship between the total power consumed by the device at different levels of oxygen purities, and FIG. 14 shows the relationship between the power consumed only by compressor 14 at different levels of oxygen purities. Curves 181, 182, and 183 represent the total power versus oxygen purity relationship at various flow settings. Curve 181 corresponds to a flow setting of 2, which is equivalent to 400 cubic centimeters (cc) of oxygen per minute, curve 182 corresponds to a flow setting of 3, which is equivalent to 600 cc/min, and curve 183 corresponds to a flow setting of 4.5, which is equivalent to 900 cc/min. Curves 184, 185, and 186 represent the total power versus oxygen purity relationship at various flow settings. Curve 184 corresponds to a flow setting of 2 (300 cc/min), curve 185 corresponds to a flow setting of 3 (600 cc/min), and curve 186 corresponds to a flow setting of 4.5 (900 cc/min).

It can be appreciated from reviewing FIGS. 13 and 14 that as the oxygen purity increases, the power needed to make the oxygen increases exponentially. At some point, it becomes too "costly" in terms of power consumption to generate higher purities of oxygen. Similarly, as the oxygen purity is decreased from approximately 87-90%, relatively little power consumption is gained. That is, further decreases in oxygen purity below 87-90% do not provide much benefit in terms if power consumption, i.e., longer battery duration. Stated another way, there are diminishing marginal returns in terms of power consumption for decreases in oxygen purity beyond 87-90%. The present inventors determined that when the competing values of oxygen purity and power consumption are balanced, oxygen purities between about 85-90% result in desirable efficiencies, with 88% being deemed an exemplary target oxygen purity for the gas delivered by apparatus 10.

Figure 15:
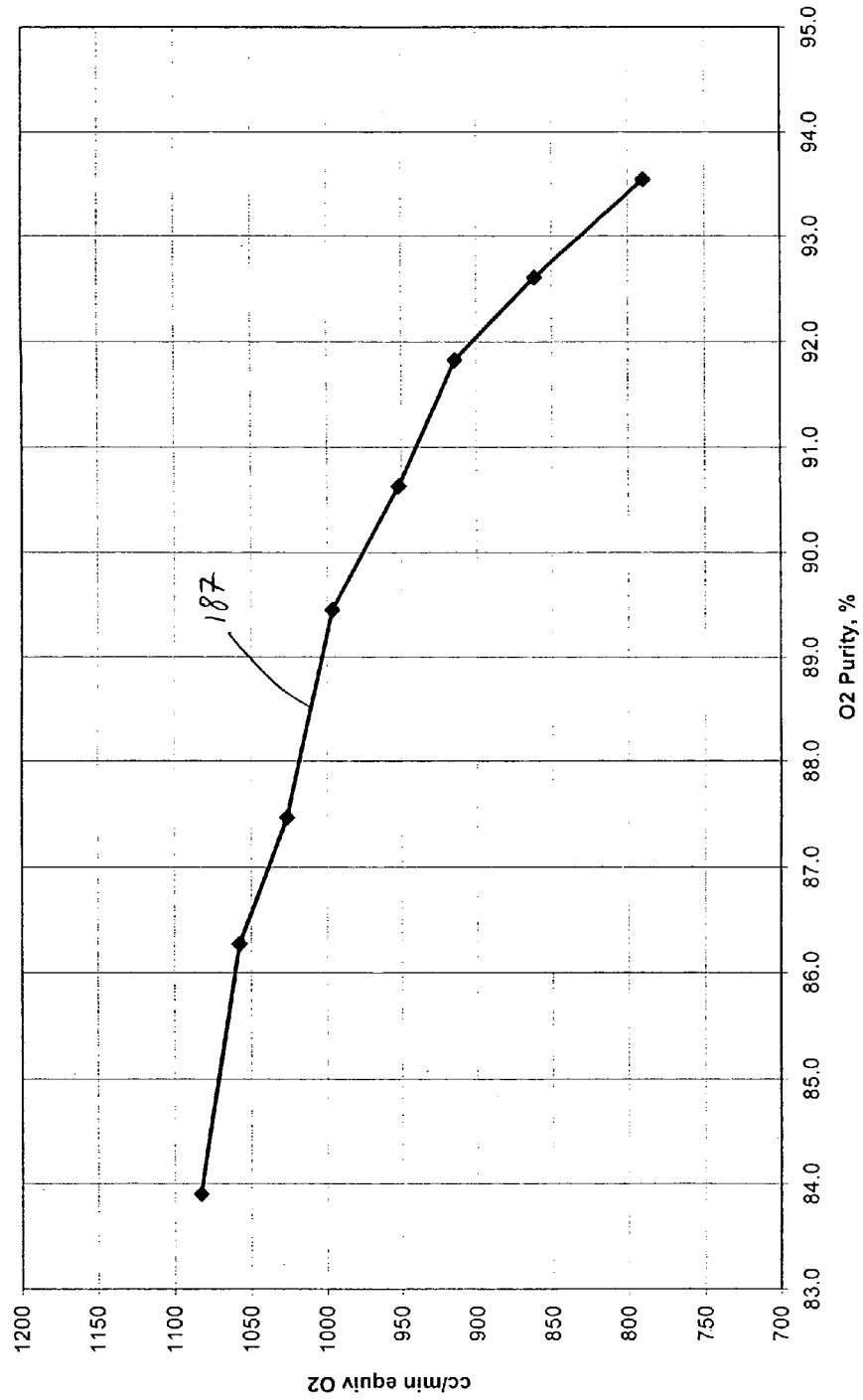
FIG. 15 is a graph illustrating the relationship between oxygen output and oxygen purity levels.

FIG. 15 illustrates the relationship between the amount of oxygen produced and the oxygen purity. Curve 187 represents the 100% oxygen equivalent or molecules of oxygen generated over a range of purity levels. It can be appreciated from this figure that as the oxygen purity increases, for example, above 90-91%, less molecules of oxygen are made by apparatus 10. Similarly, as the purity is reduced, e.g., below 87-88%, there is very little additional molecules of oxygen generated. Stated another way, there are diminishing marginal returns in terms of oxygen generated for purities below 87-88%. Thus, the present inventors deemed that the ideal "sweet spot" in terms of oxygen purity is in a range of 85-90%.

FIG. 16 is a table of the data used to generate the curves in FIGS. 13-15. It should also be notes that volts and amps used by the system without the compressor operating but with the cooling fan (intake fan 164) operating is: V=18.1 V, A=0.31 A, for a total power of 5.6 W. Without the compressor or the cooling fan operating, the volts and amps used by the system is: V=18.1 V, A=0.14 A, for a total power of 2.5 W. Thus, the fan alone uses approximately 3.1 W of power.

1. Driving the Sieve Beds

Generally, to generate concentrated oxygen, which may be stored in reservoir 18 and/or delivered directly to the user, apparatus 10 is operated such that sieve beds 12 are alternatively "charged" and "purged." When a sieve bed is being charged or pressurized, compressed ambient air is delivered from the compressor into air inlet/outlet end 32 of the sieve bed, causing the sieve material to adsorb more nitrogen than oxygen as the sieve bed is pressurized. While the nitrogen is substantially adsorbed by the sieve material, oxygen escapes through oxygen inlet/outlet end 34 of the sieve bed, where it may be stored in the reservoir and/or be delivered to the user.

Once the pressure within the sieve bed reaches a predetermined limit (or after a predetermined time), the sieve bed may then be purged or exhausted, i.e., air inlet/outlet end 32 may be exposed to ambient pressure. This causes the compressed nitrogen within the sieve bed to escape through air inlet/outlet end 32, e.g., to pass through air manifold 16 and exit exhaust opening(s) 92. Optionally, as the sieve bed 12A is being purged, oxygen escaping from the other sieve bed 12B (which may be being charged simultaneously) may pass through purge orifice 81 into oxygen inlet/outlet end 34 of purging sieve bed 12A, 12B, e.g., if the pressure within the charging sieve bed is greater than within the purging sieve bed, which may occur towards the end of purging. In addition or alternatively, oxygen may pass through check valves 110 between the sieve beds, e.g., when the relative pressures of the sieve beds and the reservoir causes check valves 110 to open, in addition to or instead of through purge orifice 81. This oxygen delivery into oxygen inlet/outlet end 34 of sieve bed being purged may assist evacuating the concentrated nitrogen out of the sieve bed before it is charged again.

The size of purge orifice 81 is selected to allow a predetermined oxygen flow rate between the charging and purging sieve beds 12. It is generally desirable that the flow through the purge orifice is equal in both directions, such that both sieve beds 12A and 12B are equally purged, e.g., by providing a purge orifice having a geometry that is substantially symmetrical. In an exemplary embodiment, purge orifice 81 may have a diameter or other equivalent cross-sectional size of about 0.02 inch (0.5 mm) such that about 2.6 lpm may pass therethrough at about five pounds per square inch (5 psi) pressure difference across the purge orifice. This capacity of purge orifice 81 may not correspond to the actual volume of oxygen that may flow between the sieve beds during operation of the apparatus, because the actual flow may be based of the pressure difference between the charging and purging sieve beds 12, which changes dynamically based upon the various states of the apparatus.

In an exemplary embodiment, shown in Table 1 below, apparatus 10 is operated using a process that includes four (4) states "1" and "0" represent open and closed states of air control valves 20, respectively.

TABLE 1

| State | Time | Description | Valve $20a_s$ | Valve $20a_e$ | Valve $20b_s$ | Valve $20b_e$ |
|---|---|---|---|---|---|---|
| 1 | Time Pressurize ~6 sec. | Pressurize 12A Exhaust 12B | 1 | 0 | 0 | 1 |
| 2 | Time Overlap ~0.2 sec | Pressurize both 12A and 12B | 1 | 0 | 1 | 0 |
| 3 | Time Pressurize ~6 sec. | Pressurize 12B Exhaust 12A | 0 | 1 | 1 | 0 |
| 4 | Time Overlap ~0.2 sec | Pressurize both 12A and 12B | 1 | 0 | 1 | 0 |

During state 1, sieve bed 12A is being charged and sieve bed 12B is being purged. As shown in the table, supply air control valve $20a_s$ and exhaust air control valve $20b_e$ are open, and supply air control valve $20b_s$ and exhaust air control valve $20a_e$ are closed. With additional reference to FIG. 7, with this valve arrangement, sieve bed 12A communicates with compressor 14 via compressor outlet passage 64 and sieve passage 66a, while sieve bed 12B communicates with exhaust opening(s) 92 via sieve bed passage 66b and exhaust passage 68. At the end of state 1, as the pressure within sieve bed 12A exceeds the pressure within sieve bed 12B, purge orifice 81 provides a low flow of oxygen gas to flush remaining nitrogen from sieve bed 12B. State 3 is the mirror image of State 1, i.e., sieve bed 12B is being charged and sieve bed 12A is being purged.

The duration of States 1 and 3 (Time Pressurize) may be set based upon one or more parameters, such as the size of purge orifice 81, the purity of oxygen leaving sieve beds 12, pressure within reservoir 18, and the like, as described further elsewhere herein. For example, during State 1, if Time Pressurize is too long, all remaining nitrogen in sieve bed 122B (which is being purged) may be purged, and oxygen from sieve bed 12A (which is being charged) passing through the purge orifice 81 into sieve bed 12B may escape out the exhaust opening(s) 92, wasting oxygen. If Time Pressurize is too short, nitrogen may remain in sieve bed 12B at the end of the purge cycle, which may reduce the efficiency of sieve bed 12B when it is subsequently charged. Thus, it may be desirable to hold the size of purge orifice 81 to a very tight flow tolerance, and manufacture sieve beds 12 under strict control, such that the sieve beds is consistent within allowable tolerances without having to adjust Time Pressurize during and/or after manufacturing.

During State 2, supply air control valve $20b_s$ is opened and exhaust air control valve $20a_e$ is closed. This allows pressurized air from sieve bed 12A to flow into sieve bed 12B through the purge orifice 81. Generally, State 2 is relatively short compared to States 1 and 3, e.g., such that pressurized air enters sieve bed 12B before concentrated nitrogen within sieve bed 12A begins to enter sieve bed 12B. State 2 may reduce the amount of compressed air that must be delivered from the compressor 14 before State 3, which may improve overall efficiency of the apparatus 10. Similarly, during State 4, supply air control valve 20 as is opened and exhaust air control valve $20b_e$ is closed. Thus, during State 4, compressed air flows from sieve bed 12B to sieve bed 12A before sieve bed 12A is charged (when State 1 is repeated).

In the embodiment shown in Table 1 above, the durations (Time Overlap) of States 2 and 4 are substantially shorter than the durations (Time Pressurize) of States 1 and 3. For example, the durations (Time Overlap) of States 2 and 4 may be not more than about 1.5 seconds or not more than about 0.6 second, while the durations (Time Pressurize) of States 1 and 3 may be at least about four (4) seconds or at least about five (5) seconds.

Optionally, the durations may be varied, for example, as user demand (e.g., dose setting and/or breathing rate) and/or other parameters warrant the change(s). Alternatively, the durations (Time Pressurize and Time Overlap) may be fixed when the controller 22 is initially programmed and/or subsequently serviced. In either case, times or time constants may be saved in flash-type memory or other memory associated with controller 22. If desired, the times or time constants may be adjusted, e.g., via a serial connection during initial manufacturing, in a subsequent service environment, and/or during use, and the new values may be stored within the memory.

For example, it may be desirable to reduce the durations of States 1 and 3 (Time Pressurize) as the pressure within the reservoir 18 ("reservoir pressure" or $P_{res}$) increases. As the reservoir pressure increases, the higher pressure may drive more gas through purge orifice 81, reducing the amount of time required to substantially exhaust nitrogen from sieve bed 12A, 12B being purged. An equation may be created to determine the optimum time (Time Pressurize) based upon the reservoir pressure. For example, the equation may be estimated based upon a linear relationship:

$$\text{Time Pressurize} = k * P_{res}, \quad (2)$$

where k is a constant that may be determined theoretically or empirically. Alternatively, a more complicated equation may be developed, e.g., based upon empirical testing. The duration of States 2 and 4 (Time Overlap) may also be fixed or adjusted during manufacturing or servicing, and/or dynamically during operation of apparatus 10, if desired, in a similar manner.

Optionally, one or more check valves (not shown) may be provided in the exhaust line (e.g., within exhaust passage 68 in air manifold 16 or coupled to the exhaust opening(s) 92). Such a check valve may stop sieve beds 12 from "breathing," e.g., when apparatus 10 is not operational, and is subjected to changing barometric pressure and/or temperature. For example, if SMC DXT valves are provided for exhaust air control valves $20_e$, they may act as check valves. Without pilot pressure, however, exhaust air control valves 20e may leak. Relatively small springs (not shown) may be added to these valves to prevent such leakage.

Alternatively, one or more valves (not shown) may be provided in parallel with or instead of purge orifice 81, i.e., in lines extending between the oxygen inlet/outlet ends 34 of sieve beds 12. In this alternative, apparatus 10 may be operated using a four (4) state cycle similar to that described above. However, the parallel valves may open during the overlap time or at the end of the pressure cycle in order to actively control pressurization or purging of sieve beds 12.

The technique used to determine the target pressure and valve timing, i.e., the duration of the charge/purge cycles, according to the principles of the present invention are discussed below with reference to FIGS. 17-20. As used below "Valve Time" refers to the during of the charge cycle or the purge cycle. The present invention sets the valve timing so as to achieve the beneficial features of the present invention, namely a light-weight, high-output, long battery life, ambulatory oxygen concentrator. The Valve Time is optimized empirically at different oxygen production levels. Higher pressure in the sieve beds yields a shorter ideal valve time. It is believed that this is because the higher pressure generates higher flows through the purge orifice, which purges the exhausting bed faster.

Figure 17:
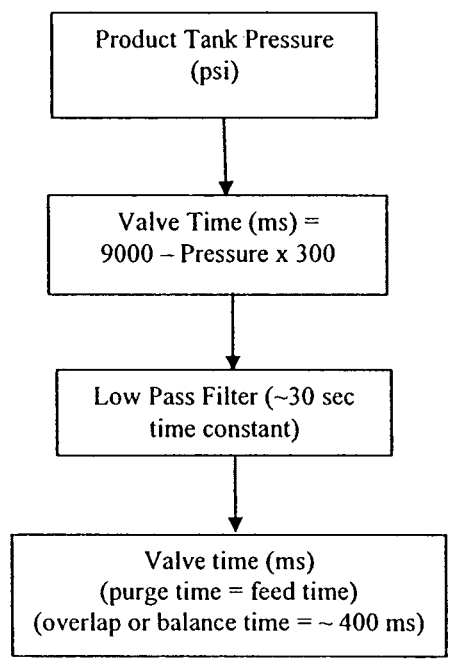
FIG. 17 is a flow chart illustrating the process for setting the Valve Time used in the process for driving the sieve beds.
Figure 18:
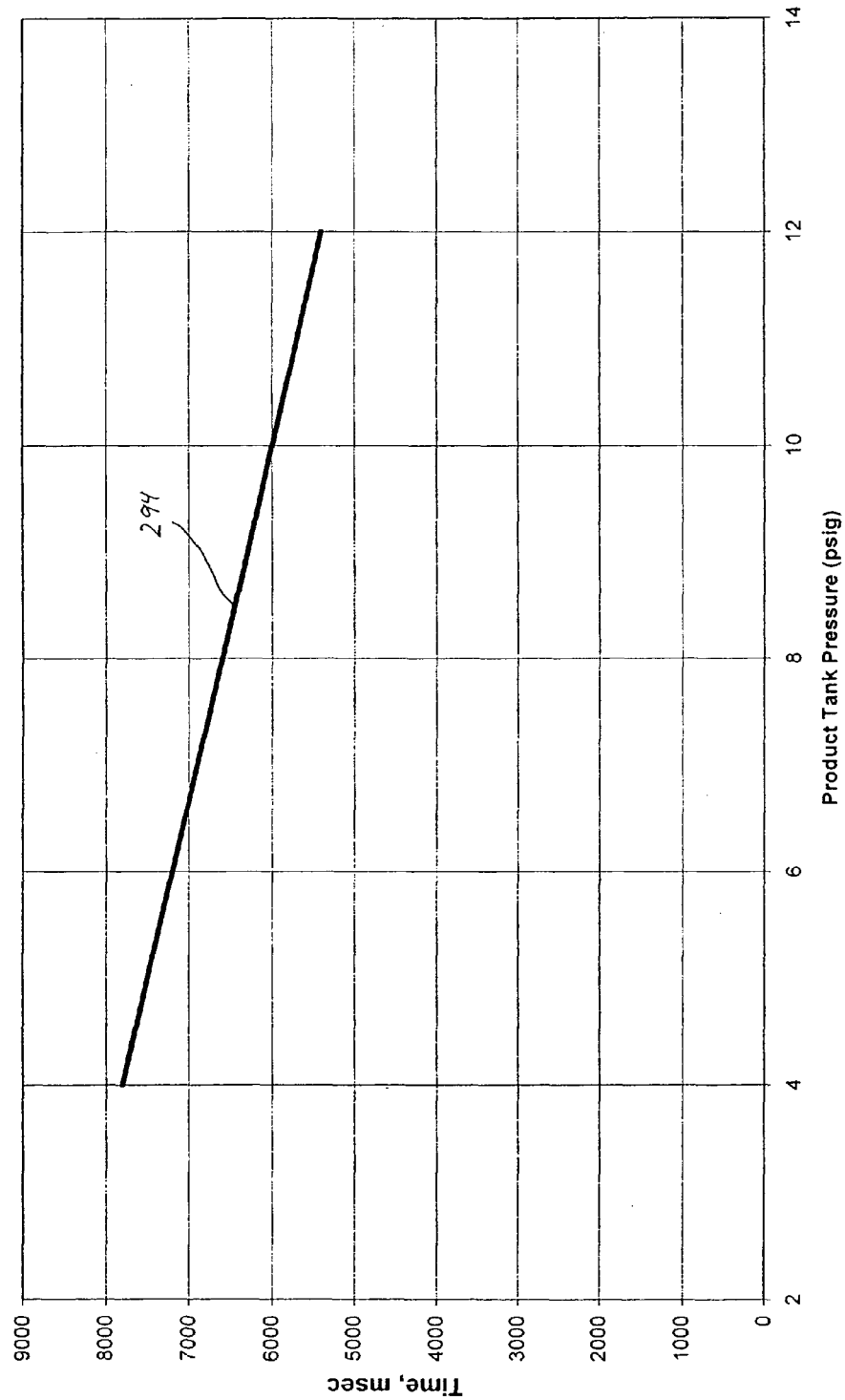
FIG. 18 is a graph illustrating the relationship between the sieve bed/product tank pressure and Valve Time.

As shown in FIG. 17, the Valve Time is determined in step 290 by first determining the pressure of the product tank/reservoir 18, which is determined based on the output of pressure sensor 114. It should be noted that tank/reservoir 18 is used in place of the sieve bed pressure because they are substantially the same. Of course, the sieve bed pressure could also be used. In step 292, the Valve Time (ms) is determined according to the relationship between valve time and pressure, which is graphically illustrated in FIG. 18 as curve 294. The equation that defines the Valve Time and that corresponds to curve 294 is defined as follows:

$$\text{Valve Time (ms)} = 9000 - \text{Pressure} \times 300, \quad (3)$$

In step 296, the Valve Time computed in step 232 is low pass filter to stabilize its value over a period of time and the Valve Time is provided in step 298. The purpose of the low pass filtering the Valve Time is to prevent it from changing too abruptly, as this can lead to instability and poor system performance. Thus, the charge time and the purge time are set based on the Valve Time determined in step 298.

Between each bed cycle, there is a short (~400 ms) time when both pressurize valves are open and both exhaust valves are closed. This allows pressurized air, not depleted of oxygen yet, to be transferred from the bed coming off of its pressurize cycle to the bed just starting its cycle, reducing the required compressor airflow and hence power. Currently, this time is fixed, but it could be adjusted slightly relative to system pressure for optimized performance.

2. Oxygen Delivery to User

With concentrated oxygen stored in the reservoir 18 and/or with the sieve beds 12A, 12B separating oxygen from ambient air, the apparatus 10 may be used to deliver concentrated oxygen to a user. As described above, controller 22 may be coupled to oxygen delivery valve 116 for opening and closing the oxygen delivery valve to deliver oxygen from reservoir 18 to a user of apparatus 10.

In an exemplary embodiment, controller 22 may periodically open the oxygen delivery valve 116 for predetermined "pulses." During pulse delivery, a "bolus" of oxygen is delivered to the user, i.e., oxygen delivery valve 116 is opened for a predetermined pulse duration, and thereafter closed until the next bolus is to be delivered. Alternatively, controller 22 may open oxygen delivery valve 116 for continuous delivery, e.g., throttling the oxygen delivery valve to adjust the flow rate to the user. In a further alternative, controller 22 may periodically open and throttle oxygen delivery valve 116 for a predetermined time to vary the volume of the bolus delivered.

In one embodiment, controller 22 may open oxygen delivery valve 116 after the controller detects an event, such as detecting when the user begins to inhale. When the event is detected, oxygen delivery valve 116 may be opened for the predetermined pulse duration. In this embodiment, the pulse frequency or spacing (time between successive opening of the oxygen delivery valve) may be governed by and correspond to the breathing rate of the user (or other event spacing). The overall flow rate of oxygen being delivered to the user is then based upon the pulse duration and pulse frequency.

Optionally, controller 22 may delay opening oxygen delivery valve 116 for a predetermined time or delay after the user begins to inhale, e.g., to maximize delivery of oxygen to the user. For example, this delay may be used to maximize delivery of oxygen during the "functional" part of inhalation. The functional part of the inhalation is the portion where most of the oxygen inhaled is absorbed into the bloodstream by the lungs, rather than simply used to fill anatomical dead space, e.g., within the lungs. It has been found that the functional part of inhalation may be approximately the first half and/or the first six hundred milliseconds (600 ms) of each breath. Thus, the predetermined delay after detecting inhalation may be between about twenty and one hundred fifty milliseconds (20-150 ms).

Thus, it may be particularly useful to detect the onset of inhalation early and begin delivering oxygen quickly in order to deliver oxygen during the functional part of inhalation. A user breathing through their nose may generate relatively strong pressure drops, e.g., about one centimeter of water (1 $cmH_2O$), within the cannula. However, if the user breathes through their mouth, they may only generate pressure drops on the order of 0.1 centimeter of water (0.1 $cmH_2O$).

For example, assuming an excitation voltage of five volts (5 V), the output sensitivity of the pressure sensor 122 may be about 320 $\mu V/cmH_2O$. Consequently, a pressure drop of 0.1 V (e.g., from inhalation through the mouth). If the controller 22 includes an amplifier (not shown) having a gain of one thousand (1,000), the amplifier would create an amplified signal of about thirty-two millivolts (32 mV), which may provide six (6) counts in a ten (10) bit five volt (5 V) analog to digital (A/D) converter.

As explained above, pressure sensor 122 may exhibit drift problems, making it difficult for controller 22 to identify the beginning of an inhalation and open oxygen delivery valve 116. One solution is to reset or zero pressure sensor 122 when apparatus 10 is off. However, the pressure sensor may be temperature sensitive such that the pressure sensor may create a drift greater than the trigger level. Alternatively, as described above, a small valve (not shown) may be coupled to pressure sensor 122 that may be opened periodically to reset or zero the pressure sensor, e.g., while oxygen delivery valve 116 is open and delivering oxygen. In a further alternative, also described above, a relatively small orifice may be provided between pressure sensor 122 and oxygen delivery valve 116 that may allow the pressure sensor to reset or zero during oxygen delivery, e.g., during a pulse as short as one hundred milliseconds (100 ms).

In yet a further alternative, controller 22 includes hardware and/or software that filters the signals from pressure sensor 122 to determine when the user begins inhalation. In this alternative, controller 22 may need to be sufficiently sensitive to trigger oxygen delivery valve 116 properly, e.g., while the user employs different breathing techniques. For example, some users may practice pursed lip breathing, e.g., inhaling through their nose and exhaling through pursed lips. During this breathing technique, controller 22 will not detect an expiratory signal that will indicate that inhalation is about to begin.

The filtering algorithm may also need to distinguish between the onset of inhalation and a declining rate of exhalation, which may otherwise mislead the controller into triggering oxygen delivery during a long period of exhalation (which is wasteful). In addition or alternatively, the filtering algorithm of controller 22 may need to "hold off" during long breaths, e.g., to avoid delivering multiple pulses during a relatively long single inhalation. For example, if the controller is configured to open oxygen delivery valve 116 if it detects a pressure drop below a predetermined threshold, it may open the oxygen delivery valve twice during a single inhalation (which may also be wasteful). In this situation, the filtering algorithm time after inhalation is sensed, e.g., at least about 1.5 seconds.

Alternatively, controller 22 may open the oxygen delivery valve at a pulse frequency that is fixed, i.e., independent of the user's breathing rate, or that may be dynamically adjusted. For example, the controller may open oxygen delivery valve 116 in anticipation of inhalation, e.g., based upon monitoring the average or instantaneous spacing or frequency of two or more previous breaths. In a further alternative, the controller may open and close oxygen delivery valve 116 based upon a combination of these parameters, e.g., based upon the user's breathing rate, but opening the oxygen delivery valve if a minimum predetermined frequency is not met.

For pulse delivery, the pulse duration may be based upon the dose setting selected by the user. In this way, substantially the same volume of oxygen may be delivered to the user each time oxygen delivery valve 116 is opened, given a specific dose setting. The dose setting may be a quantitative or qualitative setting that the user may select. A qualitative dose setting may involve a dial or one or more buttons (e.g., on user interface 144) that allows the user to select a level, e.g., on a scale from one to ten (1-10) or from range between a minimum and a maximum value. Controller 22 may relate the qualitative setting with a desired flow rate or bolus size, e.g., relating to the maximum flow capacity of apparatus 10.

For example, the settings may correspond to points within the range at which the apparatus 10 may supply concentrated oxygen, e.g., between zero and one hundred percent (0-100%) of a maximum capacity of the apparatus. For example, a maximum flow rate (or equivalent flow rate of pure oxygen) for apparatus 10 may be used, e.g., between about six and sixteen liters per minute (6-16 lpm). Alternatively, a maximum bolus volume may be used, e.g., between about ten and one hundred fifty milliliters (10-150 ml) or between about ten and eighty milliliters (10-80 ml).

A quantitative setting may allow a user to select a desired flow rate (e.g., in lpm), which may be an actual concentrated oxygen flow rate or an equivalent pure oxygen flow rate, or a desired bolus volume (e.g., in milliliters). The flow rates or volumes available for selection may also be limited by the capacity of the apparatus 10, similar to the qualitative settings. Additional information on using a volume-based dose setting system, rather than implying equivalency to continuous flow, may be found in *Characteristics of Demand Oxygen Delivery Systems: Maximum Output and Setting Recommendations*, by P. L. Bliss, R. W. McCoy, and A. B. Adams, Respiratory Care 2004; 49(2) 160-165, the entire disclosure of which is incorporated by reference herein.

As the dose setting is increased, the pulse duration may be increased, e.g., from about fifty to five hundred milliseconds (50-500 ms) to deliver a predetermined bolus during each pulse. If the user's breathing rate remains substantially constant, the pulse frequency may also remain substantially constant, thereby increasing the overall flow rate being delivered to the user. During actual use, however, the user's breathing rate may change, e.g., based upon level of activity, environmental conditions, and the like. For example, breathing rates for lung disease patients may vary from about thirteen to forty (13-40) breaths per minute, or from about eighteen to thirty (18-30) breaths per minute. Therefore, apparatus 10 may be capable of delivering these frequencies of pulses to the user.

Because of the relatively small size of a portable concentrator, such as apparatus 10, conditions may occur in which the dose setting and user's breathing rate exceed the capacity of the apparatus. Thus, for any given dose setting, i.e., particular volume (e.g., ml) per breath, the apparatus may have a maximum breathing rate at which the apparatus may deliver oxygen at the desired dose setting.

If the maximum breathing rate for a particular dose setting is exceeded, the apparatus may respond in one or more ways. For example, apparatus 10 may include an alarm, e.g., a visual and/or audio alarm, that may alert the user when such an event occurs. This may alert the user, and, if necessary, the user may slow their breathing rate, e.g., by resting and the like.

In addition or alternatively, apparatus 10 may change the delivery parameters to maintain delivery at or near the maximum flow rate capacity of the apparatus, e.g., about 900 ml/min. or about 1,200 ml/min. To achieve this, controller 22 calculates the bolus size that may be delivered given the user's breathing rate (e.g., dividing the maximum flow rate by the breathing rate or using a lookup table), and adjust the pulse duration accordingly (and/or throttle oxygen delivery valve 116). For example, assume controller 22 detects that the user has a breathing rate of about twenty-three (23) breaths per minute over a predetermined time, e.g., the most recent thirty seconds (30 sec), and the dose setting delivers forty millimeters (40 ml) per breath. The resulting flow rate, 920 ml/min, would exceed the ability of a 900 ml/ml. capacity apparatus. Consequently, controller 22 may reduce the pulse duration to reduce the flow rate at or below 900 ml/min, e.g., by reducing the pulse duration by at least about (1900/920) or about two percent (2%).

When selecting volumetric flow rates for pulse delivery, one or more additional factors may also be considered. For example, higher flow rates may create greater back pressure in the cannula, making control of the flow more difficult, especially in a relatively low pressure system, such as a portable oxygen concentrator, similar to apparatus 10 described herein.

Optionally, apparatus 10 may be operated in a manner that may maximize efficiency, 10 e.g., to reduce power consumption and extend battery life of the apparatus. This may enhance the mobility of the user, e.g., allowing them to remain independent of an external power source for longer periods of time.

Several variables may be relevant to determine how much energy may be required to operate apparatus 10. The independent variable is the speed or power of compressor 14, which may consume as much as ninety five percent (95%) of the power used by the apparatus. The speed of motor 40 of the compressor may be controlled by controller 22, and is essentially a pulse width modulation ("PWM") of the power of battery 148, i.e., the more power required, the higher the duty cycle of the PWM.

Closed loop speed or torque control of motor 40 may be used, but may not be necessary. During the process cycle, as pressure increases, the speed of the motor of compressor 14 may be reduced because of the higher torque requirement. This may result in the total energy required being substantially leveled, minimizing current peaks.

During the process cycle, when the sieve bed feed valve is open and the pressure of the sieve bed/product tank increases toward the target pressure, the motor is not controlled to a fixed speed. Instead, the motor speed is allowed to fall, but the current/power provided to the motor is limited. By limiting current/power to the motor, this maximizes the consumption of the battery, i.e., battery life. This is so, because the discharge current rate of the battery is lowered and therefore the run time of the battery of the enhanced/maximized.

The PWM may be expressed as a percentage from zero to one hundred percent (0-100%), zero corresponding to compressor 14 being off and one hundred percent corresponding to the compressor operating at its maximum speed. In practice, there is a minimum value attainable, below which compressor 14 may not turn, and therefore, the true range may be about forty to one hundred percent (40-100%). The equations here assume the relationships are linear, which may provide sufficient approximation. Alternatively, more detailed equations may be developed based upon theoretical or empirical calculations, e.g., which may be implemented using a non-linear equation or a lookup table, e.g., within memory of controller 22.

PWM may be controlled by monitoring reservoir pressure (pressure within reservoir 18) and controlling motor 40 of the compressor to maintain a target reservoir pressure. For example, controller 22 may be coupled to pressure sensor 114 within the reservoir to monitor the reservoir pressure, and the controller may adjust the PWM of the motor accordingly. The target reservoir pressure may be static, e.g., set during manufacturing or service, or may be dynamic, e.g., changed to maintain a target oxygen purity and/or other parameter(s), as described further elsewhere herein. Alternatively, multiple variables may be monitored and motor 40 controlled to maintain the multiple variables at selected targets.

For example, a target reservoir pressure may be selected based upon dose setting and user breathing rate. In exemplary embodiments, the target reservoir pressure is between about five and fifteen pounds per square inch (5-15 psi) or between about six and twelve pounds per square inch (6-12 psi). Optionally, the target pressure may be adjusted based upon other parameters, such as oxygen purity, as explained further below.

The user breathing rate may be determined by controller 22, e.g., based upon pressure readings from pressure sensor 122. The pressure sensor may detect a reduction in pressure as the user inhales (e.g., drawing oxygen from recesses 133, 137 and channel 135, shown in FIGS. 9A and 9B). Controller 22 may monitor the frequency at which pressure sensor 122 detects the reduction in pressure to determine the breathing rate. In addition, the controller may also use the pressure differential detected by pressure sensor 120.

As the dose setting is increased, the user breathing rate increases, and/or the battery voltage drops, the product reservoir pressure may tend to drop. To compensate for this pressure drop, PWM may be increased. Thus, a target reservoir pressure may be chosen and controller 22 may implement a control loop to maintain this target reservoir pressure.

Figure 19:
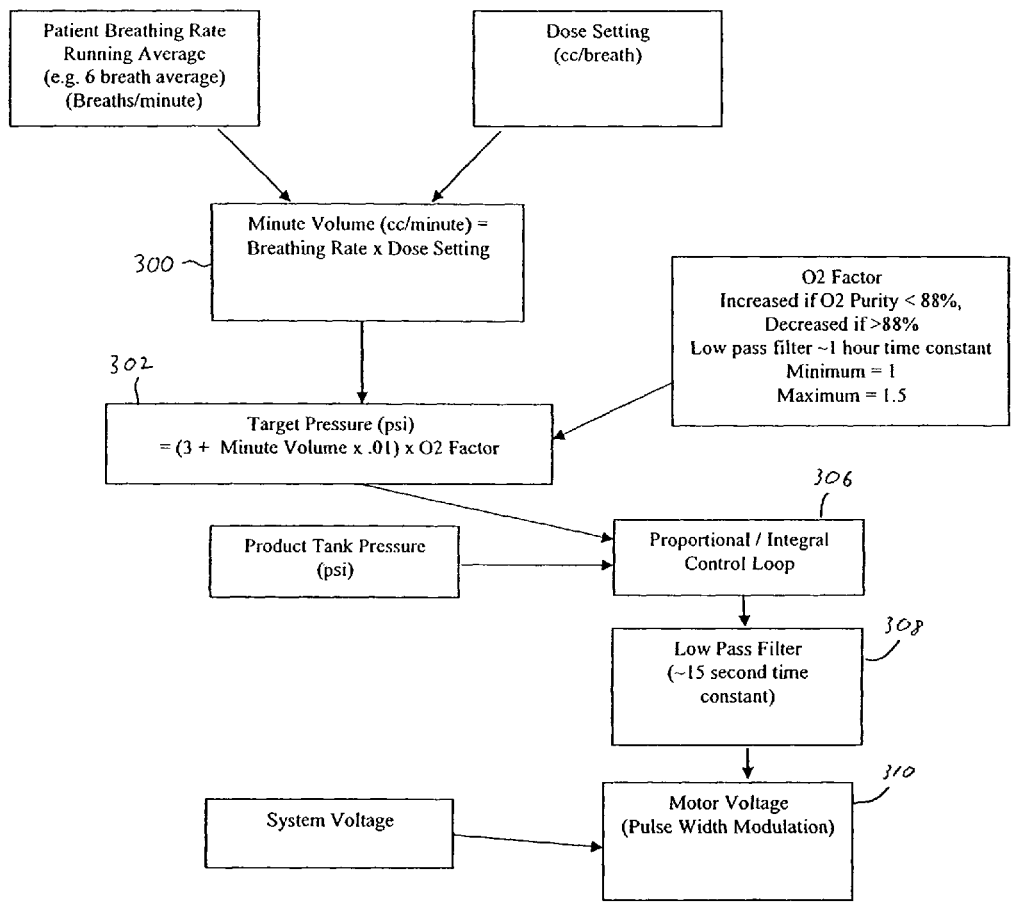
FIG. 19 is a flow chart explaining the control of the motor in the compressor used in the apparatus of the present invention.

FIG. 19 illustrates an example of a process apparatus 10 uses to control the speed of motor 40 in compressor 14. The present invention controls the speed of motor 40 so as to maintain an averaged Target Pressure in product tank or reservoir 18. It should be noted that the motor speed is not sensed or determined, if monitored at all, it is done only for informational purposes. It should also be noted that the motor speed, per se, is not being controlled. Instead, the process illustrated in FIG. 19 is used to adjust the voltage provided to the motor, which may or may not change the motor speed, depending, for example, in the torque the motor is experiencing.

In step 300, oxygen demand (minute volume) is determined by the pulse or dose setting and averaged patient breathing rate. In step 302, minute volume is used to calculate the target product tank pressure ("Target Pressure") according to the relationship given in this step. This relationship between minute volume and the Target Pressure is shown graphically in FIG. 20 as curve 303. A higher Target Pressure is required for higher oxygen production. The Target Pressure has been determined empirically to be high enough, with some safety factor, to produce oxygen across the range of minute volume.

The Target Pressure is further modified slowly (over hours of operation) by the product output purity. This modifier is called "$O_2$ Factor". See step 304 in FIG. 19. The $O_2$ factor has a minimum of 1, so that the initial default target pressure cannot be reduced (as a safeguard against purity sensor drift). In step 302, the pressure can, however, be increased by an increased O$_2$ factor, if the purity consistently runs below the target purity, e.g. 88%, for a long period of time. This is done, for example, to allow for long term degradation of the sieve due to water loading. As shown in step 306, a proportional integral control loop is used to maintain this target pressure in the product tank on a time averaged basis. The compressor motor is sped up (slowly through a low pass filter, as indicated in step 308) to create a higher product tank pressure, and slowed if the pressure is higher than target. As illustrated in step 310, PWM is used to control the speed, which the motor sees as changing voltage.

Because there is a low pass filter on the PWM, the power provided to the motor stays relatively fixed through the sieve bed cycle. Therefore, as the bed pressure rises through the cycle, the compressor is allowed to slow down due to the increased pressure load (torque). This, in turn, leads to less fluctuation in the required power than would be seen if a fixed speed (rpm) were targeted. The higher power would be the result of working harder to maintain a fixed rpm under increasing pressure load. The resulting lower power fluctuation means lower peak battery current, which leads to increased battery life (duration).

The PWM, which is calculated to maintain product tank pressure, is modified by changes to the system voltage. Thus, if the PWM is set perfectly with batteries that are at ¼ charge (~13 volts), and the AC external power source (18V) is plugged in, the motor speed remains the same with only a slight jump, instead of a large increase and subsequent slow decrease.

The present invention contemplates, but does not require, using the oxygen purity monitored by oxygen sensor 118 to control the speed of the motor. Changes in the oxygen purity may be affected by the condition of the sieve material within the sieve beds 12, the temperature and/or the humidity of the ambient air being drawn into the apparatus 10 to charge the sieve beds, and the like. Controller 22 may have a set target oxygen purity stored in memory, e.g., between about 85-93%, such as 88%, and may monitor the purity detected by oxygen sensor 118. If the oxygen purity decreases below the target oxygen purity, controller 22 may increase the target reservoir pressure to compensate and increase the oxygen purity. This may trigger the controller increasing PWM based upon the control loop used by the controller to maintain the new target reservoir pressure.

Thus, controller 22 may modify PWM, i.e., the speed of motor 40 of the compressor 14, to maintain the reservoir near its target pressure, which the controller may modify based upon the parameters monitored by the controller.

The maximum oxygen production rate is dependent upon the speed of compressor 14, which, in turn, is dependent upon the input voltage from batteries 148. To operate effectively, it is desirable for apparatus 10 to operate at or close to the target parameters, even as the batteries begin to deplete their charges. For a 4S4P Li-Ion battery, the voltage at the end of the battery's charge may be about eleven Volts (11 V). When this battery is fresh (or when apparatus 10 is connected to an external power source), by comparison, the voltage may be as much as 16.8 Volts. To prevent excess oxygen generation when batteries 148 are fully charged, it may be desirable to impose a maximum speed for compressor 14, e.g., not more than about 2,500 rpm. Alternatively, controller 22 may allow this maximum speed to be occasionally exceeding within a predetermined margin of safety, in order to reduce the risk of damage to compressor 14.

By way of example, for an apparatus delivering up to sixty milliliters (60 ml) per breath, an exemplary flow rate of about eight liters per minute (8 lpm, or about 133 ml/s.) may be used. The equivalent volume of 88% oxygen gas is about seventy milliliters (70 ml), and the pulse duration would be about 0.53 second. If the apparatus is capable of generating up to about 1200 ml/min, the maximum breathing rate at maximum dose setting would be about seventeen (17) breaths per minute. Assuming an I:E ratio of 1:2 and that the first fifty percent (50%) of each of the user's breaths are functional (and not filling dead-space), the minimum available time would be 0.60 second. At higher breathing rates, the maximum pulse volume (and pulse duration) would be lower because of the maximum production rate.

Because apparatus 10 may operate at relatively low pressures, e.g., between about five and twelve pounds per square inch (5-12 psi), the flow through any controlling passage within the apparatus will not be sonic. Consequently, if the back pressure of apparatus 10 varies, e.g., due to the cannula or tubing connected by the user, it may cause changes in the flow rate of oxygen delivered to the user. At eight liters per minute (8 lpm), the resistance of cannula may be between about 0.7 and two pounds per square inch (0.7-2 psi), e.g., for a Hudson cannula or a TTO catheter was approximately. This increased back pressure may reduce the flow rate of oxygen delivered to the user by as much as twenty five percent (25%).

To allow for variance in both reservoir pressure and downstream pressure (pressure from reservoir 18 to the user via the cannula), the following algorithm may be employed. The valve "on time" may be adjusted to maintain a fixed pulse volume (as set by the selected dose setting). The reservoir pressure may be measured during the time that oxygen delivery valve 166 is off, and the pressure across oxygen delivery valve 116 may be measured, e.g., using pressure sensor 120, while the oxygen delivery valve 116 is open.

Valve On Time or the pulse duration (Time Delivery in Table 2) may be set as a factor of dose setting adjusted by oxygen purity to get actual volume, reservoir pressure, and pressure drop across oxygen delivery valve 116. The equations that may be used for these calculations are shown in Table 2, which includes exemplary control parameters that may be used to operate apparatus 10.

TABLE 2

| Parameter | Type | Units | Range | Start Value | Definition |
|---|---|---|---|---|---|
| Time Pressurize | Calc. | sec | 4-12 | 6 | Pressure Product PsiF × Time Pressurize Gain + Time Pressurize Offset. This parameter may be calculated from Target pressure instead of measured. Shorter time creates lower pressure. |
| Time Pressurize Gain | Set | sec/psi | 0-(−.6) | −0.3 | |

TABLE 2-continued

| Parameter | Type | Units | Range | Start Value | Definition |
|---|---|---|---|---|---|
| Time Pressurize Offset | Set | sec | 0-20 | 9 | |
| Time Overlap | Set | sec | 0-2 | 0.2 | |
| Reservoir Pressure | Meas | PSI | 0-15 | 8 | Measured from Product Trans. from sensor 114 in reservoir with oxygen delivery valve 116 closed. |
| Pressure Product | Calc | PSI | 0-15 | 8 | Controller 22 may include a low pass filter with a time constant about thirty seconds (30 sec) to filter out breath and cycle variations. |
| Pressure Valve Psi | Meas | PSI | 0-15 | | Measured from Product Trans. using sensor 114 with oxygen delivery valve 116 open. The measurement may be delayed after oxygen delivery valve 116 is opened, e.g., at least about 100 ms to avoid artifact. |
| Pressure Valve PsiF | Calc | PSI | 0-15 | 7 | Controller 22 may include a low pass filter, e.g., with a time constant of about 100 ms, to filter out noise. |
| $O_2$ Percent | Meas | | 21-96 | | Measured from oxygen sensor 118. |
| $O_2$ Percent F | Calc | | 21-96 | 80 | The controller may include a low pass filter, e.g., with a time constant of about 30 s., to eliminate cycle variations. |
| $O_2$ Percent Target | Set | | 75-92 | | Control Algorithm Target $O_2$ Percent (resolution .01) |
| Pulse Vol ml | Set | ml | 10-60 | | Set by patient, equivalent dose of 100% $O_2$ gas |
| Pulse Vol Act ml | Calc | ml | 11-80 | | Actual Delivered Volume = 79/ ($O_2$ PercentTarget − 21) × PulseVolml could use $O_2$Percent instead of Target; but may be less stable, as volume will go up as % goes down, which in turn could cause % to decrease further |
| Time Resp Sec | Meas | sec | 1-5 | | Measured time between last two breaths |
| Time Resp Sec F | Calc | sec | 1.5-5 | 3 | Low pass filtered 5-10 breaths |
| Production Vol ml | Calc | ml/min | 0-1500 | | Pulse Vol. ml × 60/Time Resp. Sec F |
| Pressure Product Target Psi | Calc | PSI | 3-12 | | (Pressure Product Target Gain × Production Vol. ml + Pressure Product Target Offset) × $O_2$ Factor |
| Pressure Product Target Gain | Set | PSI/mL/min | 0-.03 | 0.01 | |
| Pressure Product Target Offset | Set | PSI | 0-12 | 3 | |
| $O_2$ Factor | Calc | none | .5-1.5 | 1 | 02 Factor (old value) × ($O_2$ Percent Target − $O_2$ Percent F) × $O_2$ Factor Gain |
| $O_2$ Factor Gain | Set | none | | | Depends on how often updated, but should change gradually, over 1-20 minutes |
| Motor Pwm | Calc | | min-100 | | Motor Pwm (old value) × (Pressure Product Psi F − Pressure Product Target Psi) × Motor Pwm Gain. Closed loop control to obtain PressureProductTargetPSI |
| Motor Pwm Min | Set | | 0-50 | 50 | Minimum and startup PWM value, to avoid non-rotating pump |

TABLE 2-continued

| Parameter | Type | Units | Range | Start Value | Definition |
|---|---|---|---|---|---|
| Motor Pwm Gain | Set | | | | Sets how rapid motor control changes are - depends on how often updated - control may change somewhat rapidly, because product pressure is already filtered. |
| Time Delivery Msec | Calc | Msec | 100-700 | | (Pulse Vol Act ml × Pressure Valve Psi F"0.5 × Time Delivery Gain)/((Pressure Product Psi + 14.2). Time to hold the delivery valve open- needs more empirical validation |
| Time Delivery Gain | Set | none | 50-200 | 100 | |

In an alternative embodiment, a valve (not shown) is provided that acts similar to a pressure regulator. Instead of controlling the downstream gauge pressure, it controls a pressure drop across an orifice placed inline downstream with the delivery valve. In this way, regardless of the of downstream pressure, the same flow rate may be delivered, and the resulting volume at a selected pulse duration may be substantially constant.

When a user decides to turn off or shut down apparatus 10, e.g., by depressing an on/off switch or depressing a "button" on a touch screen, e.g., on user interface 144, it may desirable for the apparatus to complete a procedure automatically to protect the apparatus. For example, if pressurized air remains in sieve beds 12 after shutdown, water in the air may condense or otherwise be absorbed by the sieve material, which may damage the sieve material. It may also be desirable to substantially isolate sieve beds 12 from atmospheric conditions, e.g., to prevent the sieve beds from "breathing" when apparatus 10 encounters changing barometric pressure and/or temperature. Any such breathing may introduce air into or evacuate air out of the sieve beds, which may introduce moisture into the sieve material.

When apparatus 10 is being turned off, oxygen delivery valve 116 may be closed to discontinue delivery of oxygen from reservoir 18. Supply air control valves $20_s$ may be automatically closed (either actively or as the default when electrical power is turned off), e.g., while exhaust air control valves $20_s$ are opened. After a first predetermined time, e.g., between about one hundred and three hundred milliseconds (100-300 ms), compressor 14 may be turned off. Leaving compressor 14 operating momentarily after closing supply air control valves $20_s$ may leave residual pressure within the manifold 16, which may enhance holding the control valves $20_s$ closed for an extended period of time. This pressure may leak slowly over time.

After a second predetermined time, e.g., between about nine and twelve seconds (9-12 sec), allowing any pressurized air to be exhausted from sieve beds 12, the exhaust air control valves $20_e$ may be closed (either actively or as the default when electrical power is turned off).

H. Carrying Bag

The overall external appearance of apparatus 10 is best shown in FIGS. 1A and 1B. The bottom exterior surface is defined by air manifold 16, the opposing top exterior surface is defined by oxygen manifold 102, the exterior surface of one end portion is defined by side panels 59, 159, the exterior surface of the opposing other end portion is defined by sieve beds 12 and reservoir 18, the exterior surface of one side portion is defined by a panel 200, and the exterior surface of the opposing other side portion is defined by a panel 202. In an exemplary embodiment, panels 200 and 202 are relatively thin sheets of material, such as plastic or metal. Their primary purpose is to enclose the internal volume of the apparatus. However, the can all provide structure support for the device. The present invention also contemplates that these panels can be omitted entirely.

It can be appreciated that the external appearance of the apparatus as presented by the above-noted components is not aesthetically pleasing, provides little protection for the apparatus, and does little to help reduce the sound generated by the apparatus. To accomplish these, and other functions, the present invention contemplates providing a carrying bag 210 to house apparatus 10. The carry bag eliminates the need for, and weight of, an external plastic enclosure typical of conventional portable oxygen concentrators.

Figure 21:
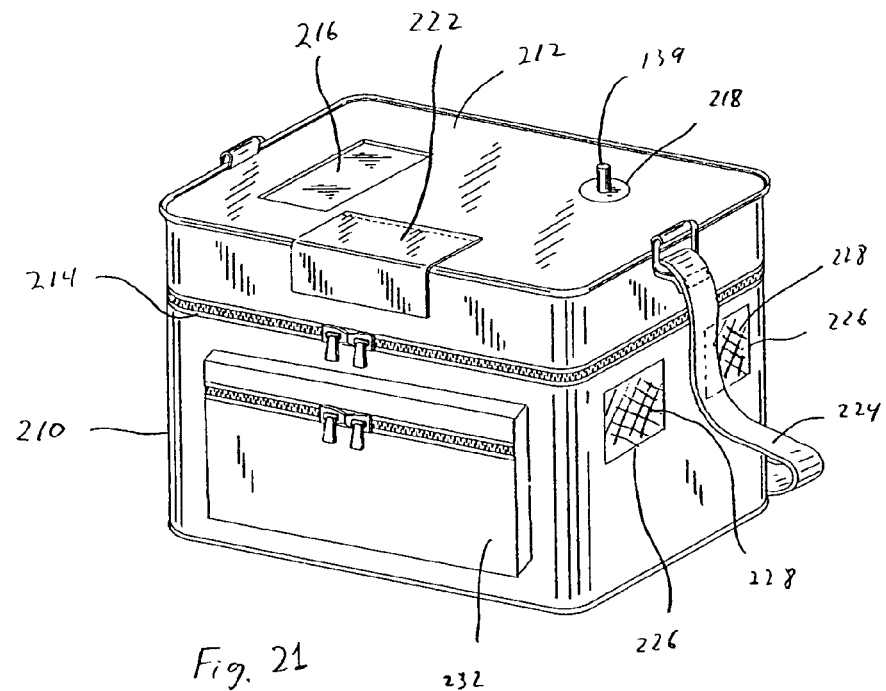
FIGS. 21-23 are a top perspective views of the portable oxygen concentrator shown housed in a carrying bag showing various panels either open or closed.
Figure 22:
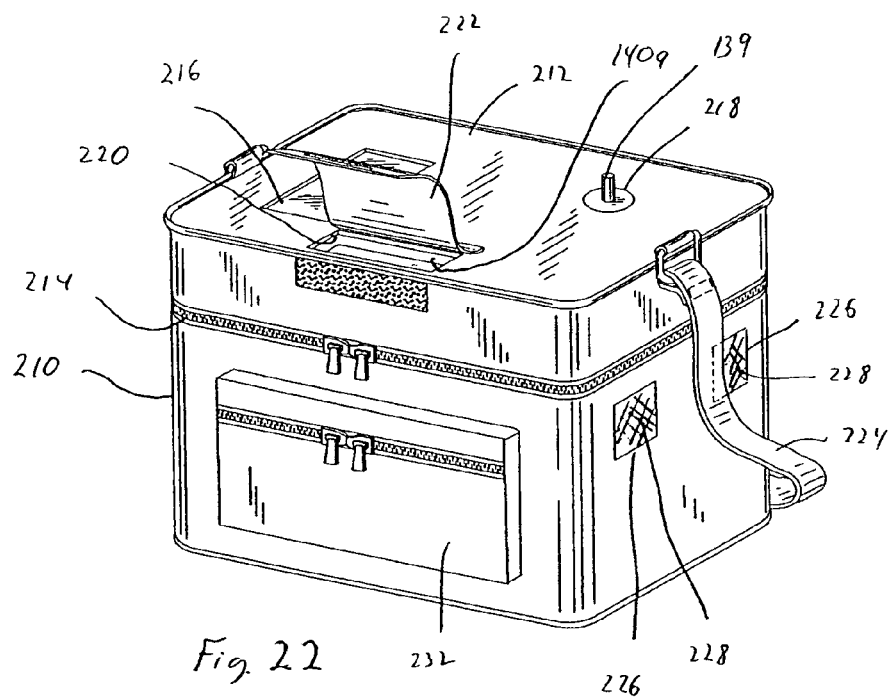
Figure 23:
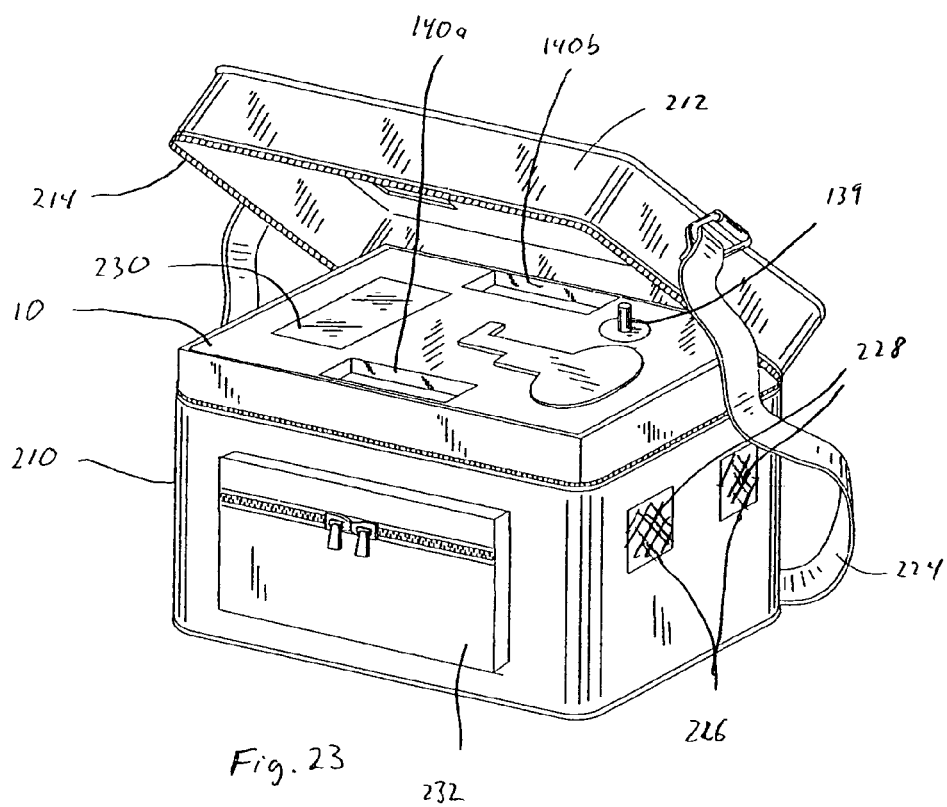

An example of a carrying bag 210 suitable for this purpose is shown in FIGS. 21-23. Bag 210 is made from a light-weight material, such as polyester with a PVC coating, that has a shape generally corresponding to the shape of apparatus 10 and completely encapsulates the apparatus. The material, or combination of materials, is selected so as to be durable, light weight, stain resistant, water resistant, or any combination thereof.

The present invention contemplates that apparatus 10 and bag 210 are secured together so that the apparatus be easily removed from the back. For example, screws, bolts, or other fasteners can be used to join the bag to the oxygen conserver apparatus. This allows a technician, for example, to disassemble the bag from the apparatus, but will make it difficult for a user to remove the apparatus from the bag, as well as prevent the apparatus from accidentally falling or slipping out of the bag. In this way, the bag is an integral part of the entire oxygen conserver apparatus.

Bag 210 has a generally rectangular shape to match the shape of apparatus 10. However, there is no requirement that the shape of the bag match that of the concentrator it is housing. Bag 210 includes a top panel or flap 212 that is at least partially separable from the remainder of the bag to allow access to the interior of the bag. In the illustrated embodiment, a zipper 214 is provided around a portion of the perimeter of the bag to allow top panel 212 to be opened, as shown in FIG. 23, or closed, as shown FIGS. 21 and 22. It is through this access that the apparatus is placed into and removed from the bag. The present invention contemplates providing a lock on zipper 214 so that the top panel cannot be opened without authorization.

Top panel 212 includes a transparent panel 216 that overlies touch screen display 230 when the top panel is closed. This transparent panel is sufficiently flexible so that the user can operate the touch screen user interface through this panel. Transparent panel 216 is also made from a water resistant, durable material so that it can effectively protect the touch screen without impeding its use. Top panel also includes a cannula barb access port 218 so that cannula barb 139 extends through the bag wall. In an exemplary embodiment, a flexible material, such as neoprene, is provided around cannula barb access port 218 to prevent water ingress and allow flexibility in the position of the cannula barb through the wall of the bag.

To access battery opening 140a and/or 140b a battery slot 220 is also provided in top panel 212. A battery slot flap 222 covers battery slot 220 and is held in the closed position via a fastening mechanism, such as a hook and loop fastener, zipper, snap, or the like. Moving battery slot flap 222 provides access to battery slot 220 so that a battery can be provided or removed from the battery slot. Although only one battery slot 220 and battery slot flap 222 is shown in bag 200, it is to be understood, that the second battery opening can also be accessed and covered by a similar system. If, however, only one battery slot is provided, the second battery opening is accessed by opening top panel 212, as shown in FIG. 23.

The end wall of bag 210 includes one or more inlet cutouts 226 that overlie inlet opening 160a, 160b when apparatus 10 is disposed in the bag. A mesh or other screen 228 is provided in inlet cutouts 226 to prevent large materials from entering inlet opening 160a, 160b. In an exemplary embodiment, a filter housing pocket is also provided over inlet cutouts 226 either on the inside, the outside of the bag, or both for holding a disposable filter over inlet opening 160a, 160b. In a further embodiment, the bag is configured such that the path the flow of air must follow in order to reach inlet opening 160a, 160b is a tortuous path and is open in a downward direction to prevent water egress into the interior of the bag.

The present invention further contemplates that bag 200 includes a carrying handle or strap 224 that is affixed to or detachable from the bag. The bag also includes pockets 232. The number, size, location, and configuration of the pockets, handles, or straps can be varied in any manner to suit the needs of the user, including providing internal pockets or recesses.

Bumpers or other spacers can be provided on one or more of the interior surfaces of the wall of the bag. Optionally, bag 200 may include padding or other sound absorption materials to help minimized the sound outside the bag. In other words, the bag itself can be made from or packed with a sound attenuating material or can include sound attenuating materials at strategic locations to keep sound levels to a minimum. In addition, foam pads or other supporting/shock absorbing material can be provided at the bottom of the interior of the bag or at other locations in the bag to support apparatus 10. In an exemplary embodiment, relatively high density foam pads are provided at each lower corner of the bag for protecting apparatus 10 and lower density foam material is used elsewhere to minimize weight. In addition, the bottom of the bag can be provided with a high strength, water impervious material, such as rubber, to protect the bottom of the bag, which is expected to experience the greatest wear and tear.

I. Touch Screen User Interface

Figure 24:
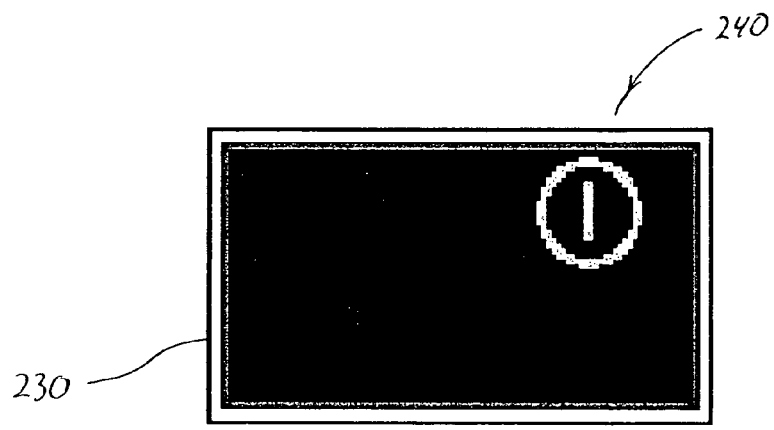
FIGS. 24-32 illustrate a touch screen user interface used in the apparatus of the present invention.
Figure 54:
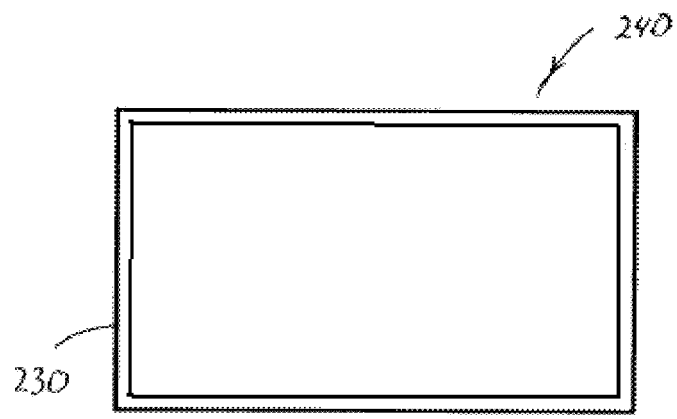
FIG. 54-56 illustrates a touch screen user interface used in the apparatus of the present invention.
Figure 55:
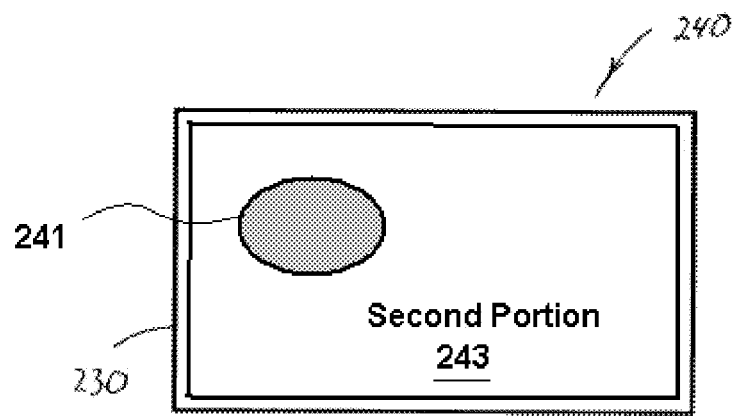
Figure 56:
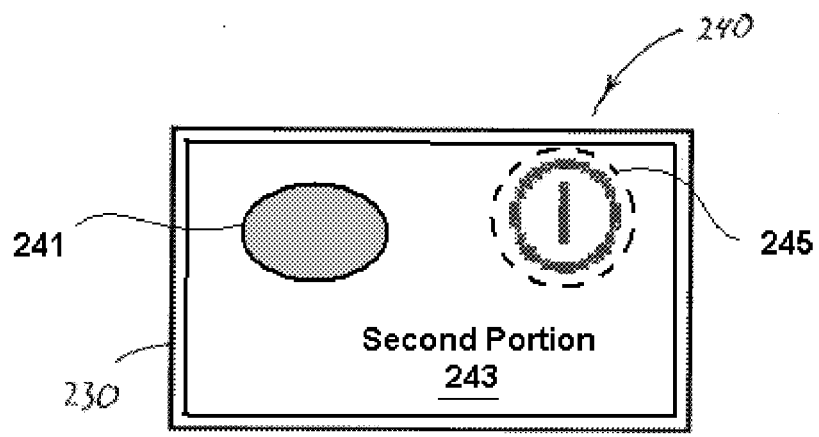

FIGS. 24-32 and 46-56 illustrate examples of displays, i.e., visual information, that is capable of being provided on user interface 144 during use of apparatus 10. More specifically, these figures illustrate various examples of the information that may provided on touch screen 230. When the device is off, the display is blank as shown in FIG. 54. When touch screen 230 is touched once, an on/off icon 240 is presented, as shown in FIG. 24. Activating the apparatus requires touching on/off icon 240 located in an area 245 (see FIGS. 24 and 55), causing the system to advance to an active state. Touching other locations of the touch screen, i.e., areas other than area 245 (see FIG. 56), will not start the apparatus. It can thus be appreciated that activating the device requires two touches on the touch screen, with the second touch being at a specific location (e.g., area 245) on the touch screen. This "double touch" feature of the present invention prevents unwanted or inadvertent activation of the apparatus.

The present invention further contemplates that "on/off" icon 240 may be displayed at a different location (e.g., area 245) than the first detected contact location 241. See FIG. 55. The controller may be configured such that, if the same location on the touch screen as the first detected contact location is contacted, the controller may ignore such a contact. In other words, the system establishes a second area 243 that does not overlap the first detected contact location 241. The user must contact the second area 243 in order to initiate a command. This may reduce the risk of false positives, e.g., due to the user or objects accidentally contacting a single location on the touch screen, which may increase safety in operation.

The controller may include a timer such that the controller waits a preset time, e.g., several seconds, in anticipation of the "on/off" icon being contacted. If the portion of the touch screen displaying the "on/off" icon is not contacted within the preset time, the controller may reset the concentrator, e.g., returning the concentrator to the sleep state.

Once activated, the system may display predefined information, such as a corporate logo, advertisements, user instructions, diagnostic information, error information, usage information, and the like. The present invention contemplates that the controller is configured for displaying information on the touch screen related to the status and/or operating conditions of the concentrator. The information may be displayed as one or more desired icons, e.g., alphanumeric symbols in English or other languages, as symbols, or as graphs or scales (e.g., a bar graph).

In one embodiment, the controller may detect when a first portion 241 of the touch screen is contacted by a user, and thereafter may control the touch screen to display one or more icons on a second portion 243 of the touch screen. See FIG. 56. The controller may then detect when the second portion 243 of the touch screen is contacted by a user, whereupon the controller may control operation of the concentrator and/or display additional information to the user The present invention also contemplates that concentrator 10 is maintained in a "sleep" mode in which touch screen 230 may be blank. For example, the concentrator may have been previously shut off by the user or may have shut down due to inactivity or based upon other parameters. When "asleep", touch screen 230 and controller 22 may remain active, i.e., waiting to detect any contact of the touch screen.

Figure 25:

FIG. 25 illustrates information that may be provided on the touch screen at start-up. As shown in FIG. 25, touch screen 230 includes fields 242 that indicate the version of software currently being run by the apparatus, a field 246 that indicates the number of hours the apparatus has been used, and a field 248 that indicates any error codes, i.e., errors that may have been detected during a diagnostic process, which could have been conducted earlier and/or during startup of the device.

Figure 26:
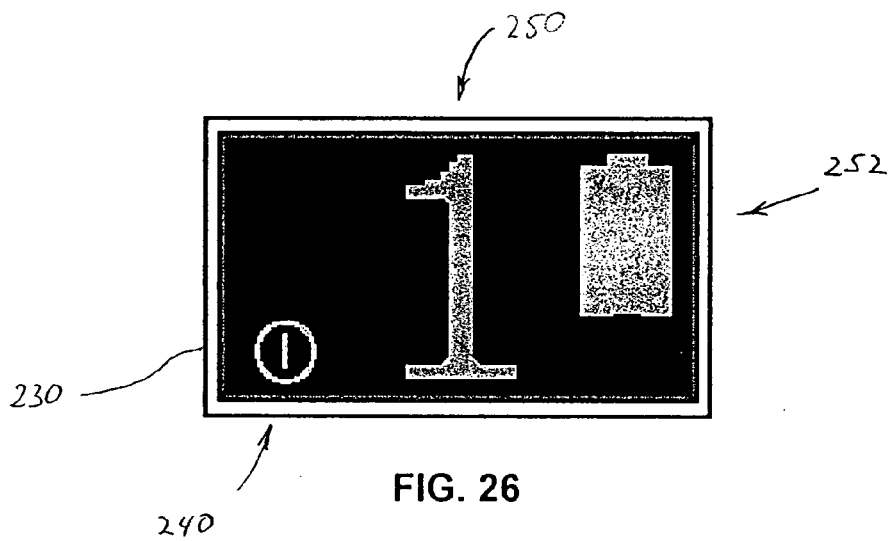

FIG. 26 illustrates the information provided on a typical touch screen 230 after apparatus 10 is turned on. As shown in this figure, touch screen 230 includes on/off icon 240, a pulse dose or flow setting indication 250, which is the numeral "1" in the illustrated embodiment, and a battery icon 252. It can be appreciated that the size of flow setting indication 250 is relatively large, i.e., large enough to occupy 20-80% of the entire touch screen. This enables the user to easily visually discern the flow setting. In an exemplary embodiment of the present invention, the actual height of the flow setting icon is at least one half inch and the actual width is at least one quarter inch. In an exemplary embodiment, the height is at least 1.25 inch and the width of each digit is one half inch or greater. In addition, in an exemplary embodiment, battery icon 252 is at least o½ inch wide and at least ¾ inch tall.

In the illustrated exemplary embodiment, battery icon 252 is a solid battery-shaped image that indicates that the primary battery is inserted into battery opening 140*a* and the battery is fully charged. It is to be understood that if a secondary battery is inserted into secondary battery opening 140*b*, a second battery icon is displayed on the other side of touch screen 230 (see, e.g., FIG. 28). This enables the user to quickly and easily determine what batteries are inserted into the battery openings and the amount of life left in each battery. Of course, battery icon 252 can have other shapes and need not be solid. For example, the image may be an outline of a battery.

Figure 27:
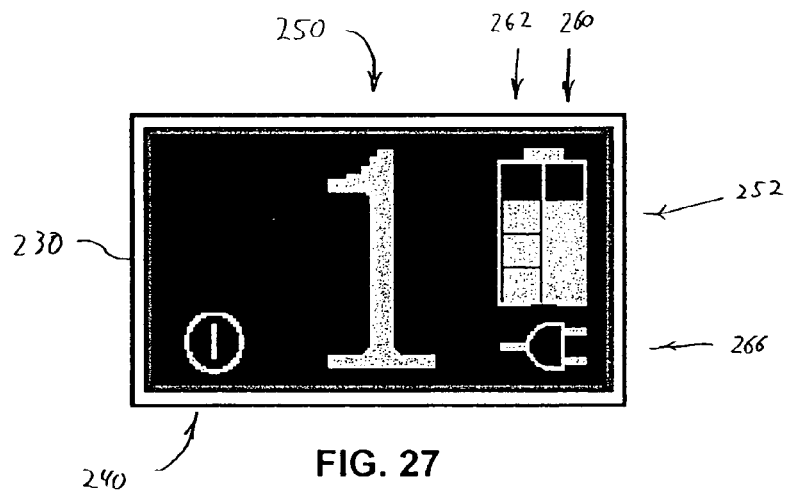

FIG. 27 illustrates battery icon 252 in a format that shows the amount of energy remaining in (or removed from) the battery. In this embodiment, the battery icon has a right field 260 and a left field 262. These fields are used to provide more detailed information about the battery. For example, in this embodiment, right field 260 indicates the amount of charge (e.g., 75% in the illustrated embodiment), and left field 262 indicates whether the battery is charging. In the illustrated embodiment, vertical bar in left field 262 is scrolled or animated in some fashion to indicate that battery charging is taking place. An AC power icon 266 is also shown on touch screen 230 to show that the apparatus is connected to an AC power source.

Figure 28:
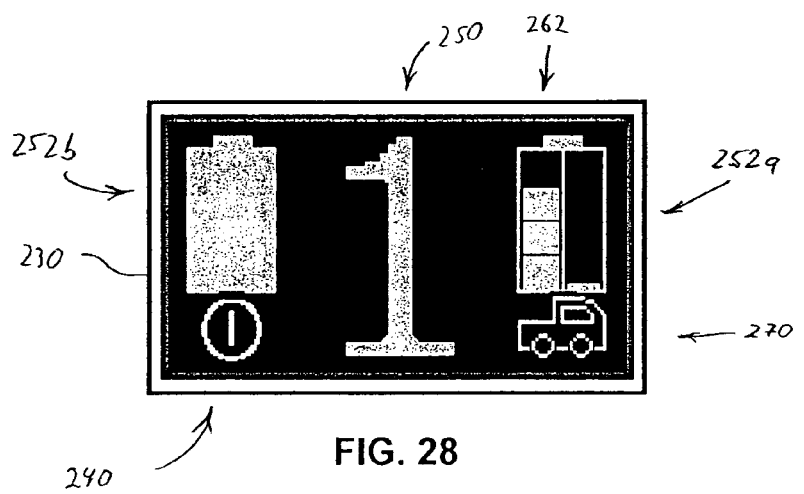

FIG. 28 illustrates a typical display that shows that two batteries are inserted into the battery openings as indicated by batter icons 252*a* and 252*b*. It can be appreciated from this display that the secondary battery in battery opening 140*b* is fully charged (left battery icon 252*b*) and the primary battery in battery opening 140*a* is nearly empty (right battery icon 252*a*) and is charging. Touch screen 230 also includes a DC power icon 270 that indicates whether the apparatus is connected to a DC power supply, such as that available via a car adapter.

Figure 29:
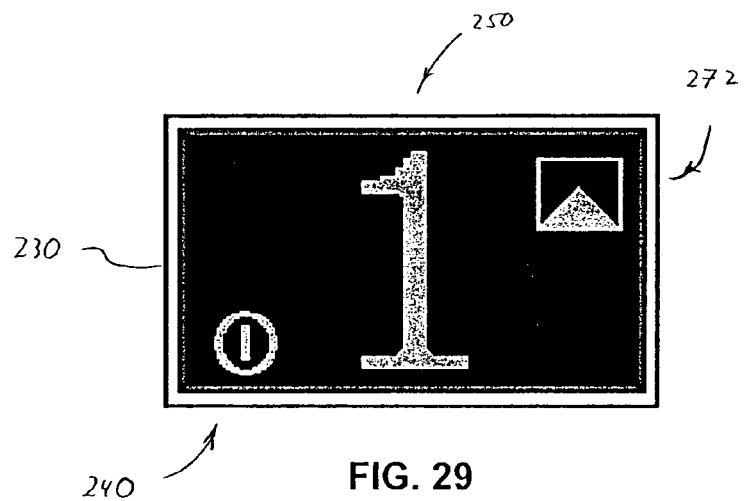
Figure 30:
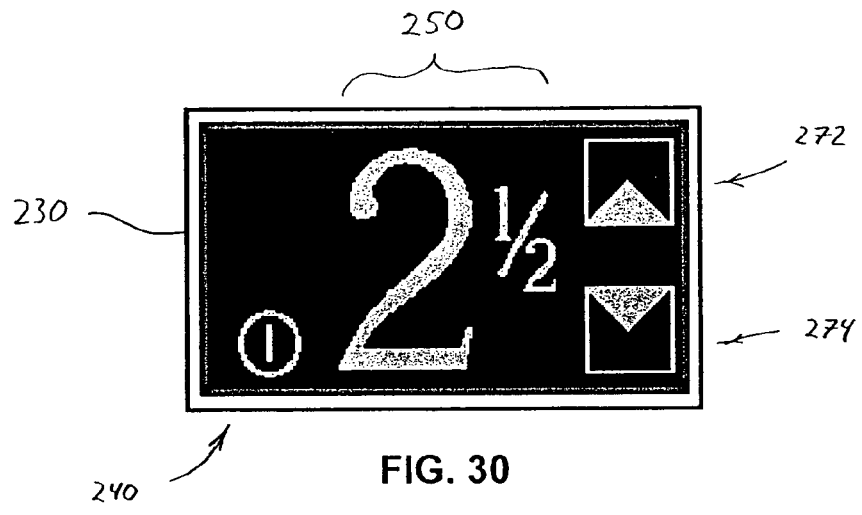

To change the flow setting, the user must first press flow setting indication 250. After a short period of time, e.g., 2-6 seconds, flow setting change icons 272 and/or 274 are displayed, examples of which are shown in FIGS. 29 and 30. In this embodiments, the flow setting change icons 272, 274 are in the form of up or down arrows. Note that only one flow setting change icon is shown in FIG. 29, because "1" is the lowest flow setting so that the flow setting can only be increased, not decreased. Actuating the flow setting change icon will cause the apparatus to change the output flow. The new flow setting is displayed. The flow setting change icons will remain on the screen for a short period of time, e.g., 2-6 seconds, or until the flow setting indication 250 is pressed again.

Figure 31:
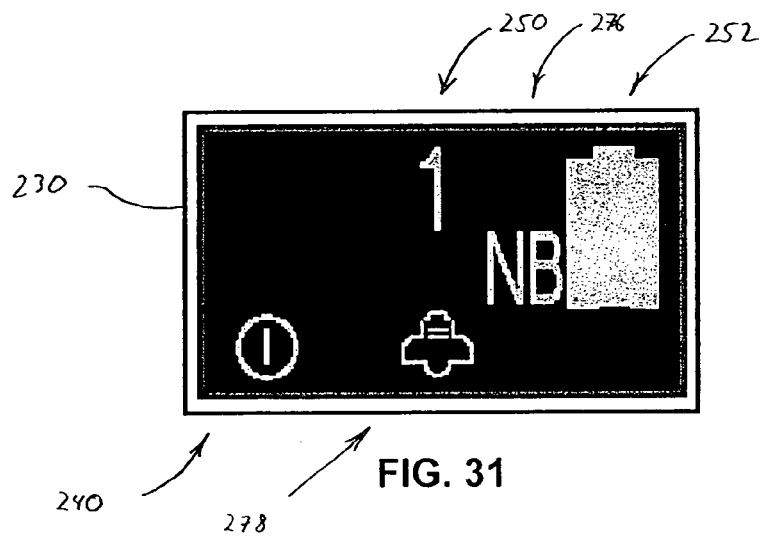
Figure 32:
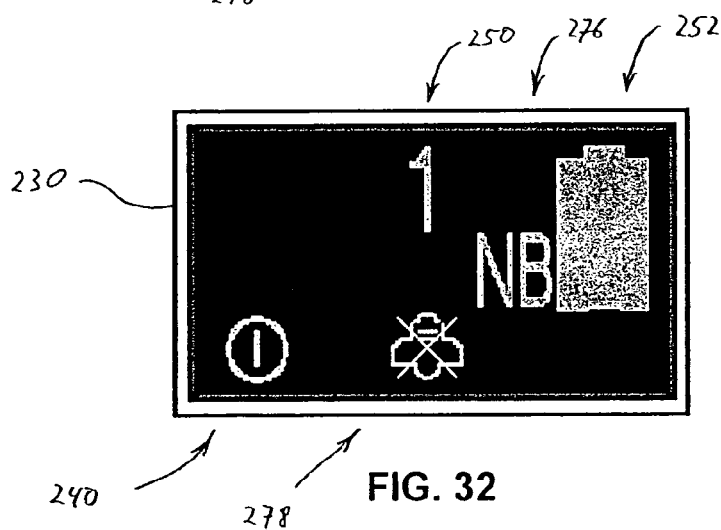

As noted above, apparatus 10 includes the ability to sound alarms or other warnings if a monitored variable exceeds a threshold. FIGS. 31 and 32 illustrate and example of the appearance of touch screen 230 when an alarm condition is detected. Upon detecting an alarm occurs, an alarm icon 276 indicating the nature of the alarm is displayed on the touch screen. Note that the size of flow setting indication 250 has been reduced to better show the alarm icon.

In the embodiment illustrated in FIGS. 31 and 32, the alarm condition is the failure to detect a user's breath. This can occur, for example, if the user ceases using the device. In this case, an "NB" icon indicating that the controller has detected that the user has not inhaled for a predetermined time period is displayed on the touch screen. Such detections may be detected using a pressure sensor in the outlet path of the concentrator.

An audio alarm icon 278 may also be displayed if the alarm condition is such that it causes an audible warning to be provided, in which case and the controller may activate a speaker, other audio alarm of the concentrator, and/or send a message (e.g., via an internal wireless transmitter). If the user contacts the alarm icon, the audio alarm may be turned off, and the audio alarm replaced with an audio off alarm 278, as shown in FIG. 32. Audible alarm icon 278 is used to turn the audible alarm on an off by simply touching that icon.

If the user wishes to shut the concentrator off, the user may contact "on/off" icon 240, e.g., shown in the corner of FIG. 27. Thereafter, the controller will display the "on-off" icon again, but on a different portion of the touch screen. The user may then contact the "on/off" icon on the new portion, confirming the user's desire to shut the concentrator off. The controller may then complete any operations necessary to return the concentrator to the sleep state.

FIG. 33 is a chart illustrating the alarm icons that are provided on touch screen 230. The following is a brief discussion of each alarm condition listed in this chart.

NO BREATH ALARM—This alarm occurs when a breath is not detected for a period of 30 seconds or more. This alarm will become silent as soon as a breath is detected. If no breath is detected after approximately 5 minutes, the unit will shut down to conserve power.

OXYGEN CONCENTRATION ALARM—This alarm occurs when apparatus 10 is not delivering the concentration of oxygen that is specified.

HIGH BREATH RATE ALARM—This alarm is a notification that the user's breath rate is starting to exceed the capacity of the apparatus. The alarm will reset itself when breath rate is reduced.

TECHNICAL FAULT/GENERAL MALFUNCTION ALARM—The device shuts down when this alarm occurs. This alarm occurs when the battery runs out or the device has a general malfunction and the unit is no longer operating properly.

AUDIBLE ALARM ICON—This icon appears when an audible alarm occurs. Press this icon to silence the audible alarm.

ALARM SILENCE ICON—This icon appears when the user presses the audible alarm icon in order to silence the audible alarm.

BATTERY LOW ALARM—Battery icon(s) flashes when approximately 17 minutes of battery life remain.

BATTERY DEPLETED ALARM—Indicates approximately 2 minutes of battery life remain.

BREATH RATE ALARM—Indicates that the breathing rate of the user exceeds the capacity of the unit.

TECHNICAL FAULT ALARM—The alarm occurs when the battery runs out or the device has a general malfunction and the unit is no longer operating properly. In an exemplary embodiment, the device will shut down when this alarm condition occurs.

DC POWER CONNECTION SYMBOL—Indicates that the unit is coupled to a DC power supply.

ATTENTION ALARM—This symbol appears when corrective action is required.

PULSE SYMBOL—The dot next to the on/off icon appear when the unit delivers a pulse, i.e., whenever the user takes a breath.

Optionally, turning to FIGS. 46-53, the concentrator may be configured for sending one or more communications between the concentrator and an external device. For example, the concentrator may be connected to a telephone network, e.g., by a cable, modem, and the like, or the concentrator may include a wireless transmitter and/or receiver, e.g., similar to a cellular phone, such that the concentrator may communicate via a wireless network. The present invention contemplates that any type of communication link, wireless or hardwired, can be used to communicate the concentrator with the external device. Also, any type of external device may be used to communicate with the concentrator. For example, the external device can be a database, a computer, a dedicated communication device, a router, or any other device capable of communicating with the concentrator.

Figure 47:
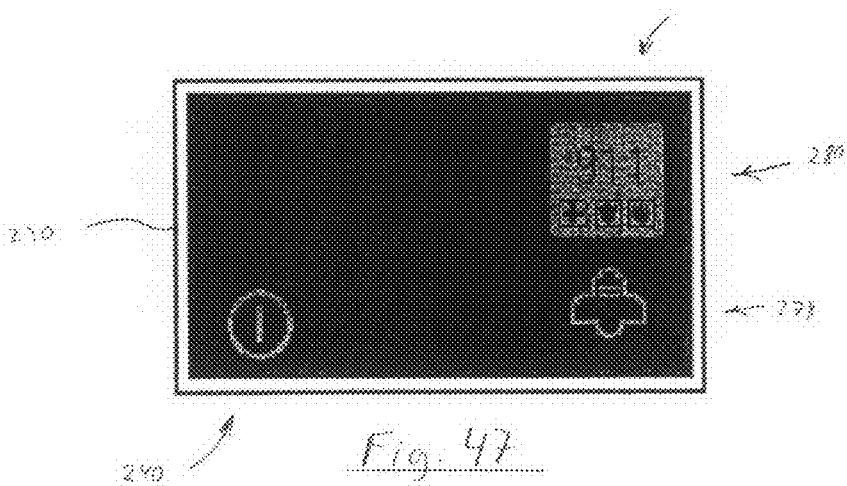

As shown in FIG. 47, the controller may display an emergency icon 280. If the emergency icon is contacted, the controller may automatically send an emergency message, e.g., requesting assistance from paramedics, police, and the like. In addition or alternatively, as shown in FIG. 49, the controller may display an image 281 similar to a telephone or keypad, allowing the user to "dial" a telephone number by touching the appropriate numbers on touch screen 230, and pressing a "dial" icon 282. Other versions of a possible warns icons that may be displayed on the touch screen are shown in FIG. 51. Such icons include an exclamation point 275, a "911" box 277, and an ambulance image 279.

The concentrator may automatically send a message or the user may send a message, e.g., by pressing the numbers on the touch screen to create a text message, similar to mobile telephones. Optionally, the controller may display information related to such wireless communication, e.g., signal strength, and the like on the touch screen, if desired.

Some of the display modes shown in FIGS. 46-53 may be entered through a programmed sequence of steps. For example, FIG. 52 displays an optional mode that a technician may access, e.g., to service or repair concentrator 10. The technician may contact a portion of the touch screen, for example, on the "engineering" or startup screen of FIG. 25. The active portion of the touch screen may be hidden, i.e., may not be identified, but may be known by the technician, e.g., pressing one or more corners of the touch screen in a preset sequence. Thus, some of the modes may not be used during normal operation of the device, or may be set mechanically, e.g., via a switch (not shown) in concentrator 10 that would allow some of the settings and/or icons to be displayed along with the default screen, e.g., FIG. 27.

Optionally, the user may change the display, e.g., from a setting number to an actual flow rate value 283, e.g., as shown in FIG. 50. In the embodiment, flow setting change icons 284 and 285 are provided, each of which indicates a numeric value to which the flow rate can be changed, along with the up and down arrows. The default (setting number or actual flow values) may be changed from the engineering screen or may be changed by the end user by following specific commands, e.g., pressing the setting for a predetermined time and/or sequence, and the like.

In other embodiments, concentrator 10 may include a pulse oximetry board and a sensor, which may be placed on the user's finger, as is known to those of ordinary skill. The sensor may be hard-wired to the board or may communicate wirelessly with the board. The controller may monitor the sensor and cause the touch screen to display pulse and/or oximetry data for the user. Of course, other sensors or monitors can be provided that communicate with the concentrator and whose output can be displayed on touch screen 230.

Figure 46:
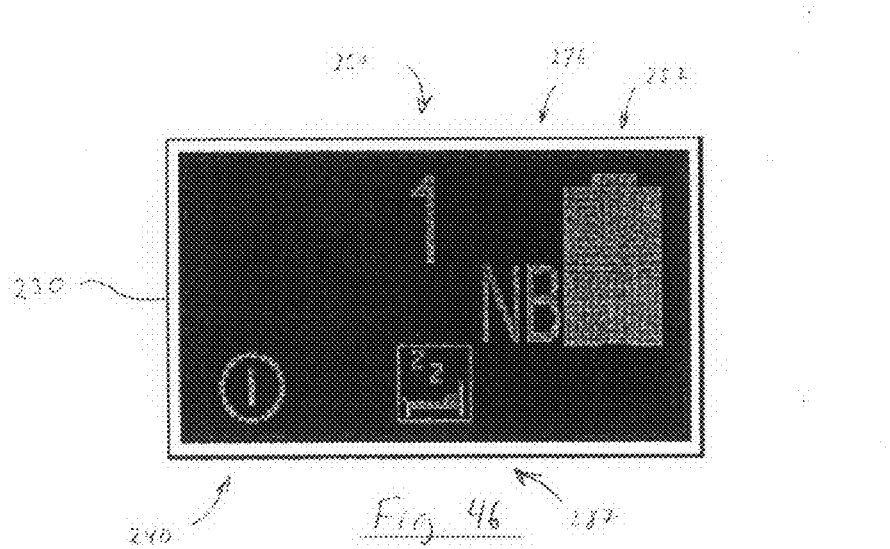
Figure 48:
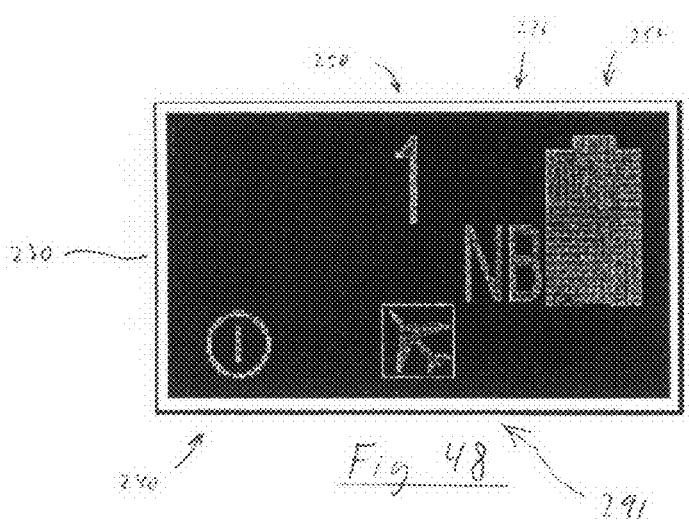
Figure 52:
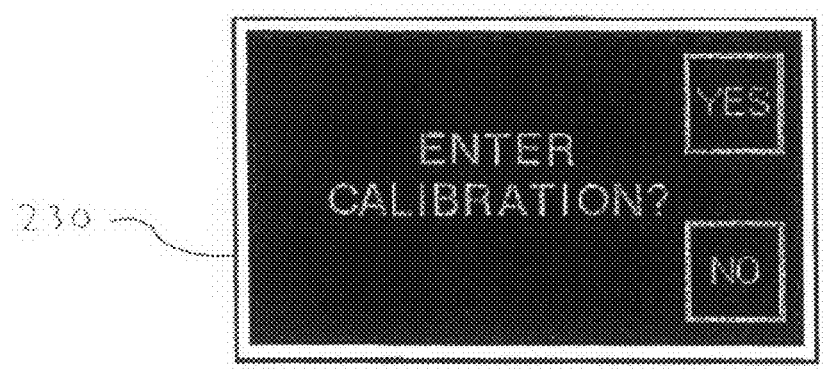

FIG. 46 shows touch screen 230 with a sleep mode icon 287 displayed thereon. Sleep mode icon 287 shows a person sleeping in a bed and indicates that the unit is currently operating in a sleep mode. The sleep mode can correspond, for example, to a particular operating mode for the portable oxygen concentrator. In one exemplary embodiment, the sleep mode is a mode that is used to provide a given type of gas delivery when the patient is sleeping that is different from that delivered when the patient is awake. For example, a continuous flow of gas—rather than pulses doses—can be delivered during the sleep mode. The present invention contemplates that other modes can be provided, and that icons representing each of the other modes can be displayed. For example, FIG. 48 shows an airplane icon 291 that indicates that the portable oxygen concentrator is being operated in a mode best suited for us on an airplane. For example, traveling on an airplane may require dealing with the pressure changes associated with pressurizing and de-pressuring a cabin of an aircraft. The portable oxygen concentrator can be provided with one or more pressure senses that detect atmospheric pressure and operate the device accordingly to take into account the detect pressure of the environment in which the device is located.

Figure 53:
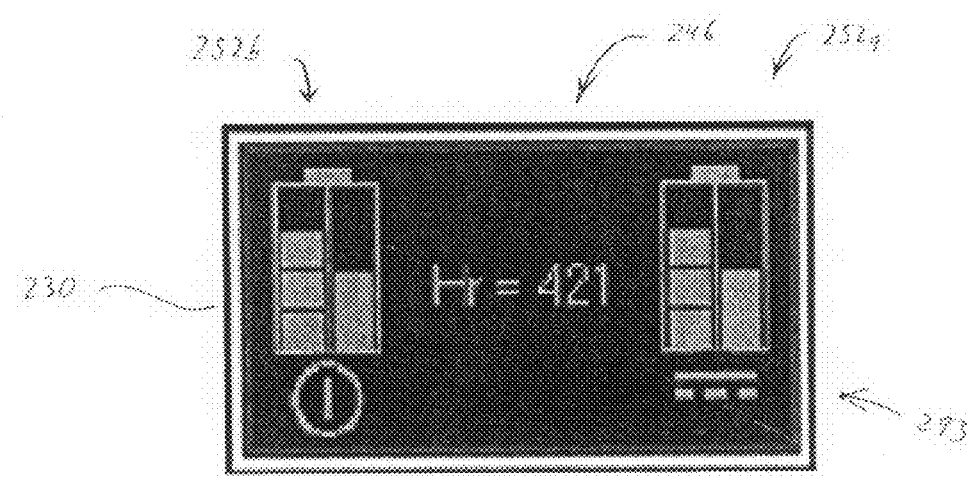

FIG. 53 shows another example of the icons that can be displayed upon startup of portable oxygen concentrator apparatus 10. In this example, two batteries are provided in the portable oxygen concentrator, as indicated by battery icons 252a and 252b. Each battery is approximately ½ full, as indicated by the bar on the right side of each battery being one half of the total height battery icon. Each battery is charging, as indicated by the scrolling bar on the left side of each battery icon. The portable oxygen concentrator has been used for a total of 421 hours, as indicated by number of hours field 246. In addition, portable oxygen concentrator apparatus 10 is connected to a DC power supply, as indicated by DC power supply icon 293.

It can be appreciated that the present invention is not intended to be limited to the icons and fields shown in the figures and/or described herein. Other information can be provided in virtually any format, including animation and sounds. In addition, combinations of information can be provided. By providing a large amount of functionality using a single touch screen display, the present invention avoids the need for separate or dedicated input/output devices. For example, following devices are typically used in a conventional oxygen concentrator and can be eliminated in the present invention in favor of using touch screen 230 to accomplish each of their functions: an on/off switch, a flow setting knob, a flow setting indication (flow meter or digital indicator), operating status/alarm LEDs, and power and/or battery indicators.

As discussed above with respect to FIG. 52, the present invention contemplates providing hidden icons on touch screen 230 that can be activated to access functions that should only be performed by someone with authorization to do so, such as a technician. For example, a portion of touch screen 230 that is not designated by any icon may becomes active during start-up. Pressing that portion of the screen provides access to a service/setup menu that allows the user to perform advanced features, such as calibrating the oxygen sensor.

J. Performance Comparison

Apparatus 10 has several features that enable it to provide better performance in terms of oxygen output than conventional portable oxygen concentrators, such that the AirSep Lifestyle and Inogen concentrators, for a given size, size, weight and sound level. For example, apparatus 10 includes a high output, high-efficiency 3-head radial air compressor/motor that in an exemplary embodiment, weights only 516 grams (1.14 lbs). In addition, integrated, light weight components are selected for the other features of the apparatus. The canisters in the sieve beds in an exemplary embodiment have a wall thickness of 0.020 inch. In addition, by providing the air manifold and oxygen delivery manifolds with integrated gas flow paths and having these manifolds define the structural support for other components, the overall number of components, complexity, size, and weight is minimized. The use of a touch screen in place of traditional discrete user controls minimizes size and weight. In addition, carrying bag 200 helps reduce weight and noise. The PSA process is optimized for lowest power/highest oxygen output (i.e. (a) oxygen concentration reduced to 88%, (b) varying the cycle times limit peak pressure to just 12 psig). The use of two internal batteries also allows apparatus 10 a relatively large portable power supply.

The result of these design optimizations the portable oxygen concentrator of the present invention has performance capabilities beyond that of conventional portable oxygen concentrator. FIG. 34 is a table that lists the features of the present invention using two batteries as compared to four other conventional devices advertised as being portable oxygen concentrators.

One interesting parameter that can be deducted from the chart shown in FIG. 34 is the ratio of the oxygen generation and battery life to the total weight of the unit. This parameter is determined as follows:

$$R_{ODW} = (O_2\ output \cdot duration)/total\ weight, \quad (4)$$

where $O_2$ output is the 100% oxygen output, which is determined from Equation (1) and/or the chart of FIG. 12, duration is the operating life of the apparatus for the given amount of batteries, and weight is the total weight of the unit including all components. Table 3 below provides the $R_{ODW}$ for the apparatus of the present invention using 1, 2, or 3 batteries (each weighing 1.5 lbs) and existing portable oxygen concentrators.

TABLE 3

|  | 100% Equivalent $O_2$ Output (1 pm) | Duration (hours) | Weight (lbs) | $R_{ODW}$ (1 pm-hr)/lb |
|---|---|---|---|---|
| Present Invention (1 battery) | 0.9 | 4 | 8.3 | 0.43 |
| Present Invention (2 batteries) | 0.9 | 8 | 9.8 | 0.73 |
| Present Invention (3 batteries) | 0.9 | 12 | 11.3 | 0.95 |
| Inogen | 0.65 | 3 | 9.7 | 0.20 |
| AirSep LifeStyle | 0.6 | 0.83 | 9.8 | 0.05 |
| AirSep FreeStyle | 0.36 | 2.5 | 4.4 | 0.20 |
| AirSep FreeStyle w/battery belt | 0.36 | 6.0 | 6.2 | 0.35 |
| SeQual | 2.65 | 2.0 | 17.4 | 0.30 |

For the Inogen, AirSep LifeStyle, and Airsep Freestyle devices, the $O_2$ output is estimated based on measurements of the operation of the device and/or a similar device converted to a 100% oxygen equivalent, which is shown in FIG. 34. For example, for the Sequal device, the oxygen output has to be converted to a 100% oxygen equivalent using the correction factors from Equation (1) and/or the chart shown in FIG. 12. More specifically, the SeQual device has an output of 3.0 lmp at 91% oxygen purity. Converting this to a 100% purity equivalent is done as follows: 3.0/1.13 (1.13 is selected from FIG. 12 using a 91% purity level), to yield a 100% purity equivalent of 2.65 lpm.

It can be appreciated from Table 3 that the apparatus of the present invention has a much greater $R_{ODW}$ than that of existing devices. This means that, as compared to other portable oxygen concentrators, the apparatus of the present invention is very efficient in terms of the actual overall mass of the product and its ability to generate oxygen. For each pound of the apparatus, the oxygen concentrator of the present invention provides a higher flow of oxygen for a longer period of time than existing devices.

K. Sound Versus Battery Life

FIG. 35 is a chart illustrating various performance criteria for apparatus 10 using two batteries at different pulse settings. It can be appreciated from reviewing this figure that the apparatus of the present invention has a long operating life and accomplishes this at sound levels that are relatively low. For example, the device of the present invention lasts a least 10 hours at a dB level less than 50. The chart also clearly demonstrates the relationship between the pulse settings and the performance of the apparatus, such as the minute volume of oxygen, the oxygen concentration, gas bolus size delivered during each, sound, power, and battery life. In this chart, the "maximum" battery run time is the theoretical maximum of the battery, and the "nominal" battery run time is the typical or published run time that can be routinely achieved under normal operating conditions.

To better understand how the combination of operating life (duration) and sound in the present invention are superior to that of existing devices, consider the ratio of duration to sound ($R_{DS}$), which is defined as duration/sound level. Table 4 below summaries the $R_{DS}$ of the present invention and that of existing portable oxygen concentrators.

TABLE 4

|  | Duration (hours) | Sound (dB) | $R_{DS}$ (duration/sound) |
|---|---|---|---|
| Present Invention (1 battery) | 4 | 55 | 0.073 |
| Present Invention (2 batteries) | 8 | 55 | 0.145 |
| Present Invention (3 batteries) | 12 | 55 | 0.218 |
| Inogen | 3 | 35.2 | 0.085 |
| AirSep LifeStyle | 0.93 | 55 | 0.017 |
| AirSep FreeStyle | 2.5 | 55 | 0.045 |
| AirSep FreeStyle (w/battery pack) | 6 | 55 | 0.090 |
| SeQual | 1.41 | 48 | 0.024 |

It can be appreciated the present invention using two batteries provides a duration to sound ratio that is significantly higher than existing devices.

L. Weight Optimization

It is axiomatic that the size of the battery contributes to both the total weight and the operating duration of the portable oxygen concentrator. The more battery size that is added to the apparatus the longer the unit will operate, which is a desirable feature. However, adding batteries to the apparatus will cause it to weigh more, which is not a desirable feature. The portable oxygen concentrator of the present invention has the ability to operate using one or two batteries, allowing the user to determine how much weight to add for the desired amount of operating time.

In an exemplary embodiment, the weight of each battery is approximately 1.5 lbs. The weight of the apparatus without any batteries is approximately 7.8 lb. With one battery used in the apparatus, the total weight of the portable oxygen concentrator is approximately 8.3 lb. It can thus be appreciated that with one batter, the weight of the battery alone represents approximately 17.6% of the total weight of the apparatus.

With two batteries used in the apparatus, the total weight of the portable oxygen concentrator is approximately 9.8 lbs. It can thus be appreciated that with two batteries, the weight of the batteries alone represents approximately 30.6% of the total weight of the apparatus. Table 5 below summarizes the information provided above, in addition to showing how additional 1.5 lb battery packs contribute to the total weight of the apparatus.

TABLE 5

| Number of Batteries | Total Weight of Batteries (lbs) | Total Weight of Apparatus with Batteries (lbs) | Percent Total Weight Due to Batteries (%) | Percent Total Weight of all Non-Battery Components (%) |
| --- | --- | --- | --- | --- |
| 0 | 0   | 6.8  | 0.0  | 100.0 |
| 1 | 1.5 | 8.3  | 17.6 | 82.4  |
| 2 | 3.0 | 9.8  | 30.6 | 69.4  |
| 3 | 4.5 | 11.3 | 39.8 | 60.2  |
| 4 | 6.0 | 12.8 | 46.8 | 53.2  |

It can be appreciated from reviewing Table 5 that the portable oxygen concentrator of the present invention is capable of providing a relatively high output of oxygen (0.90 lpm) for a duration of at least eight hours and the total battery weight is only 30.6% of the total weight of the system.

In a conventional portable oxygen concentrator, the weight of the compressor typically contributes to a relatively large percentage of the total weight of the system. The compressor described above provides a high output at a relatively small weight. Table 6 below shows how the weight of the compressor contributes to the total weight of the system.

TABLE 6

| Number of Batteries | Weight of Compressor (lbs) | Total Weight of Apparatus with Batteries (lbs) | Percent Total Weight of the Compressor (%) | Percent Total Weight of all Non-Compressor Components (%) |
| --- | --- | --- | --- | --- |
| 0 | 1.14 | 6.8  | 16.8 | 83.2 |
| 1 | 1.14 | 8.3  | 13.8 | 86.2 |
| 2 | 1.14 | 9.8  | 11.6 | 88.4 |
| 3 | 1.14 | 11.3 | 10.1 | 89.9 |
| 4 | 1.14 | 12.8 | 8.9  | 91.1 |

M. Oxygen Conserving Devices

In the embodiments described above, a single lumen cannula is used to deliver the flow of gas to the user. This same cannula is used to sense the changes in pressure and/or flow so that the device can detect when to deliver the bolus of oxygen. Based on the pressure measured by pressure sensor 122, controller 22 causes oxygen delivery valve 116 to control the flow of gas so that it is delivered to the patient only during the inspiratory phase of the respiratory cycle. This is an example of an electronic conserver, which is built into apparatus 10.

The present invention further contemplates that the electronic pressure sensor and electronic valve can be replaced with a single lumen pneumatic oxygen conserving device. A pneumatic oxygen conserving device has the advantage in that it does not require electrical energy to cause the gas flow to be delivered only during inspiration, thus saving battery life. Examples of pneumatic oxygen conserving devices suitable for use in the present invention are disclosed in U.S. Pat. Nos. 5,881,725; 6,484,721; 6,568,391; and 6,752,152, the contents of each or which are incorporated herein by reference.

The present invention contemplates that a dual lumen cannula system can be used in place of the single lumen system described above with respect to the pneumatic oxygen conserving device. In a dual lumen pneumatic system, one lumen in the cannula is used to deliver gas to the patient and the other lumen is in fluid communication with the airway, such as the nares, to sense gas flow and/or pressure of the user. A flow and/or pressure sensor is coupled to the other end of the cannula. In this embodiment, a second prong or barb would be needed on apparatus 10 and a flow sensor, pressure sensor, or both are coupled to the second barb.

Figure 36:
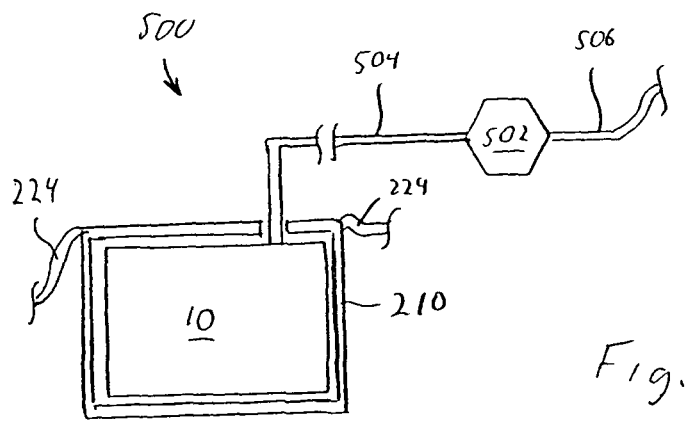
FIG. 36 is a schematic illustration of an oxygen concentration system that includes an oxygen concentrator and an oxygen conserving device that is separate from the oxygen concentrator.

The present invention further contemplates that the oxygen conserving function can be provided in a separate oxygen conserving device, electronic or pneumatic, that is not attached to oxygen concentration system 10. In other words, an electronic or pneumatic oxygen conserver can be provided at a location external or not integral with apparatus 10. In FIG. 36, a oxygen concentration system 500 is shown that includes an oxygen concentrator 10 contained in a housing and an electronic or pneumatic oxygen conserver 502 that is physically spaced apart from the housing of the oxygen concentrator. The oxygen conserver can include fasteners, straps, clips or other devices to enable the oxygen conserver to be attached to the user, to bag 210, and or a part of the bag, such as the carrying strap 224. In this illustrated exemplary embodiment, a length of cannula 504 separates oxygen conserver 502 from oxygen concentration system 500. Another annular 506 communicates gas from oxygen conserver 502 to the user (not shown). Oxygen concentration system 10 can be provided in a carrying bag 210, if desired. This configuration for the oxygen concentration system of the present invention avoids the extra weight, complexity, and power consumption from being included in apparatus 10.

Figure 37:
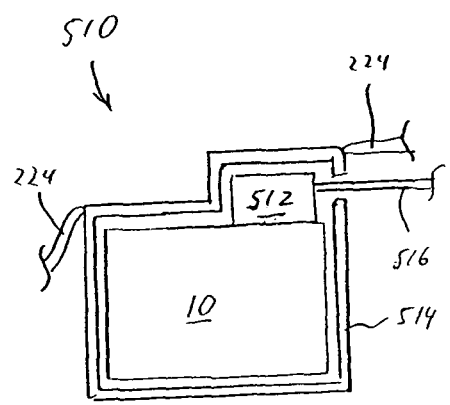
FIG. 37 is a schematic illustration of an oxygen concentration system that includes an oxygen concentrator and an oxygen conserving device disposed in a common chamber in a carrying bag.

The separate oxygen conserver can also be a modular device that attaches to apparatus 10 and/or carrying case 210 when desired. FIG. 37 illustrates an oxygen concentration system 510 in which an oxygen conserver 512 is selectively attachable to apparatus 10. For example, oxygen conserver 512 can include a recess for receiving barb 139 and mechanisms can be provided to join the oxygen conserver to apparatus 10 such that they can be separated from one another. In the illustrated embodiment, a carrying bag 514 is provided that encapsulates both oxygen concentration system 510 and oxygen conserver 512, with a cannula 516 extending from the bag.

Figure 38:
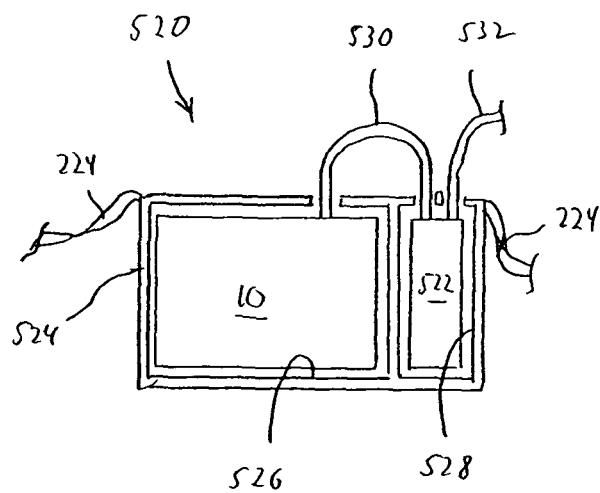
FIG. 38 is a schematic illustration of an oxygen concentration system that includes an oxygen concentrator and an oxygen conserving device disposed in a carrying bag in separate chambers.

FIG. 38 illustrates an oxygen concentration system 520 in which an oxygen conserver 522 is selectively attachable to apparatus 10 and is contained in a carrying bag 524 that also contains apparatus 10. In the embodiment, carrying bag 524 includes a first chamber 526 that housing apparatus 10 and a second chamber or pocket 528 that houses oxygen conserver 522. This allows the user to leave pocket 528 empty or used for other purposes if oxygen conserver 522 is not needed. A jumper cannula 530 or other pneumatic connection is provided to connected the outlet of the oxygen concentration system with the inlet of the oxygen conserver. A delivery cannula 532 is provided to communicate the oxygen enriched gas from oxygen conserver 522 to the user.

N. Use in a Liquefaction or Trans-Fill System

Figure 39:
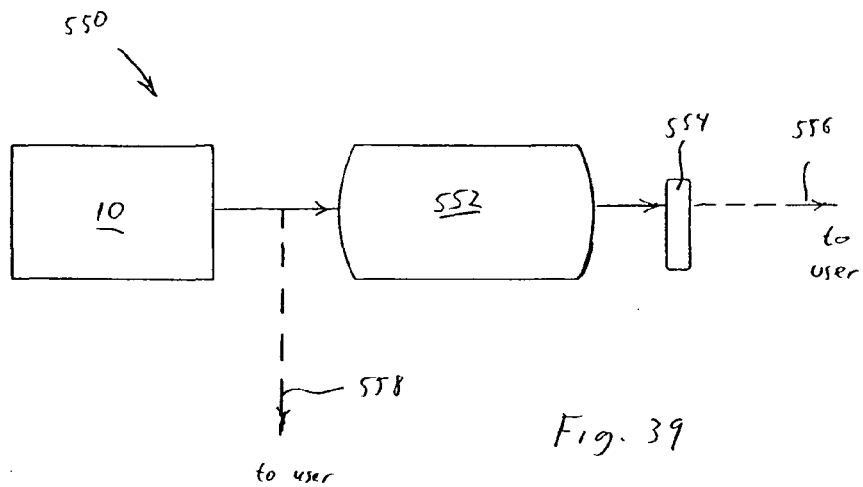
FIG. 39 is a schematic diagram of a liquefaction system using the oxygen concentration system of the present invention.

The present invention contemplates using apparatus 10 as part of or in combination with other types of oxygen generation/delivery systems. For example, apparatus 10 can be used in a liquefaction system, which is a system that produces liquid oxygen for user consumption. As shown in FIG. 39, a typical liquefaction system 550 includes an oxygen concentrator 10 that provides gas for liquefying to a cryogenic cooling system 552, which lowers the temperature of the gas level that causes the oxygen to change state from a gas to a liquid. The liquid oxygen can be stored in a storage vessel 554, typically referred to as a dewer, that is easily transported by the user. The user can breathe gaseous oxygen from the storage vessel as indicated by arrow 556, from the output of the oxygen concentrator as indicated by arrow 558, or both. This enables the user to have a supply of liquid oxygen for transportation and consumption.

An optional valve can be provided to control the flow of oxygen enriched gas to the user or the cryogenic cooling system 552 so that the gas is delivered to one or the other or to both simultaneously. In addition, an internal dewer can be provided in the liquefaction system to allow the system to generate liquid oxygen even when the portable dewer is not attached to the system. Liquid oxygen from the internal dewer can be provided to the portable dewer when the portable dewer is connected to the liquefaction system. Examples of liquefaction systems suitable for use in the present invention are described in U.S. Pat. Nos. 5,893,275; 5,979,440; 6,212,904; 6,314,957; 6,651,653; 6,681,764; and 6,698,423, the contents of each of which are expressly incorporated herein by reference.

The features of apparatus 10, such as the compressor, sieve beds, and operation, can be incorporated into the liquefaction system such that the oxygen concentrator and the components of the liquefaction system, such as the refrigeration system, are combined into a common device. Because apparatus 10 of the present invention provides a lightweight concentrator with a relatively high oxygen flow output and long duration battery life, the inclusion of the apparatus 10 in a liquefaction system provides a liquefaction system that is capable of being ambulatory, i.e., transported by a user, and operated without an AC power supply. The present invention also contemplates that apparatus 10 can be separate from the rest of the liquefaction system. This enables each component of the liquefaction system to be more easily transported individually.

Figure 40:
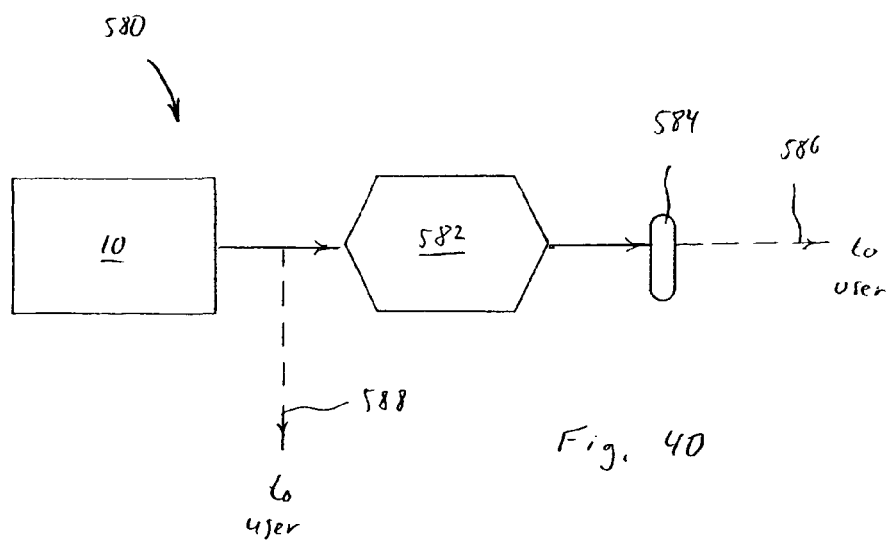
FIG. 40 is a schematic diagram of a transfill system using the oxygen concentration system of the present invention.

Apparatus 10 can also be used in a transfill system 580 as schematically illustrated in FIG. 40. A transfill system is a system that compresses a gas, such as concentrated oxygen, and provides the compressed gas to storage vessel, such as a portable oxygen tank. In a typical transfill system, oxygen from an oxygen concentrator 10 is provided to a compressor 582, such as a piston compressor, where it is compressed to a relatively high pressure, e.g., from 1500 to 3500 psi. The compressed gas s provided to a portable storage vessel 584 that is capable of being carried or otherwise transported by the user. The user can breathe gaseous oxygen from storage vessel 584 as indicated by arrow 586, from the output of the oxygen concentrator (apparatus 10) as indicated by arrow 588, or both. This enables the user to have a supply of high pressure oxygen for transportation and consumption.

An optional valve can be provided to control the flow of oxygen enriched gas to the user or to the compressor 582 so that the gas is delivered to one or the other or to both simultaneously. In addition, an internal storage vessel can be provided in the transfill system to allow the system to produce high pressure oxygen enriched gas even when the portable storage vessel is not attached to the system. High pressure oxygen enriched gas from the internal storage vessel can be provided to the portable storage vessel when the portable storage vessel is connected to the transfill. Examples of transfill systems for use in the present invention are described in U.S. Pat. Nos. 5,071,453; 5,354,361; 5,858,062; 5,988,165; 6,302,107; 6,446,630; 6,889,726; 6,904,913, and 6,923,180 and in European Patent Application No. 0 247 365 A2, the contents of each of which are expressly incorporated herein by reference.

The features of apparatus 10, such as the compressor, sieve beds, and operation, can be incorporated into the transfill system such that the oxygen concentrator and the components of the transfill system, such as the high pressure compressor, are combined into a common device. Because apparatus 10 of the present invention provides a lightweight concentrator with a relatively high oxygen flow output and long duration battery life, the inclusion of the apparatus 10 in a transfill system provides a transfill system that is capable of being ambulatory, i.e., transported by a user, and operated without an AC power supply. The present invention also contemplates that apparatus 10 can be separate from the rest of the transfill system. This enables each component of the transfill system to be more easily transported individually.

O. Sound Reduction

In order to make apparatus 10 as quiet as possible, the present invention contemplates several techniques for reducing the sound generated by the apparatus. Sound can be generated from different portions of the portable oxygen concentrator. One such source is the flow of gas into and around the apparatus. To suppress the noise due to this flow, the present invention contemplates providing baffles in passages 62-68. Examples of such baffles include protrusion or angled projections that extend into the passages from the passage walls.

Another source of sound is compressor 14. Sound from the compressor is believed to come from sound associated with the movement of the parts of the compressor and sound caused by vibration induced by the operation of the compressor. To suppress the sound resulting from the movement of the parts of the compressor, the present invention contemplates providing a muffler at or proximate to the inlet of the compressor. The muffler at the inlet prevents or reduces noise generated within the compressor from traveling back up the inlet passage and exiting the compressor inlet flow path.

Figure 41:
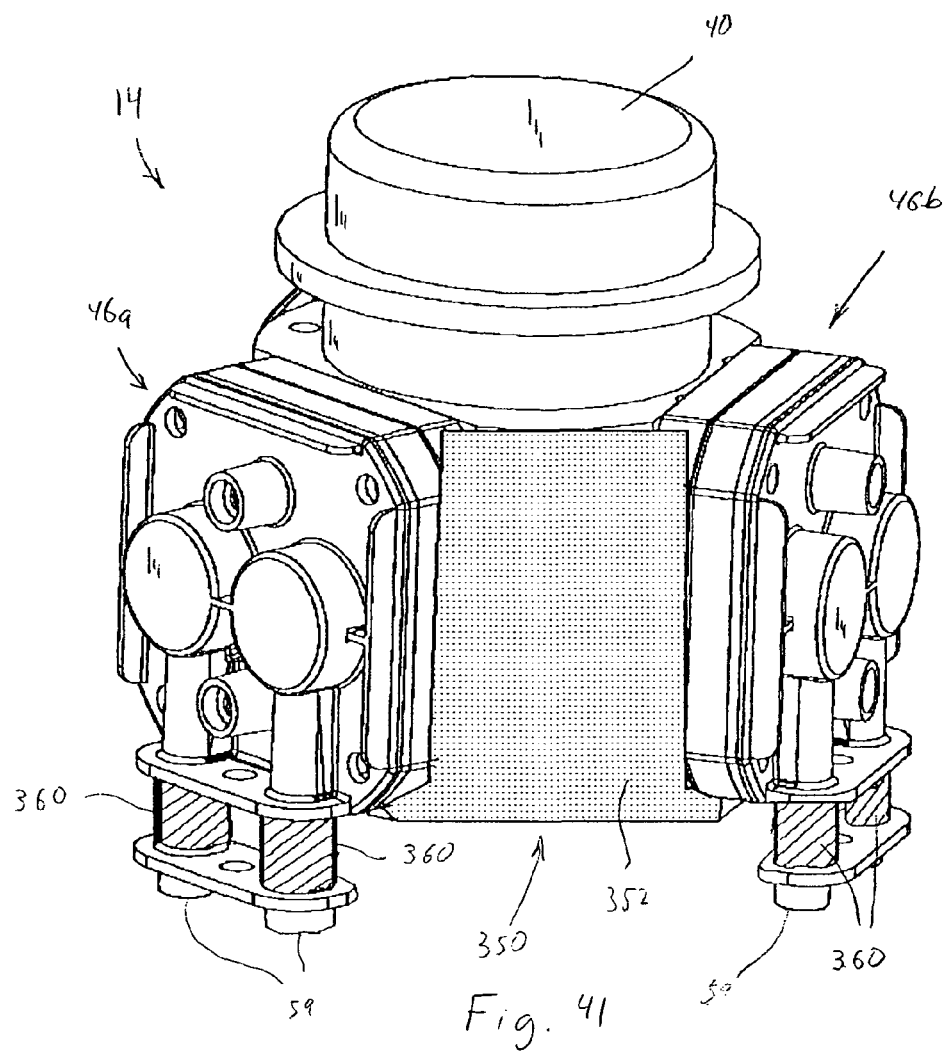
FIG. 41 is a perspective view of a compressor and sound reducing techniques for use with the compressor.

As shown in FIG. 41, the present invention also contemplates providing a compressor jacket 350 that covers or overlies at least a portion of the compressor. In the illustrated embodiment, compressor jacket 350 includes a plurality of panels 352 only one of which is illustrated and/or visible in FIG. 41. Panel 352 is provided on compressor 14 such that each panels is disposed between each compressor head 46 and overlies cam assembly 42, which is shown in FIG. 5A. Panels 352 are made from a sound absorbent material and are attached to the compressor, directly or indirectly, using any technique. In the illustrated embodiment, the panels only cover the area between the compressor head to prevent heat build-up. It is to be understood, however, that the size, shape, and location of the panels can vary. For example, the present invention contemplates providing compressor jacket 350 around the entire compressor.

In the illustrated embodiment, compressor 14 is mounted directly to air manifold 16. This direct mounting of the compressor on the manifold may impart vibrations from the compressor to the manifold, which can result in the generation of noise. To prevent such translation of vibration, the present invention contemplates providing isolators 360 between compressor 14 and the manifold (not shown in FIG. 37) to which the compressor is attached. In an exemplary embodiment, isolators 360 are defined by a flexible tube, such as rubber, provided at the inlet and outlet of each compressor head. Vibration that occurs in compressor 14 during its operation is prevented from translating to the manifold by isolators 360.

P. Battery Life Optimization

Figure 42:
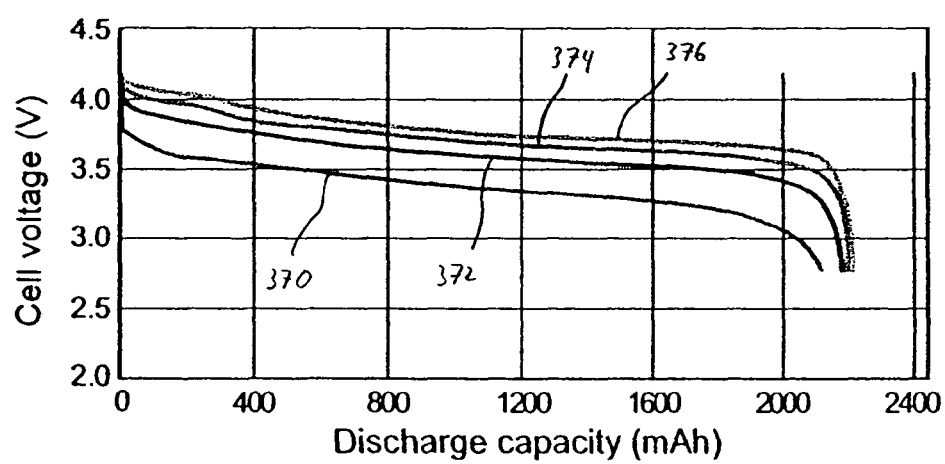
FIG. 42 is a chart showing the discharge rate characteristic of a battery suitable for use in the present invention.

In an exemplary embodiment of the present invention, the portable oxygen concentrator uses a Li-Ion cell in the battery or batteries, collectively referred to as the battery pack, that provide power to the various components of the system. Li-Ion cells have a known discharge rate characteristic, an example of which is shown in FIG. 42. The x-axis is mA-hr or milli-ampere X hours. At 0 mA-hr, the Li-Ion cell has 100% capacity remaining. At 2100 mA-hr, the cell has 0 capacity remaining. Each line 370, 372, 374, and 376 in this figure shows how the voltage decreases over time (progressively larger mA-hr) at different discharge currents. In this chart, current draw is varied by 10× from 0.42-4.2 A. The higher the current draw, the lower the voltage for the same energy (mA-hr) consumed.

In apparatus 10 of the present invention, the current draw from the battery pack is limited to approximately 4 amps or less during the sieve bed pressurization. However, the battery pack has the capability to discharge at 8 amps. By limiting the peak current to 4 A, the effect is to avoid operation on the line 370, and, instead, operate on line 372, e.g., by limiting the current draw to half of the maximum current. As shown in FIG. 42, lines 372, 374, or 376 are relatively similar, so that there is a minimal reduction in run time when the apparatus is operating in that current range. It is only when the current is increased to line 370 that a notable reduction is run time occurs.

The apparatus of the present invention matches the PSA process, and motor maximum current to the discharge characteristics inherent in a Li-Ion cell, so that the apparatus "squeezes" all of the energy out of the battery pack so that the actual run time approaches the maximum theoretical run time. In addition, when two batteries (cells) are used in the battery back, the current drawn from each batter is further limited, so that each battery is operating on an even lower current line, such as lines 374 or 376.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A user interface for operating a portable oxygen concentrator that includes a power supply and for deactivating the portable medical device, comprising:
    a touch screen; and
    a controller coupled to the touch screen, the controller configured to
        (a) display a first icon in an initial location on the touch screen,
        (b) detect a user touching the first icon,
        (c) display a second icon on the touch screen after the user has touched the first icon, wherein the second icon is displayed in a different location than the initial location, regardless of where on the touch screen the first icon has been displayed,
        (d) detect a user touching the second icon, and
        (e) deactivate the portable oxygen concentrator responsive to detection of the second icon being touched by suspending a supply of power from the power supply to the portable oxygen concentrator.

2. The user interface of claim 1, wherein the controller comprises a timer, and wherein the controller is configured for resetting the touch screen if the second icon on the touch screen is not touched within a predetermined time after detection of the user touching the first icon.

3. The user interface of claim 1, wherein the first icon comprises a symbol, and wherein the second icon comprises a power interface button.

4. The user interface of claim 1, wherein the first icon is a power interface button.

5. The user interface of claim 1, wherein the first icon is a virtual power button.

6. The user interface of claim 3, wherein the symbol represents a power button.

7. The user interface of claim 4, wherein the second icon is a second power interface button.

8. The user interface of claim 5, wherein the second icon is a second virtual power button.

9. The user interface of claim 6, wherein the second icon is larger than the first icon.

10. A method for operating an oxygen concentrator that includes a power supply and for deactivating the oxygen concentrator, comprising:
    (a) displaying a first icon in an initial location on a touch screen;
    (b) detecting a user touching the first icon;
    (c) displaying a second icon on the touch screen after the user has touched the first icon, wherein the second icon is displayed in a different location than the initial location, regardless of where on the touch screen the first icon has been displayed;
    (d) detecting a user touching the second icon; and
    (e) deactivating the oxygen concentrator responsive to detection of the second icon being touched by suspending a supply of power from the power supply to the oxygen concentrator.

11. The method of claim 10, wherein the first icon represents a power button.

12. The method of claim 10, wherein the first icon includes a symbol that represents a power button, and wherein the second icon includes the symbol.

13. The method of claim 10, wherein the first icon is a power interface button.

14. The method of claim 10, wherein the first icon is a virtual power button.

15. The method of claim 13, wherein the second icon is a second power interface button.

16. The method of claim 12, wherein the second icon is larger than the first icon.

17. The method of claim 14, wherein the second icon is a second virtual power button.

18. A user interface for operating a portable oxygen concentrator, comprising:
    a touch screen; and
    a controller coupled to the touch screen, the controller configured to
        (a) display a first power button in an initial location on the touch screen,
        (b) detect a user touching the first power button,
        (c) display a second power button on the touch screen after the user has touched the first power button, wherein the second power button is displayed in a different location than the initial location, regardless of where on the touch screen the first power button has been displayed,
        (d) detect a user touching the second power button, and
        (e) deactivate the portable oxygen concentrator responsive to detection of the second power button being touched by suspending the supply of power from the power supply to the portable oxygen concentrator.

* * * * *